(12) United States Patent
Minczuk et al.

(10) Patent No.: US 10,596,227 B2
(45) Date of Patent: Mar. 24, 2020

(54) POLYPEPTIDE TARGETING TO MITOCHONDRIA

(71) Applicant: Medical Research Council, London (GB)

(72) Inventors: Michal Minczuk, London (GB); Monika A. Papworth, Cambridge (GB); Aaron Klug, London (GB)

(73) Assignee: United Kingdom Research and Innovation, Swindon (GB)

( * ) Notice: Subject to any disclaimer, the term of this patent is extended or adjusted under 35 U.S.C. 154(b) by 387 days.

(21) Appl. No.: 14/859,596

(22) Filed: Sep. 21, 2015

(65) Prior Publication Data

US 2016/0199443 A1 Jul. 14, 2016

Related U.S. Application Data

(60) Division of application No. 12/143,886, filed on Jun. 23, 2008, now Pat. No. 9,139,628, which is a continuation-in-part of application No. PCT/GB2006/004755, filed on Dec. 19, 2006.

(30) Foreign Application Priority Data

Dec. 23, 2005 (GB) .................................. 0526449.4

(51) Int. Cl.
| | |
|---|---|
| A61K 38/17 | (2006.01) |
| A61K 38/46 | (2006.01) |
| A61K 38/45 | (2006.01) |
| C12N 9/14 | (2006.01) |
| C12N 9/10 | (2006.01) |
| C07K 14/47 | (2006.01) |

(52) U.S. Cl.
CPC .......... *A61K 38/1709* (2013.01); *A61K 38/45* (2013.01); *A61K 38/46* (2013.01); *C07K 14/47* (2013.01); *C12N 9/1007* (2013.01); *C12N 9/14* (2013.01); *C07K 2319/07* (2013.01); *C07K 2319/095* (2013.01); *C07K 2319/81* (2013.01); *C12Y 201/01072* (2013.01); *C12Y 306/03014* (2013.01)

(58) Field of Classification Search
None
See application file for complete search history.

(56) References Cited

U.S. PATENT DOCUMENTS

| | | | |
|---|---|---|---|
| 2003/0104479 A1* | 6/2003 | Bright ..................... | C12N 15/62 435/7.1 |
| 2003/0180801 A1* | 9/2003 | Maekawa .......... | C12N 15/1051 435/7.1 |
| 2004/0072774 A1* | 4/2004 | Manfredi ............. | C12N 9/0053 514/44 R |

FOREIGN PATENT DOCUMENTS

WO 01/52620 7/2001

OTHER PUBLICATIONS

Durai et al. "Zinc finger nucleases: custom-designed molecular scissors for genome engineering of plant and mammalian cells," 5978-5990 Nucleic Acids Research, 2005, vol. 33, No. 18 (Year: 2005).*
Matheny, et al. "The Nuclear Localization Signal of NGFI-A is located within the Zinc Finger DNA Binding Domain*" The Journal of Biological Chemistry, Mar. 1994, 269(11):8176-8181.
Kanwal, et. al., "Bidirectional on/off switch for controlled targeting of proteins to subcellular compartments", Journal of Controlled Release, 2004, 98:379-393.
Pfanner, et al. "Versatility of the mitochondrial protein import machinery" Nat Rev Mol Cell Bioi, 2001, 2(5):339-349.
Carvin, et al. "Site-selective in vivo targeting of cytosine-5 DNA methylation by zinc-finger proteins" Nucleic Acids Research, 2003, 31(22):6493-6501.
Papworth, et al. "Inhibition of herpes simplex virus 1 gene expression by designer zinc-finger transcription factors" Proceedings of the National Academy of Sciences of the United States of America, Feb. 2003, 100(4):1621-1626.
Kutay, et al. "Leucine-rich nuclear-export signals:born to be weak" Trends in Cell Biology, Mar. 2005, 15(3):121-124.
Bayona-Bafaluy, et al. "Rapid directional shift of mitochondrial DNA heteroplasmy in animal tissues by a mitochondrially targeted restriction endonuclease" Proceedings of the National Academy of Sciences of the United States of America, Oct. 2005, 102(40):14392-14397.
Gupta, et al. "The gene and processed pseudogenes of the rat mitochondrial single-strand DNA-binding protein: structure and promoter strength analyses" Gene: An International Journal of Genes and Genomes, Jun. 1998, 212 (2):269-278.
Minczuk, et al. "Sequence-specific modification of mitochondrial DNA using a chimeric zinc finger methylase" Proceedings of the National Academy of Sciences of the United States of America, Dec. 2006, 103(52):19689-19694.
Papworth, et al. "Designer zinc-finger proteins and their applications" Gene: An International Journal of Genes and Genomes, Nov. 2005, 366(1):27-38.

* cited by examiner

*Primary Examiner* — Christina Bradley
(74) *Attorney, Agent, or Firm* — Pasternak Patent Law

(57) ABSTRACT

Methods for delivering non-mitochondrial proteins to mitochondria are provided. Also provided are nucleic acid constructs comprising a coding sequence encoding a DNA-binding polypeptide, fused to a mitochondrial targeting sequence (MTS) and a nuclear export signal (NES), and the encoded proteins. The construct successfully delivers DNA binding proteins to the mitochondrion. A chimeric methylase based on the above construct is successfully delivered to mitochondria, resulting in modification of mtDNA.

13 Claims, 9 Drawing Sheets

Specification includes a Sequence Listing.

A F-ZFP$_{NARP}$-meth-NES / F-ZFP$_{cont}$-meth-NES
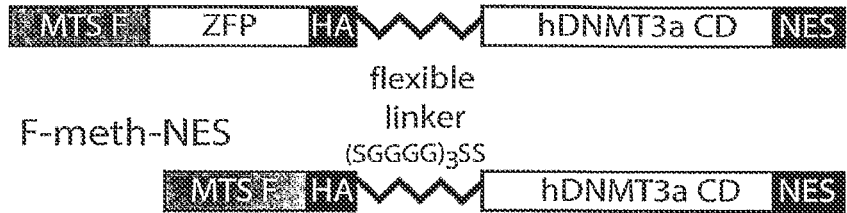
F-meth-NES
flexible linker (SGGGG)$_3$SS
B
| Fraction | T | C | Mitochondria | | | |
|---|---|---|---|---|---|---|
| Proteinase K [µg/ml] | - | - | - | 2 | 2 | 5 | 2 |
| Time [min] | - | - | - | 10 | 20 | 20 | 10 |
| Triton X [%] | - | - | - | - | - | - | 1 |
| F-ZFP$_{NARP}$-meth-NES | p m | | | | | | |
| GAPDH | | | | | | | |
| mtTFAM | | | | | | | |
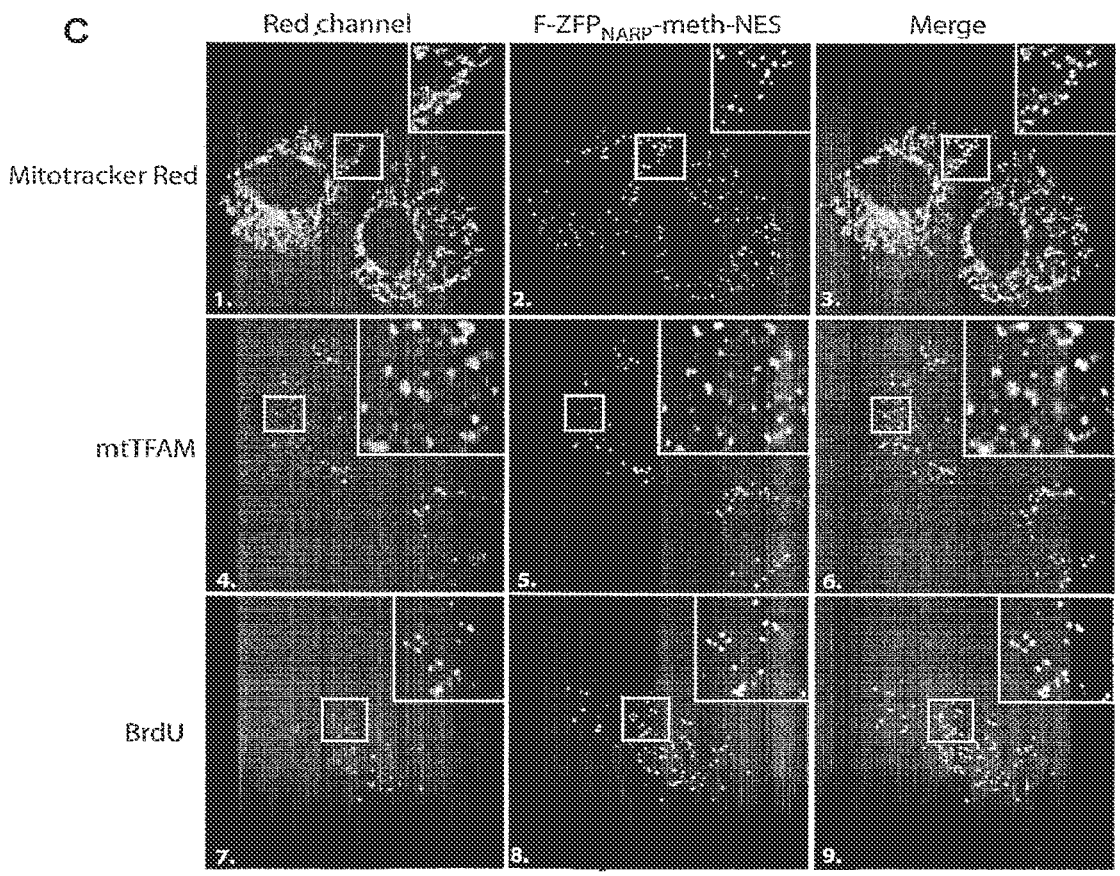
FIG. 3

Group 1

```
              F1                               F2
            -1123456                         -1123456
5    MAERPFQRICMRNFSRSDVLSAHIRTHAGEKPFACDICGRKFARNDHRINHTKIDTG----  57
9    MAERPFQCRICMRNFSRSDHLSTHIRTHTGEKPFACDICGRKFAHSNTRKNHTKIHTGGGG  61
10   MAERPFQCRICMRNFSRSDVLSVHIRTHTGEKPFACDICGRKFATNQHRTKHTKIHTG---  59
11   MAERPFQCRICMRNFSRSDHLSQHIRTHTGEKPFACDICGRKFATSSNRKTHTKIHTG---  59
12   MAERPFQCRICMRNFSRSDHLSEHIRTHTGEKPFACDICGRKFARKDARITHTKIHTGGGG  61
15   MAERPFQCRICMRNFSRSDHLSNHIRTHTGEKPFAQNICGRKFARNDRKKHTKIHTG----  59
18   MAERPFQCRICMRNFSRSDHLSQHIRTHTGEKPFACDICGRKFATSSNRKTHTKIHTG---  59
19   MAERPFQCRICMRNFSRSDHLSEHIRTHTGEKPFACDICGRKFADSSHRTRHTKIHTGGGG  61
21   MAERPFQCRICMRNFSRSDHLSEHIRTHTGEKPFACDICGRKFARNDNRKRHTKIHTG---  59
22   MAERPFQCRICMRNFSRSDSLSQHIRTHTGEKPFACDICGRKFANSSNRKNHTKIHTGGGG  61
26   MAERPFQCRICMRNFSRSDHLSNHIRTHTGEKPFACDICGRKFATRDTRKKHTKIHTGGGG  61
29   MAERPFQCRICMRNFSRSDTLSEHIRTHTGEKPFACDICGRKFARNDHRTTHTKIHTGGGG  61
30   MAERPFQCRICMRNFSRSDHLSEHIRTHTGEKPFACDICGRKFARNDNRKRHTKIHTG---  59
31   MAERPFQCRICMRNFSRSDHLSEHIRTHTGEKPFACDICGRKFARNDHRTTHTKIHTG---  59
34   MAERPFQCRICMRNFSRSDHLSTHIRTHTGEKPFACDICGRKFAHSNTRKNHTKIHTGGGG  61
35   MAERPFQCRICMRNFSRSDVLSVHIRTHTGEKPFACDICGRKFAQNNHRITHTKIHTG---  59
37   MAERPFQCRICMRNFSRSDALSVHIRTHTGEKPFACDICGRKFAHSDTRTKHTKIHTG---  59
     *****  ***********  **  *****:*******:***.***     *  ****.**
```

```
              F3                               F4
            -1123456                         -1123456
5    SQKPFQCRICMRNFSRSDTLSRHIRTHTGEKPFACDICGRKFAHNHHRKTHTKIHLRQK  116
9    SQKPFQCRISMRNFSRSDSLSTHIRTHTGEKPFACDICGRKFAAGANRTTHTKIHLRQK  120
10   SQKPFQCRICMRNFSRSDHLSEHIRTHTGEKPFACDICGRKFANNSSRTRHTKIHLRQK  117
11   SQKPFQCRICMRNFSRSDHLSNHIRTHTGEKPFACDICGRKFARSDDRKKHTKIHLRQK  117
12   SQKPFQCRICMRNFSRSDHLSNHIRTHTGEKPFACDICGRKFARSDDRKKHTKIHLRQK  120
15   SQKPFQCRICMRNFSRSDHLSNHIRTHTGEKPFACDICGKKFAQSATRITHTKIHLR--  115
18   SQKPFQCRICMRNFSRSDNLSTHIRTHTGEKPFACDICGRKFARSDNRTKHTKIHLRQK  117
19   SQKPFQCRICMRNFSRSDSLSVHIRTHTGEKPFACDICGRKFAQNQHRINHTKIHLRQK  120
21   SQKPFQCRICMRNFSRSDHLSQHIRTHTGEKPFACDICGRKFATSANRTTHTKIHLRQK  117
22   SQKPFQCRICMRNFSRSDSLSQHIRTHTGEKPFACDICGKKFATSSNRKTHTKIHLRQK  120
26   SQKPFQCRICMRNFSRSDALSVHIRTHTGEKPFACDICGRKFADSSHRTRHTKIHLRQK  120
29   SQKPFQCRICMRNFSRSDHLSNHIRTHTGEKPFAQNICGRKFARNDDRKKHTKIHLRQK  120
30   SQKPFQCRICMRNFSRSDHLSNHIRTHTGEKPFAQNICGRKFARNDDRKKHTKIHLRQK  117
31   SQKPFQCRICMRNFSRSDHLSEHIRTHTGEKPFACDICGRKFRRDSRTNHTKIHLRQK   117
34   SQKPFQCRICMRNFSRSDHLSEHIRTHTGEKPFACDICGRKFARNDHRTTHTKIHLRQK  120
35   SQKPFQCRICMRNFSRSDHLSTHIRTHTGEKPFACDICGRKFAASSARKTHTKIHLRQK  117
37   SQKPFQCRICMRNFSRSDVLSVHIRTHTGEKPFACDICGRKFAQNHRITHTKIHLRQK   117
     ********.********  **  **************:***:**:    *  *******
```

Group 2

```
              F1                               F2
            -1123456                         -1123456
20   MAERPYACPVESCDRRFSRSDHLTKHIRIHTGQKPFQCRICMNNFSNSDHLSRHIRTHTG----  60
27   MAERPYACPVESCDRRFSRSDHLTKHIRIHTGQKPFQCRICMNNFSNSDHLSRHIRTHTG----  60
32   MAERPYACPVESCDRRFSTNDDLNTHIRIHTGQKPFQCRICMRNFSTSSHLSRHIRTHTGGGG  63
33   MAERPYACPVESCDRRFSTNDDLNTHIRIHTGQKPFQCRICMRNFSTSSHLSRHIRTHTG----  60
     ****************** .* *..********************  ***.*.**********
```

```
              F3                               F4
            -1123456                         -1123456
20   SQKPFQCRICMRNFSRSDSLSVHIRTHTGEKPFACDICGRKFAQNQHRINHTKIHLR   117
27   SQKPFQCRICMRNFSRSDHLSNHIRTHTGEKPFACDICGRKFATRDTRKKHTKIHLR   117
32   SQKPFQCRICMRNFSRSDHLSEHIRTHTGEKPFACDICGRKFARNDNRKRHTKIHLR   120
33   SQKPFQCRICMRNFSRSDHLSEHIRTHTGEKPFACDICGRKFARNDHRTTHTKIHLR   117
     ******************  **  ***************:***  .:  *  *******
```

FIG. 5

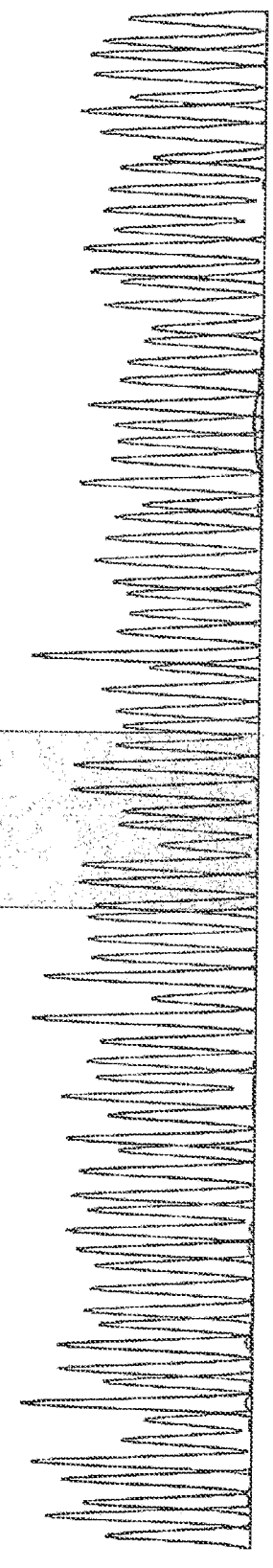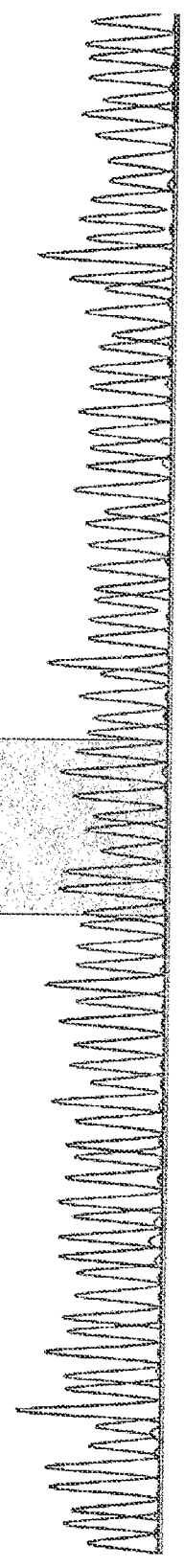
FIG. 7 CONT'D

POLYPEPTIDE TARGETING TO MITOCHONDRIA

This application is a Divisional of U.S. application Ser. No. 12/143,886 filed Jun. 23, 2008, which is a continuation-in-part application of international patent application Serial No. PCT/GB2006/004755 filed 19 Dec. 2006, which published as PCT Publication No. WO 2007/071962 on 28 Jun. 2007, which claims benefit of GB patent application Serial No. 0526449.4 filed 23 Dec. 2005.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention. It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. The embodiments of the present invention are disclosed herein or are obvious from and encompassed by, the detailed description. The detailed description is given by way of example but not intended to limit the invention solely to the specific embodiments described.

SEQUENCE LISTING

The instant application contains a Sequence Listing which has been submitted in ASCII format via EFS-Web and is hereby incorporated by reference in its entirety. Said ASCII copy, created on Dec. 16, 2010, is named 43151002.txt and is 51,479 bytes in size.

The present invention relates to the targeting of polypeptides to the mitochondrion. In particular, the invention relates to the mitochondrial targeting of polypeptides which are heterologous to the mitochondrion, such as polypeptides with very strong nuclear localisation which are resistant to delivery to the mitochondrion. The invention moreover relates to methods for modifying mitochondrial DNA using polypeptides delivered to the mitochondrion.

BACKGROUND

Mitochondria are cellular organelles found in eukaryotic cells that play a central role in energy metabolism, apoptosis and ageing. Mitochondria contain a distinct mitochondrial genome, and human mitochondria contain 2 to 10 copies of their own DNA (mtDNA) of 16,569 bp, which encodes essential components of the oxidative phosphorylation machinery. This makes the mitochondrion to a certain extent independent of the nucleus, in that proteins are synthesised directly in the mitochondrion. Mitochondrial DNA resembles prokaryotic DNA in that it is a circular double stranded molecule comprising genes that do not possess introns; moreover, its genetic code differs from the "normal" universal genetic code.

The mitochondrion is highly susceptible to mutagenesis, as a result of the presence of multiple copies of mtDNA in each cell, as opposed to a single copy of nuclear DNA. Moreover, certain repair mechanisms in mitochondria are lacking, such as nucleotide excision repair mechanisms.

Point mutations, deletions or rearrangements in human mtDNA disrupt oxidative phosphorylation leading to a range of genetic diseases for which there are currently no treatments. For example, Leber hereditary optic neuropathy (LHON) is caused by a G11778A point mutation in the gene encoding the ND4 subunit of complex I in mtDNA. Neuropathy, ataxia and retinitis pigmentosa (NARP), as well as maternally-inherited Leigh syndrome (MILS) are moreover commonly resulting from a T8993G point mutation in the ATP synthase 6 gene in mtDNA. MELAS (Mitochondrial Encephalomyopathy; Lactic Acidosis; Stroke) is caused by mutations in a variety of mitochondrial genes, but usually in $tRNA_{Leu}$, with an A3243G mutation responsible for 80% of MELAS syndromes. MERRF (Myoclonic Epilepsy; Ragged Red Fibers) is commonly associated with a mutation in mitochondrial $tRNA_{Lys}$; Cardiomyopathy is often associated with mutations in $tRNA_{Ile}$; myopathy, deafness and diabetes can also all have mitochondrial associations.

There are still considerable uncertainties about how mtDNA is replicated, maintained and expressed. The ability to manipulate or modify particular mtDNA sequences in mitochondria within cells would facilitate investigations of normal mtDNA processes and also enable development of therapies for diseases resulting from alteration of sequences in mitochondrial DNA. However achieving this goal has proven difficult as standard gene therapy approaches such as delivering exogenous copies of DNA into mitochondria in a heritable manner remains problematic.

Although the mitochondrion comprises its own genome, it imports a large number of proteins (estimated at about 1000) which are produced on cytoplasmic ribosomes and encoded in nuclear genes. Nuclear proteins intended for import into mitochondria have signal sequences that relocate the polypeptides to the relevant organelle; these are known as mitochondrial targeting sequences (MTS).

Tanaka et al. (2002) J Biomed Sci 9:534-541 reported the delivery of a SmaI endonuclease to mitochondria by fusing it to the cytochrome c oxidase subunit IV MTS. SmaI cleaves the sequence CCC//GGG, which occurs in mtDNA as a result of a T8993G mutation, for example in NARP or MILS. The mutant mitochondrial DNA was cleaved by the restriction enzyme. Since mutant mitochondrial DNA typically coexists with wild-type mtDNA (a phenomenon known as heteroplasmy, resulting from the maternal inheritance of a plurality of mitochondria through the ovum), destruction of mutant DNA allows mitochondria comprising wild-type DNA to become dominant in the cell, and the disease condition can be reversed. However, because the specificities of naturally occurring restriction enzymes are limited in numbers, this approach is of limited application to the mutations that can be connected.

In order to overcome such problems outside of mitochondria, fusions between the DNA-cleaving domains of restriction endonucleases and DNA-binding domains have been made. A method of converting zinc finger DNA binding domains to chimaeric restriction endonucleases has been described in Kim, et al., (1996) Proc. Natl. Acad. Sci. USA 93:1156-1160.

MTSs are known in the art and are reviewed, for example, in Pfanner & Geissler, Nature Reviews Mol Cell Biol 2:339-49, incorporated herein by reference.

US patent application US2004/0072774 describes the use of MTS to transfer polypeptides synthesised in the cytoplasm to the mitochondrion. Examples of MTS given in US2004/0072774 include the N-terminal region of human cytochrome c oxidase subunit VIII, the N-terminal region of the P1 isoform of subunit c of human ATP synthase, and the N-terminal region of the aldehyde dehydrogenase targeting sequence.

However, US2004/0072774 is concerned with the delivery of polypeptides other than DNA-binding polypeptides. For example, US2004/0072774 suggests that mitochondrial disorders may be corrected by introducing a native mitochondrial polypeptide with the wild type sequence.

DNA binding proteins have been used to modulate gene expression in the nucleus of cells. Recombinant ZFPs have been reported to have the ability to regulate gene expression of transiently expressed reporter genes in cultured cells (see, e.g., Pomerantz et al., Science 267:93-96 (1995); Liu et al., PNAS 94:5525-5530 1997); and Beerli et al., PNAS 95:14628-14633 (1998)) and exogenous chromosomal sequences (Choo et al., Nature 372:642-645 (1994)).

More recent work shows the use of ZFP fusions to transcriptional activation and repression domains to regulate expression of endogenous chromosomal genes in their native state in cultured cells [Beerli et al. (2000) PNAS 97:1495-1500; Zhang et al. (2000) J. Biological Chemistry 275:33850-33860; Liu et al. (2001) J. Biological Chemistry 276:11323-11334] and in whole animals [Rebar et al. (2002) Nature Medicine 8:1427-1432; Dai et al. (2004) Circulation 110:2467-2475].

In particular, Beerli et al. targeted endogenous erbB-2 and erbB-3 genes using zinc finger polypeptides produced by rational design. Using KRAB and VP64 repression and activation domains fused to the ZFPs, Beerli et al. were able to observe upregulation and downregulation of expression in endogenous erbB-2 and erbB-3 genes. Zhang et al. activated the endogenous erythropoietin gene using a ZFP linked to the VP16 transactivation domain. ZFPs were obtained by rational design and tested to determine their ability to transactivate endogenous and transfected EPO genes. ZFPs with a dissociation constant of <10 nM were found to be effective in activating transfected epo templates; a subset of these was effective in transactivating the endogenous gene. Liu et al. used ZFPs targeted to open chromatin regions in the VEGF-A gene, mapped by DNase I hypersensitivity analysis, to regulate the endogenous VEGF-A gene. Rebar et al. and Dai et al. targeted the endogenous VEGF-A gene to induce angiogenesis in a mouse model and in rabbits respectively.

ZFP fusions to the Type IIS restriction enzyme cleavage domain from FokI have been used to catalyze cleavage of chromosomal DNA at a predetermined site, promoting both targeted mutagenesis [Bibikova et al. (2002) Genetics 161: 1169-1175; Lloyd et al. (2005) PNAS 102:2232-2237] and targeted homologous recombination [Porteus and Baltimore (2003) Science 300:763; Bibikova et al. (2003) Science 300:764; Urnov et al (2005) Nature 435:646-651].

Lloyd et al. used ZFPs to induce targeted mutagenesis in plant genes. In this procedure, ZFNs were used to generate double-strand breaks at specific genomic sites. Subsequent repair by non-homologous end joining (NHEJ) is known to be error-prone in plants and produces mutations at the break site. Constructs carrying both a ZFN gene, driven by a heat-shock promoter, and its target were introduced into the *Arabidopsis* genome. Induction of ZFN expression by heat shock during seedling development resulted in mutations at the ZFN recognition sequence at frequencies as high as 0.2 mutations per target. Of 106 ZFN-induced mutations characterized, 83 (78%) were simple deletions of 1-52 bp (median of 4 bp), 14 (13%) were simple insertions of 1-4 bp, and 9 (8%) were deletions accompanied by insertions.

Porteus and Baltimore were able to demonstrate correction of a gene defect in an exogenous integrated chromosomal GFP gene in human cells, using a ZFP-FokI fusion. Bibikova et al. showed targeted recombination, mediated by a ZFP-FokI fusion, at the yellow locus in *Drosophila* embryos. Urnov et al. used ZFP-FokI fusion proteins to obtain targeted recombination at the endogenous IL-2Rgamma locus, in human cells, at frequencies approaching 20%. Without the ZFP fusion, targeted recombination occurs at a frequency of approximately 1-2 cells in 500,000.

None of the above constructs, however, has been used in a mitochondrion. There is therefore a need to establish whether DNA-binding proteins, such as ZFPs, can be used in mitochondria; and if so, how such proteins may be targeted to the mitochondrion.

SUMMARY OF THE INVENTION

The present inventors have discovered that it is not possible to target every desired polypeptide to the mitochondrion simply by fusing it with a mitochondrial targeting sequence (MTS). Many polypeptides, including DNA-binding polypeptides such as transcription factors, appear to be strongly biased towards nuclear localisation, as befits their normal role in cellular processes. It appears that the use of an MTS is not sufficient for the delivery of DNA-binding polypeptides heterologous to the mitochondrial environment.

The present invention provides methods and compositions for the delivery to the mitochondrion of DNA-binding polypeptides. Moreover, the present invention provides for the use of DNA binding proteins heterologous to the mitochondrion within the mitochondrial matrix.

In a first aspect, therefore, there is provided a nucleic acid construct comprising a coding sequence encoding a DNA-binding polypeptide, fused to a mitochondrial targeting sequence (MTS) and a nuclear export signal (NES).

Preferably, the DNA-binding protein is fused with an effector molecule (i.e., a functional domain), such as a transcriptional activation or repression domain, a restriction enzyme or other DNA-modifying enzyme, which can be employed to modify the mitochondrial genome.

Preferably, the functional domain is a DNA-cleavage domain of a restriction endonuclease. Type IIs restriction endonucleases typically possess separable DNA binding and cleavage domains; hence, the cleavage domains may be harnessed to an alternative DNA binding protein to produce an artificial restriction enzyme capable of cleaving mtDNA at any desired position, and with a specificity which may be tailored to any target sequence. Preferably, therefore, the restriction endonuclease is a Type IIs restriction endonuclease. Examples of Type IIs restriction endonucleases include FokI, BpmI, BsgI and MboII.

Alternative effector molecules and functional domains may be employed, including transcription activation and repression domains, to modify transcription of mtDNA genes.

Advantageously, the sequence to which the DNA binding proteins binds (the "target sequence") is a unique site in the mitochondrial genome. This site is preferably associated with a mitochondrial disorder or a genetic disease, meaning that it is at or near the site of a mutation that occurs in the disorder or disease. In such a manner, only mitochondrial genomes that are affected by a mutation associated with a disease are influenced by the polypeptides of the invention. For example, the site may be the site of a point mutation that is associated with a disease, as described above.

Where the effector molecule is a restriction enzyme, the unique site preferably does not occur in wild type mitochondria. In this way, the genomes of mitochondria harbouring a mutation can be selectively inactivated.

However, if the functional domain is a transcriptional modulation domain, the site may occur in the wild-type mitochondrial genome, but preferably at locations where binding of the fusion polypeptide will not affect gene expression.

By "associated with" the mitochondrial disorder or genetic disease, it is intended to indicate that the site of binding of the nucleic acid binding protein either occurs only in mitochondrial genomes which are responsible for the disorder or disease, usually as a result of a mutation, or that the site is a location responsible for the regulation of a gene associated with a mitochondrial disorder or genetic disease.

The nucleic acid according to the invention can be present in a vector capable of expression in a eukaryotic cell, and containing the necessary regulatory sequences to ensure transcription and translation of the nucleic acid. The vector may be transiently expressed in the eukaryotic cell, or may be stably expressed. The use of viral vectors, such as adenoviral vectors, retroviral vectors, cytomegalovirus vectors, vaccinia and other poxviruses, including mutants such as MVA, lentiviral vectors and adeno-associated viral vectors, is known in the art and is an effective means of transformation of eukaryotic cells in vivo.

Advantageously, the DNA binding polypeptide is heterologous to the mitochondrion. Proteins that are not native to the mitochondrial environment are expected to be more difficult to deliver to mitochondria; the method of the invention is particularly advantageous for the delivery of such polypeptides.

Preferably, the DNA binding proteins useful in the invention are derived from transcription factors, especially the DNA binding domains of transcription factors. Particularly preferred DNA binding proteins are zinc finger polypeptides.

DNA binding proteins may be natural proteins or may be selected from libraries, optionally libraries of randomised or partially randomised polypeptides as described further herein. Moreover, DNA binding proteins and especially ZFPs may be designed rationally, using established principles.

Vectors according to the invention can be used for delivery of DNA binding polypeptides to the matrix of the mitochondrion. Such polypeptides may be used for the modification of mitochondrial DNA, the regulation of mitochondrial gene expression, or other desired purposes.

In a further aspect, there is provided a eukaryotic cell transformed with a nucleic acid construct according to the first aspect of the invention. Also provided are cells comprising a protein encoded by a nucleic acid construct of the invention.

In a further aspect of the invention, there is provided a fusion protein comprising:
   (a) a DNA-binding polypeptide which binds to a specific site (i.e., a target sequence) in mtDNA;
   (b) an effector molecule or functional domain;
   (c) a mitochondrial targeting sequence (MTS); and
   (d) a nuclear export sequence (NES).

Preferably, the fusion protein according to the invention possesses attributes and features as described in the foregoing aspects. Advantageously, the fusion protein binds to and modifies mtDNA in a site-specific manner. In a particularly preferred embodiment, the fusion protein is capable of recognising and destroying a defined mtDNA molecule.

The invention moreover provides a pharmaceutical composition comprising a nucleic acid vector in accordance with the foregoing aspects of the invention. The pharmaceutical composition comprises the nucleic acid construct in a form suitable for administration to an organism by injection or otherwise. Viral vectors can be used for transduction of cells in multicellular organisms. Pharmaceutical compositions according to the invention are useful in a method for treating a disease involving an mitochondrial abnormality, comprising administering to a subject in need thereof a composition comprising a nucleic acid construct according to the invention.

Also provided is the use of a nucleic acid construct as herein described in the preparation of a pharmaceutical composition for the treatment of a mitochondrial disease.

In a still further aspect, there is provided a method for delivering a polypeptide to a mitochondrion, comprising the steps of:
   (a) preparing a nucleic acid construct according to the first aspect of the invention; and
   (b) introducing the nucleic acid construct into a eukaryotic cell;
such that the construct is expressed to produce the polypeptide and the polypeptide enters the mitochondrion.

In a further aspect, the invention provides the use of a DNA binding protein heterologous to the mitochondrion within the mitochondrial matrix. The present inventors have found that DNA binding proteins which are of nuclear origin, such as ZFPs, retain their DNA-binding activity in mitochondria. Accordingly, there is provided a method for modulating gene expression in a mitochondrion, comprising delivering to said mitochondrion a DNA-binding protein heterologous to the mitochondrion. Preferably, the DNA binding protein is a ZFP.

Figure 1:
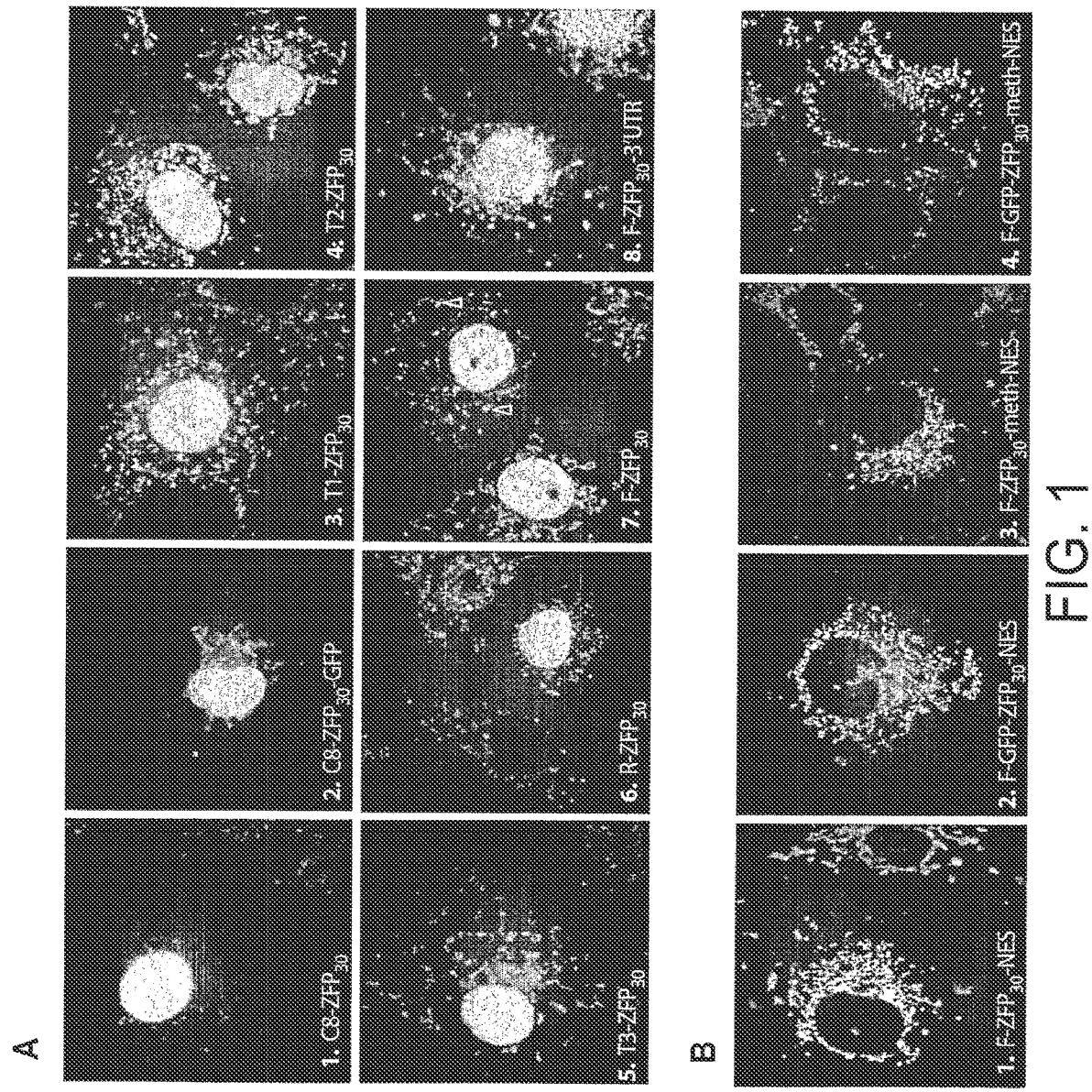
FIG. 1

Effects of different mitochondrial targeting sequences (MTSs) and additional sequences on intracellular localisation of ZFPs Intracellular localisation of constructs derived from ZFP clone 30 (ZFP30) was analysed by immunofluorescence in transiently transfected COS-7 cells, where mitochondria were stained with Mitotracker CMX Red and ZFPs detected with antibodies against epitope-tags followed by secondary antibodies conjugated to FITC.

(A) shows merged localisation images of red (MitoTracker derived) and green fluorescence derived from ZFP30 that was initially tested in a context of different MTSs and with or without additional sequences such as C-terminal GFP (2) or 3'UTR (8). The following N-terminal MTSs from endogenous mitochondrial proteins were tested: C8—from the subunit VIII of the human cytochrome c oxidase (1 and 2), T1—from the zinc finger protein MP42 from *Tryphanosoma brucei* (3), T2—from the zinc finger protein MP63 from *T. brucei* (4), T3—from the zinc finger 7b protein from *Leishmania tarentolae* (5), R—from the subunit 6 of ATP synthase from *Chlamydomonas reinhardtii*

(6) and F—from the human F1βsubunit of ATP synthase (7 and 8). The F-ZFP30 (7) was the only construct exhibiting partial mitochondrial localisation (7 arrowed) therefore it was used to engineer a family of constructs containing NES (panel B).

(B) shows merged localisation images of red (MitoTracker derived) and green fluorescence derived from F-ZFP30 containing NES (1) with or without additional domains. The fusion proteins tested include: F-GFP-ZFP30-NES incorporating GFP to form a product of size 48 kDa (2), F-ZFP30-meth-NES incorporating the catalytic domain of the hDNMT3a methylase which results in a product of 61 kDa (3) and F-GFP-ZFP30-meth-NES incorporating both GFP and the catalytic methylase domain of the hDNMT3a to give a fusion protein of 86 kDa (4). Colocalisation of ZFP30 with Mitotracker appears yellow on digitally merged images.

FIG. 2

Design and DNA-binding of the NARP-specific mitochondrial F-ZFPNARP (A) DNA recognition by a 3-finger protein F-ZFPNARP. A Zif268-based F-ZFPNARP has been selected to bind a sequence containing the T8993G mutation in the L-strand of mtDNA (the 8993G is marked as a black box in a target site). The amino acid sequences of the α-helices of zinc fingers F1 (SEQ ID NO: 65), F2 (SEQ ID NO: 35) and F3 (SEQ ID NO: 66) are listed below using a single letter code. The fingers F1, F2 and F3 are represented by α-helix and two β-strands stabilised by a zinc ion depicted as a grey sphere. Predicted contacts by residues in positions −1, 3 and 6 with the L-strand of mtDNA are shown as solid black arrows. The curved grey arrows indicate possible cross-strand interactions between the amino acid in position 2 and the complementary H-strand at the interface between adjacent 3 bp binding sites for each finger.

(B) Sequence discrimination by F-ZFPNARP. In vitro synthesized F-ZFPNARP and a control zinc finger peptide F-ZFPcont were tested in the gel retardation assays for their binding to the target DNA, which contained either the mutant T8993G (NARP-G) or T8993C (NARP-C) or the wt sequence 8993T (wt). All the peptides were used in successive 5-fold dilutions (marked as gradient symbols) and DNA probes were used at a concentration of 0.3 nM. The letter "f" denotes free DNA while "b" denotes protein-bound complexes. Two mobility forms of protein bound complexes "b" can be attributed to two different degrees of compaction of F-ZFPNARP-DNA, occurring in the presence or absence of a cross-strand interaction. It has to be noted that F-ZFPNARP has not been optimised for these interactions.

(C) F-ZFPNARP retains its binding ability upon import to mitochondria. Gel retardation assay on the DNA target containing the T8993G mutation (NARP-G) was performed on the mitochondrial extract from the cells transiently expressing mitochondrially targeted F-ZFPNARP. The cytosolic fraction was used as a control. Sequential dilutions of the proteins and concentration of the probe were as in (B).

FIG. 3

Construction and intramitochondrial localisation of mitochondrially targeted 10 zinc finger methylase F-ZFPNARP-meth-NES.

(A) Schematic structure of mitochondrially targeted methylases. In order to construct a NARP specific (F-ZFPNARP-meth-NES) or a control (F-ZFPcont-meth-NES) chimaeric methylases F-ZFPNARP or F-ZFPcont was linked using a 17 amino acid long flexible linker of (SGGGG)3SS (SEQ ID NO: 24) to a catalytic domain (residues 592-909) of the human DNMT3a DNA methylase (hDNMT3a CD). The nuclear export signal (NES) was added to the C-terminus. As an additional control the mitochondrially targeted methylase lacking the DNA binding domain was constructed (F-meth-NES) by deleting ZFP from the F-ZFPNARP-meth-NES construct. Both constructs use the HA epitope tag to facilitate further detection.

(B) Localisation of the F-ZFPNARP-meth-NES zinc finger methylase inside mitochondria. The NARP cells transiently overexpressing F-ZFPNARP-meth-NES were fractionated and the protein fractions were analysed by western blotting using anti-HA mAb. The localisation of the F-ZFPNARP-meth-NES precursor ("p") and its mature ("m") form in total cell lysate ("T"), cytosolic ("C") and a mitochondrial fraction treated with Proteinase K under various conditions as indicated, was compared with the localisation of marker proteins. The precursor of F-ZFPNARP-meth-NES was found in the mitochondrial fraction, however was clearly located outside the mitochondria, since it was accessible to protease digestion. On contrary the mature form of the chimaeric methylase was protected and became accessible to proteolysis only after the mitochondria were lysed with Triton X-100. The following endogenous proteins were used as fractionation markers: (i) GAPDH previously reported as electrostatically associated with mitochondrial outer membrane 25, 26. (ii) mtTFAM—the transcription factor that is localised in the mitochondrial matrix 27.

(C) Colocalisation of the F-ZFPNARP-meth-NES zinc finger methylase with mitochondrial nucleoid. Intracellular localisation of F-ZFPNARP-meth-NES was analysed by immunofluoresce in transiently transfected NARP cells. Mitochondria were stained with MitoTracker CMX Red (red) and F-ZFPNARP-meth-NES was detected with antibodies against the HA epitope-tag followed by secondary antibodies conjugated to FITC (green). The F-ZFPNARP-meth-NES exhibits a punctate intramitochondrial staining pattern (1-3). Moreover, the majority of transiently expressed F-ZFPNARP-meth-NES colocalised with mtTFAM, a well-known protein of human mitochondrial nucleoid, stained with polyclonal antibodies and visualised with TexasRed (4-6). Intramitochondrial foci that were positive for F-ZFPNARP-meth-NES colocalised with mtDNA labelled with BrdU (7-9).

FIG. 4

Result of in vivo methylation of the mtDNA region adjacent to the ZFPNARP binding site In order to determine the methylation status of cytosine residues in the H-strand of mtDNA surrounding the NARP mutation site for each indicated construct, total cellular DNA was subjected to bisulphite conversion. Then the region of interest (positions 8950-9070 as indicated) was amplified by PCR and cloned into E. coli. For each construct a statistically significant number of independent clones (indicated by "N=") was randomly selected, sequenced and analysed in order to identify which cytosine had been methylated. The diagrams represent the mtDNA fragments originated from either the NARP cells or control wt cells, where unmethylated CpN dinucleotides are represented as open squares and the methylated CpN sites (mCpN) are depicted as filled squares and are coloured according to the legend. The numbers inside the filled squares represent the frequency of mCpN detected for each construct. The CpG sites found in the analysed region are additionally alphabetically denoted from "a" to "f" for reference in the text. For each construct the percentage of clones containing at least one mCpN, mCpG or methylated non-CpG is presented on the graph. The statistical difference in methylation of DNA originated from the NARP cells expressing F-ZFP- NARP-meth-NES and the controls was found to be highly significant (P>0.001), as determined by a paired Student t test.

FIG. 5

Sequences of zinc finger proteins tested for mitochondrial import.

Protein sequences of the library of closely related four-finger proteins engineered as two times two-finger units (2F×2F) are aligned. The proteins have been tested for their ability to be imported into mitochondria with the aid of various MTSs. The predicted DNA-contacting residues in the α-helices are marked in yellow. The positions in the recognition α-helices for zinc finger F1 to F4 are indicated above the alignment. A linker (sequence GGG) present between first and second set of two fingers is in blue where applicable. Substitutions, outside of the recognition α-helices are marked in black. Sets of basic amino acids within the recognition α-helix of finger F2 and F4, which could serve as a potential NLS, are framed. The proteins of Group 1 (SEQ ID NOS 67-83, respectively, in order of appearance) and Group 2 (SEQ ID NOS 84-87, respectively, in order of appearance) were assembled from different libraries.

FIG. 6

Colocalisation of F-ZFP$_{NARP}$-meth-NES with mtDNA stained with PicoGreen dye.

Colocalisation of F-ZFP$_{NARP}$-meth-NES with mtDNA was analysed by immunofluorescence in transiently transfected NARP cells. The PicoGreen stained cells were fixed, permeabilised and subjected to immunostaining as described in the Experimental Procedures. The chimaeric methylase was detected with antibodies against the HA epitope-tag followed by secondary antibodies conjugated to Texas Red (red). Colocalisation appears as yellow on the digitally overlaid picture.

FIG. 7

Illustration of the bisulphite method used to analyse $^5$C methylation

The DNA sequence of the mitochondrial H-strand of the region adjacent to the ZFP$_{NARP}$ binding site in mtDNA of the NARP cells (from 8950 bp to 9030 bp) is shown to exemplify the method. The sequence of the ZFP$_{NARP}$ binding site is highlighted. (A) The methylation DNA template (SEQ ID NO: 88) before bisulphite conversion. (B) The unmethylated DNA template (SEQ ID NO: 89) after bisulphite treatment. Note that all cytosines are converted to thymines. (C) The DNA template (SEQ ID NO: 90) treated with CpG methylase M.SssI in vitro and further subjected to bisulphite conversion. (D) and (E) Two examples of the in vivo methylated DNA template (SEQ ID NOS 91-92, respectively, in order of appearance) after bisulphite conversion of different clones. Unconverted cytosines arising from DNA methylation in CpG context are underlined.

FIG. 8

Result of methylation of the mtDNA regions distant from the ZFP$_{NARP}$ binding site In order to determine the methylation status of cytosine residues in the H-strand of mtDNA distant from the NARP mutation site for indicated constructs total cellular DNA was subjected to bisulphite conversion. Then the control regions of rntDNA (positions 380 to 570 and 13500 to 13650) were amplified by PCR and cloned into *E. coli*. For each construct a statistically significant number of independent clones (indicated by "N=") was randomly collected, sequenced and analysed in order to identify which cytosine had been methylated. The diagrams represent the mtDNA fragments originated from the NARP cells, where unmethylated CpN dinucleotides are represented as open squares and the methylated CpN sites (mCpN) are depicted as filled squares and are coloured according to the legend. The numbers inside the filled squares represent the frequency of mCpN detected for each construct. For each construct the percentage of clones containing at least one mCpN, mCpG or methylated non-CpG is presented on the graph.

DETAILED DESCRIPTION OF THE INVENTION

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 3rd ed. (2001) Cold Spring Harbor Laboratory Press, Cold Spring Harbor, N.Y. and Ausubel et al., Short Protocols in Molecular Biology (1999) 4$^{th}$ Ed (and periodic supplements), John Wiley & Sons, Inc. which are incorporated herein by reference), chemical methods, pharmaceutical formulations and delivery to and treatment of patients.

A. DNA Binding Polypeptides

The term 'DNA binding polypeptide' includes any polypeptide which is capable of binding or associating with a nucleic acid. This binding or association may be via any type of reversible or irreversible association. The term "DNA binding polypeptide" is used extensively herein. However other types of nucleic acids other than DNA may be relevant. Consequently, it is intended that in general the above term can be replaced with the term "nucleic acid binding molecule". Nucleic acids will in general be RNA or DNA, double stranded or single stranded. However, in a preferred aspect of the invention, references to "DNA" mean deoxyribonucleic acid in a literal sense and particularly to mitochondrial (mt) DNA, which is the target for DNA binding proteins according to the invention. The polypeptides may moreover target mitochondrial RNA.

The DNA binding polypeptides of the invention are preferably heterologous to the mitochondrion. This means that they are not mitochondrial proteins, either encoded in the nucleus and exported to the mitochondrion from the cytoplasm or encoded in the mitochondrial genome, in wild type form.

Polypeptides according to the invention can include polypeptides displayed on the surface of bacteriophage particles. Polypeptides according to the invention can also include libraries of polypeptides presented as integral parts of the envelope proteins on the outer surface of bacteriophage particles. Methods for the production of libraries encoding randomised polypeptides are known in the art and may be applied in the present invention. See, for example, WO 96/06166; WO 98/53057; WO 00/42219 and WO 01/40798. Randomisation may be total, or partial; in the case of partial randomisation, the selected codons preferably encode options for amino acids, and not for stop codons.

Alternative methods for selecting polypeptides from libraries include two hybrid selection and bacterial display. Two Hybrid selection of zinc fingers has been described by Joung et al. 97 (13): 7382. (2000). This system is a modification of the screen described by Hu, J. C., Kornacker, M. G. & Hochschild, A. (2000) Methods 20, 80-94; Dove, S. L., Joung, J. K. & Hochschild, A. (1997) Nature (London) 386, 627-630; and Dove, S. L. & Hochschild, A. (1998) Genes Dev. 12, 745-754. In that screen, as in the yeast two-hybrid system, there are two fusion proteins that interact in a way that leads to transcriptional activation of a lacZ-reporter gene. One protein is composed of a DNA-binding domain (DBD) fused to another domain (X). The second protein contains a further domain (Y) fused to a subunit of the *E. coli* RNA polymerase. In this arrangement, activation of lacZ expression requires appropriate protein-DNA and protein-protein interactions: The DBD must bind to a DNA-binding site (DBS) positioned near the promoter, and domain X must simultaneously interact with domain Y to recruit RNA polymerase to the promoter, thereby activating transcription. The major advantage of this system is that almost any protein-DNA (DBD-DBS) or protein-protein (X-Y) interaction should mediate transcriptional activation. However, because lacZ is used as a reporter gene in this system, candidates must be identified by a visual phenotype (e.g., their blue color on 5-bromo-4-chloro-3-indolyl b-D-galactoside plates). Thus, the system (in this form) cannot readily be used to screen libraries larger than $10^5$-$10^6$ in size. To improve this previously described system so that it can be used to analyze libraries larger than $10^8$ in size, Joung et al. replaced the lacZ gene with the selectable yeast HIS3 gene.

DNA binding polypeptides are, or are derived from, DNA binding proteins such as DNA repair enzymes, polymerases, recombinases, methylases, restriction enzymes, replication factors, histones, or DNA binding structural proteins such as chromosomal scaffold proteins; preferably said polypeptides are derived from transcription factors. 'Derived from' means that the DNA binding polypeptides preferably comprise one or more of: transcription factors, fragment(s) of transcription factors, sequences homologous to transcription factors, or polypeptides which have been fully or partially randomised from a starting sequence which is a transcription factor, a fragment of a transcription factor, or homologous to a transcription factor. Most preferably, DNA binding polypeptides comprise polypeptides which are at least 40% homologous, more preferably at least 60% homologous, even more preferably at least 75% homologous or even more, for example 85%; or 90%, or even more than 95% homologous to one or more transcription factors, using one of the homology calculation algorithms defined below.

DNA binding polypeptides may comprise, among other things, DNA binding part(s) of any protein(s), for example zinc finger transcription factors, Zif268, ATF family transcription factors, ATF1, ATF2, bZIP proteins, CHOP, NF-κB, TATA binding protein (TBP), MDM, c-jun, elk, serum response factor (SRF), ternary complex factor (TCF); KRUPPEL, Odd Skipped, even skipped and other *D. melanogaster* transcription factors; yeast transcription factors such as GCN4, the GAL family of galactose-inducible transcription factors; bacterial transcription factors or repressors such as lacI$^q$, or fragments or derivatives thereof. Derivatives would be considered by a person skilled in the art to be functionally and/or structurally related to the molecule(s) from which they are derived, for example through sequence homology of at least 40% or any integral value thereover.

The DNA binding polypeptides may be non-randomised polypeptides, for example 'wild-type' or allelic variants of naturally occurring polypeptides, or may be non-naturally-occurring combinations of naturally-occurring polypeptides covalently joined to one another, or may be specific mutant (s), or may be wholly or partially randomised polypeptides, preferably structurally related to DNA binding proteins as described herein.

These DNA binding polypeptides can be displayed on the surface of bacteriophage particles and, in certain embodiments, are partially randomised zinc-finger type transcription factors, preferably retaining at least 40% homology (as described herein) to zinc-finger type transcription factors.

In some cases, sequence homology may be considered in relation to structurally important residues, or those residues which are known or suspected of being evolutionarily conserved. In such instances, residues known to be variable or non-essential for a particular structural conformation may be discounted from the homology calculation. For example, as explained herein, zinc fingers are known to have certain residues which are important for the formation of the three-dimensional zinc finger structure. In these cases, homology may be considered over about seven of said important amino acid residues amongst approximately thirty residues which may comprise the whole finger structure.

As used herein, the term homology may refer to structural homology. Structural homology may be estimated by comparing the structural RMS deviation of the main part of the carbon atom backbone of two or more molecules. Preferably, the molecules may be considered structurally homologous if the deviation is 5 Å or less, preferably 3 Å or less, more preferably 1.5 Å or less. Structurally homologous molecules will not necessarily show significant sequence homology.

DNA binding polypeptides, as defined above, may be prescreened prior to being tested in the methods of the intervention using routine assays known in art for determining the binding of molecules to nucleic acids so as to eliminate molecules that do not bind DNA. For example, a DNA binding polypeptide, or a library of DNA binding polypeptides, is contacted with a nucleic acid and binding is determined. The nucleic acid may for example be labelled with a detectable label, such as a fluorophore/fluorochrome, such that after a wash step binding can be determined easily, for example by monitoring fluorescence.

The nucleic acid with which the binding polypeptides are contacted may be non-specific nucleic acids, such as a random oligonucleotide library or sonicated genomic DNA and the like. Alternatively, a specific sequence may be used or a partially randomised library of sequences.

The invention provides both DNA binding polypeptides and nucleic acid sequences which encode the polypeptides of the invention. Fragments, mutants, alleles and other derivatives of the nucleic acids and polypeptides of the invention preferably retain substantial homology with said sequence(s), as described above. As used herein, "homology" means that the two entities share sufficient characteristics for the skilled person to determine that they are similar. Preferably, homology is used to refer to sequence identity. Thus, the derivatives of said DNA binding polypeptides of the invention preferably retain substantial sequence identity with said molecules.

In the context of the present invention, a homologous sequence is taken to include any sequence which is at least 60, 70, 80 or 90% identical (or any integral value therebetween), preferably at least 95 or 98% identical over at least 5, preferably 8, 10, 15, 20, 30, 40 or even more residues or bases with the molecules (i.e. the sequences thereof) of the invention, for example as shown in the sequence listing herein. In particular, homology should typically be considered with respect to those regions of the molecule(s) which may be known to be functionally important rather than non-essential neighbouring sequences. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate percent homology between two or more sequences.

Percent homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum percent homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

DNA binding polypeptides according to the invention may include any atom, ion, molecule, macromolecule (for example polypeptide), or combination of such entities that are capable of binding to nucleic acids, such as DNA. Advantageously, molecules according to the invention may include families of polypeptides with known or suspected nucleic acid binding motifs. These may include for example zinc finger proteins (see below). Molecules according to the invention may also include helix-turn-helix proteins, homeodomains, leucine zipper proteins, helix-loop-helix proteins or β-sheet motifs which are known to a person skilled in the art.

According to the invention, DNA binding motifs of one or more known or suspected nucleic acid binding polypeptide (s) may advantageously be randomised, in order to provide libraries of nucleic acid binding molecules.

Crystal structures may advantageously be used in selecting or predicting the relevant DNA binding regions of nucleic acid binding proteins by methods known in the art.

DNA binding regions of proteins within the same structural family are often conserved or homologous to one another, for example zinc finger α-helices, the leucine zipper basic region, homeodomain helix 3.

Other families of transcription factors, for example from the helix-turn-helix (HTH) family and/or from the probe helix (PH) family, the C4 Zinc-binding family (which includes the hormone receptor (HR) family), the Gal4 family, the c-myb family, other zinc finger families, or any other family of DNA binding proteins known to one skilled in the art, may be used in the context of the invention.

One or more polypeptides from one or more of these families could be advantageously randomised to provide a library of molecules for use in the invention. Preferably, the amino acid residues known to be important for nucleic acid binding could be randomised. However it may be desirable to randomise other regions of the DNA binding polypeptide since alterations to the amino acid sequence outside of those elements of secondary structure that present amino acids that contact the DNA are likely to cause conformational changes that may affect the DNA binding properties of the molecule.

For example, randomisation may involve alteration of zinc finger polypeptides, said alteration being accomplished at the DNA or protein level. Mutagenesis and screening of zinc finger polypeptides may be achieved by any suitable means. Preferably, the mutagenesis is performed at the nucleic acid level, for example by synthesising novel genes encoding mutant polypeptides and expressing these to obtain a variety of different proteins. Alternatively, existing genes can themselves be mutated, such as by site-directed or random mutagenesis, in order to obtain the desired mutant genes. A further option is to generate random arrangements of naturally-occurring DNA-binding domains, such as individual zinc fingers, in a single polypeptide.

Mutations may be performed by any method known to those of skill in the art. Preferred, however, is site-directed mutagenesis of a nucleic acid sequence encoding the protein of interest. A number of methods for site-directed mutagenesis are known in the art, from methods employing single-stranded phage such as M13 to PCR-based techniques (see "PCR Protocols: A guide to methods and applications", M. A., Innis, D. H. Gelfand, J. J. Sninsky, T. J. White (eds.).

Academic Press, New York, 1990). Preferably, the commercially available Altered Site II Mutagenesis System (Promega) may be employed, according to the manufacturer's instructions.

Randomisation of the zinc finger binding motifs is preferably directed to those amino acid residues where the code provided herein gives a choice of residues (see below). For example, positions +1, +5 and +8 are advantageously randomised, whilst preferably avoiding hydrophobic amino acids; positions involved in binding to the nucleic acid, notably −1, +2, +3 and +6, may be randomised also, preferably within the choices provided by the rules referred to below.

Screening of the proteins produced by mutant genes is preferably performed by expressing the genes and assaying the binding ability of the protein product. A simple and advantageously rapid method by which this may be accomplished is by phage display, in which the mutant polypeptides are expressed as fusion proteins with the coat proteins of filamentous bacteriophage, such as the minor coat protein pII of bacteriophage, m13 or gene III of bacteriophage Fd, and displayed on the capsid of bacteriophage transformed with the mutant genes. The target nucleic acid sequence is used as a probe to bind directly to the protein on the phage surface and select the phage possessing advantageous mutants, by affinity purification. The phage are then amplified by passage through a bacterial host, and subjected to further rounds of selection and amplification in order to enrich the mutant pool for the desired phage and eventually isolate the preferred clone(s). Detailed methodology for phage display is known in the art and set forth, for example, in U.S. Pat. No. 5,223,409; Choo and Klug, (1995) Current Opinions in Biotechnology 6:431-436; Smith, (1985) Science 228:1315-1317; and McCafferty et al., (1990) Nature 348:552-554; all incorporated herein by reference. Vector systems and kits for phage display are available commercially, for example from Pharmacia.

Specific peptide ligands such as zinc finger polypeptides may moreover be selected for binding to targets by affinity selection using large libraries of peptides linked to the C-terminus of the lac repressor LacI (Cull et al., (1992) Proc Natl Acad Sci USA, 89, 1865-9). When expressed in *E. coli* the repressor protein physically links the ligand to the encoding plasmid by binding to a lac operator sequence on the plasmid.

An entirely in vitro polysome display system has also been reported (Mattheakis et al., (1994) Proc Natl Acad Sci USA, 91, 9022-6) in which nascent peptides are physically attached via the ribosome to the RNA which encodes them. See also U.S. Pat. No. 6,733,970.

Additional in vitro selection methods are described in WO 98/37186, WO 2004/22746 and GB 2,338,237.

A two-hybrid selection method is disclosed in WO 01/88197.

Furthermore, polypeptides may be partitioned in physical compartments for example wells of an in vitro dish, or subcellular compartments, or in small fluid particles or droplets such as emulsions; further teachings on this topic may be found in Griffiths et al. (see WO 99/02671) and Choo et al. (WO 02718648).

A library for use in the invention may be randomised at those positions for which choices are given in the rules referenced below. These rules allow the person of ordinary skill in the art to make informed choices concerning the desired codon usage at the given positions.

The recognition helix of PH family polypeptides contains conserved Arg/Lys residues which are important structural elements involved in the binding of phosphates in the nucleic acid. Base specificity is attributed to amino acids 1, 4, 5 and 8 of the helix. These residues could be advantageously varied, for example amino acid 1 could be selected from Asn, Asp, His, Val, Ile to provide the possibility of binding to A, C, G, or T. Similarly, amino acid 4 could be selected from Asn, Asp, His, Val, Ile, Gln, Glu, Arg, Lys, Met, or Leu to provide the possibility of binding to A, C, G or T. Preferably, the rules laid out in (Suzuki et al., 1994: PNAS vol 91 pp 12357-61) would be used in order to randomise those amino acids which affect interaction of the molecule with the nucleic acid, whether in a base specific manner, or via binding to the phosphate backbone, thereby producing a library of nucleic acid binding molecules for use in the methods of the invention.

Similarly, polypeptide molecules of the helix-turn-helix (HTH) family can be randomised to produce a library of molecules, at least some of which may preferably be capable of binding nucleic acid when used in the methods of the present invention. In particular, amino acids 1, 2, 5 and 6 are known to be conserved and function in base-specific nucleic acid binding in HTH motifs. Therefore, at least amino acids 1, 2, 5 or 6 would preferably be randomised so as to produce molecules for use according to the present invention. For example, amino acids 1, 5 and 6 can be selected from Asn, Asp, His, Val, Ile, Glu, Gln, Arg, Met, Lys or Leu, and amino acid 2 can be selected from Asn, Asp, His, Val, Ile, Glu, Gln, Arg, Met, Lys, Leu, Cys, Ser, Thr, or Ala.

Another family of transcription factors which may be advantageously employed in the methods of the current invention are the C4 family which includes hormone receptor type transcription factors. Polypeptides of this family can be used to provide molecules for use in selecting nucleic acid binding molecules whose association with nucleic acid is modulatable by a ligand. Amino acids 1, 4, 5 and 9 of the C4 motif are known to be involved in contacting the DNA, and therefore these residues are preferably altered to provide a plurality of different molecules which bind DNA in a ligand dependent manner. For example, amino acids 1 and 5 are selected from Asn, Asp, His, Val, Ile, Glu, Gln, Arg, Met, Lys or Leu, and amino acids 4 and 9 are selected from Gln, Glu, Arg, Lys, Leu or Met.

Particularly preferred examples of DNA binding polypeptides are Cys2-His2 zinc finger binding proteins which, as is well known in the art, bind to target nucleic acid sequences via binding motifs known as zinc fingers. Each zinc finger in a zinc finger nucleic acid binding protein is responsible for determining binding to a nucleic acid triplet, or an overlapping quadruplet, in a nucleic acid binding sequence. Preferably, there are 2 or more zinc fingers, for example 2, 3, 4, 5, 6 or more zinc fingers, in each binding protein.

The general structure of the zinc finger includes a beta turn joined to an alpha helix, with the beta turn being amino-terminal to the helix. Four amino acid residues within the zinc finger coordinate a zinc ion, which stabilizes the structure of the finger. The first two zinc-coordinating residues (often cysteine residues) are located within the beta turn. The other two zinc-coordinating residues (often histidine residues) are located in the alpha helical portion of the zinc finger. Modified zinc fingers, in which one of the canonical zinc coordinating residues is replaced by a different amino acid (e.g. Cys3-His zinc fingers) have been described in WO 02/57293 and can be used in the polypeptides described herein.

A zinc finger binding motif is a structure well known to those in the art and defined in, for example, Miller et al., (1985) EMBO J. 4:1609-1614; Berg (1988) PNAS (USA)

85:99-102; Lee et al., (1989) Science 245:635-637; see International patent applications WO 96/06166 and WO 96/32475, corresponding to U.S. Ser. No. 08/422,107, incorporated herein by reference.

As used herein, "nucleic acid" refers to both RNA and DNA, constructed from natural nucleic acid bases or synthetic bases, or mixtures thereof. Preferably, however, the binding proteins of the invention are DNA binding proteins.

In general, a preferred zinc finger framework has the structure:

(A) $X_{0-2}$ C $X_{1-5}$ C $X_{9-14}$ H $X_{3-6}$ H/C where X is any amino acid, and the numbers in subscript indicate the possible numbers of 30 residues represented by X.

In a preferred aspect of the present invention, zinc finger nucleic acid binding motifs may be represented as motifs having the following primary structure:

(B)
(SEQ ID NO: 93)
$X^a$ C $X_{2-4}$ C $X_{2-3}$ F $X^c$ X X X X L X X H X X $X^b$ H-linker
                 -1  1 2 3 4 5 6 7 8 9 wherein X (including $X^a$, $X^b$ and $X^c$) is any amino acid. $X_{2-4}$ and $X_{2-3}$ refer to the presence of 2 or 4, or 2 or 3, amino acids, respectively. The Cys and His residues, which together co-ordinate the zinc metal atom, are marked in bold text and are usually invariant, as is the Leu residue at position +4 in the α-helix.

Modifications to this representation may occur or be effected without necessarily abolishing zinc finger function, by insertion, mutation or deletion of amino acids. For example it is known that the second His residue may be replaced by Cys (Krizek et al., (1991) J. Am. Chem. Soc. 113:4518-4523) and that Leu at +4 can in some circumstances be replaced with Arg. The Phe residue before $X_c$ may be replaced by any aromatic other than Trp. Moreover, experiments have shown that departure from the preferred structure and residue assignments for the zinc finger are tolerated and may even prove beneficial in binding to certain nucleic acid sequences. Even taking this into account, however, the general structure involving an α-helix co-ordinated by a zinc atom which contacts four Cys or His residues, does not alter. As used herein, structures (A) and (B) above are taken as an exemplary structure representing all zinc finger structures of the Cys2-His2 type.

Preferably; $X^a$ is F/Y-X, or P-F/Y-X. In this context, X is any amino acid. Preferably, in this context X is E, K, T or S. Less preferred but also envisaged are Q, V, A and P. The remaining amino acids remain possible.

Preferably, $X_{2-4}$ consists of two amino acids rather than four. The first of these amino acids may be any amino acid, but S, E, K, T, P and R are preferred. Advantageously, it is P or R. The second of these amino acids is preferably E, although any amino acid may be used.

Preferably, $X^b$ is T or I.
Preferably, $X^c$ is S or T.
Preferably, $X_{2-3}$ is G-K-A, G-K-C, G-K-S or G-K-G. However, departures from the preferred residues are possible, for example in the form of M-R-N or M-R.

Preferably, the linker is T-G-E-K (SEQ ID NO: 94) or T-G-E-K-P (SEQ ID NO: 95).

As set out above, the major binding interactions occur with amino acids −1, +2, +3 and +6. Amino acids +4 and +7 are largely invariant. The remaining amino acids may be essentially any amino acids. Preferably, position +9 is occupied by Arg or Lys. Advantageously, positions +1, +5 and +8 are not hydrophobic amino acids, that is to say are not Phe, Trp or Tyr.

In a most preferred aspect, therefore, bringing together the above, it is possible to define every residue in a zinc finger nucleic acid binding motif which will bind specifically to a given nucleic acid quadruplet.

The code provided herein is not entirely rigid; certain choices are provided. For example, positions +1, +5 and +8 may have any amino acid allocation, whilst other positions may have certain options: for example, the present rules provide that, for binding to a central T residue, any one of Ala, Ser or Val may be used at +3. In its broadest sense, a very large number of proteins is described which is capable of binding to every defined target nucleic acid quadruplet.

Preferably, however, the number of possibilities may be significantly reduced. For example, the non-critical residues +1, +5 and +8 may be occupied by the residues Lys, Thr and Gln respectively as a default option. In the case of the other choices, for example, the first-given option may be employed as a default. Thus, the code set forth above allows the design of a single, defined polypeptide (a "default" polypeptide) which will bind to its target quadruplet.

The α-helix of a zinc finger binding protein aligns antiparallel to the nucleic acid strand, such that the primary nucleic acid sequence is arranged 3' to 5' in order to correspond with the N terminal to C-terminal sequence of the zinc finger. Since nucleic acid sequences are conventionally written 5' to 3', and amino acid sequences N-terminus to C-terminus, the result is that when a nucleic acid sequence and a zinc finger protein are aligned according to convention, the primary interaction of the zinc finger is with the − strand of the nucleic acid, since it is this strand which is aligned 3' to 5'. These conventions are followed in the nomenclature used herein. It should be noted, however, that in nature certain fingers, such as finger 4 of the protein GLI, bind to the + strand of nucleic acid: see Suzuki et al., (1994) NAR 22:3397-3405 and Pavletich and Pabo, (1993) Science 261:1701-1707. The incorporation of such fingers into DNA binding polypeptides according to the invention is envisaged.

The present invention may be integrated with the rules set forth for zinc finger polypeptide design in PCT patent applications having the following publication numbers:— WO 98/53057, WO 98/53060, WO 98/53058 and WO 98/53059. These documents describe improved techniques for designing zinc finger polypeptides capable of binding desired nucleic acid sequences by rational design. In combination with selection procedures, such as phage display, set forth for example in WO 96/06166, these techniques enable the production of zinc finger polypeptides capable of recognising practically any desired sequence.

A ZFP produced in part by rational design may be a ZFP that is selected from a library where the variation has been reduced by determining one or more amino acid positions through selection of residues according to design rules, such as the foregoing. A ZFP produced entirely through rational design is designed from design rules without selection from a library.

Zinc finger binding motifs designed and/or selected according to the foregoing teachings may be combined into nucleic acid binding polypeptide molecules having a multiplicity of zinc fingers. Preferably, the proteins have at least two zinc fingers. In nature, zinc finger binding proteins commonly have at least three zinc fingers, although two-zinc finger proteins such as Tramtrack are known. The presence of at least three zinc fingers is preferred. Nucleic acid binding proteins may be constructed by joining the required fingers end to end, N-terminus to C-terminus. Preferably, this is effected by joining together the relevant nucleic acid sequences which encode the zinc fingers to produce a composite nucleic acid coding sequence encoding the entire binding protein.

A "leader" peptide may be added to the N-terminal finger. Preferably, the leader peptide is MAEEKP (SEQ ID NO: 1).

Moreover, linkers may be used to link together zinc finger motifs to create a DNA binding polypeptide; such linkers are described in WO200153480 and typically have a structure of a canonical linker sequence selected from GEKP (SEQ ID NO: 2), GERP (SEQ ID NO: 3), GQKP (SEQ ID NO: 4) and GQRP (SEQ ID NO: 5). More preferably, the linker sequence comprises a sequence selected from: GGEKP (SEQ ID NO: 6), GGQKP (SEQ ID NO: 7), GGSGEKP (SEQ ID NO: 8), GGSGQKP (SEQ ID NO: 9), GGSGGS-GEKP (SEQ ID NO: 10), and GGSGGSGQKP (SEQ ID NO: 11). See also U.S. Pat. Nos. 6,479,626 and 6,903,185 for additional disclosure regarding inter-finger linkers.

B. Effector Molecules and Functional Domains

In accordance with the invention, an effector molecule or functional domain is preferably fused to the DNA binding protein in order to mediate an effect in the mitochondrion. The DNA binding proteins of the invention can optionally be associated with transcriptional regulatory domains for modulation of gene expression. The DNA binding protein can be covalently or non-covalently associated with one or more regulatory domains, alternatively two or more regulatory domains, with the two or more domains being two copies of the same domain, or two different domains. The regulatory domains can be covalently linked to the DNA binding protein, e.g., via an amino acid linker, as part of a fusion protein. The DNA binding proteins can also be associated with a regulatory domain via a non-covalent dimerization domain, e.g., a leucine zipper, a STAT protein N terminal domain, or an FK506 binding protein (see, e.g., O'Shea, Science 254: 539 (1991), Barahmand-Pour et al., Curr. Top. Microbiol. Immunol. 211:121-128 (1996); Klemm et al., Annu Rev. Immunol. 16:569-592 (1998); Klenim et al., Annu Rev. Immunol. 16:569-592 (1998); Ho et al., Nature 382:822-826 (1996); and Pomeranz et al., Biochem. 37:965 (1998)). The regulatory domain can be associated with the DNA binding protein at any suitable position, including the C- or N-terminus of the DNA binding protein.

Common regulatory domains for addition to the DNA binding protein include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., Cell 84:825-30 (1996) for a review of proteins and nucleic acid elements involved in transcription; transcription factors in general are reviewed in Barnes & Adcock, Clin. Exp. Allergy 25 Suppl. 2:46-9 (1995) and Roeder, Methods Enzymol. 273:165-71 (1996)). Databases dedicated to transcription factors are known (see, e.g., Science 269:630 (1995)). Nuclear hormone receptor transcription factors are described in, for example, Rosen et al., J. Med. Chem. 38:4855-74 (1995). The C/EBP family of transcription factors are reviewed in Wedel et al., Immunobiology 193:171-85 (1995). Coactivators and co-repressors that mediate transcription regulation by nuclear hormone receptors are reviewed in, for example, Meier, Eur. J. Endocrinol. 134(2): 158-9 (1996); Kaiser et al., Trends Biochem. Sci. 21:342-5 (1996); and Utley et al., Nature 394:498-502 (1998)). GATA transcription factors, which are involved in regulation of hematopoiesis, are described in for example, Simon, Nat. Genet. 11:9-11 (1995); Weiss et al., Exp. Hematol. 23:99-107. TATA box binding protein (TBP) and its associated TAF polypeptides (which include TAP30, TAF55, TAF80, TAF110, TAF150, and TAF250) are described in Goodrich & Tjian, Curr. Opin. Cell Biol. 6:403-9 (1994) and Hurley, Curr. Opin. Struct. Biol. 6:69-75 (1996). The STAT family of transcription factors are reviewed in, for example, Barahmand-Pour et al., Curr. Top. Microbiol. Immunol. 211:121-8 (1996). Transcription factors involved in disease are reviewed in Aso et al., J. Clin. Invest. 97:1561-9 (1996).

In one embodiment, the KRAB repression domain from the human KOX-1 protein is used as a transcriptional repressor (Thiesen et al., New Biologist 2:363-374 (1990); Margolin et al., PNAS 91:4509-4513 (1994); Pengue et al., Nuc. Acids Res. 22:2908-2914 (1994); Witzgall et al., PNAS 91:4514-4518 (1994); see also Example III)). In another embodiment, KAP-1, a KRAB co-repressor, is used with KRAB (Friedman et al., Genes Dev. 10:2067-2078 (1996)). Alternatively, KAP-1 can be used alone with a DNA binding protein. Other preferred transcription factors and transcription factor domains that act as transcriptional repressors include MAD (see, e.g., Sommer et al., J. Biol. Chem. 273:6632-6642 (1998); Gupta et al., Oncogene 16:1149-1159 (1998); Queva et al., Oncogene 16:967-977 (1998); Larsson et al., Oncogene 15:737-748 (1997); Laherty et al., Cell 89:349-356 (1997); and Cultraro et al., Mol Cell. Biol. 17:2353-2359 (19977)); FKHR (forkhead in rhapdosarcoma gene; Ginsberg et al., Cancer Res. 15:3542-3546 (1998); Epstein et al., Mol. Cell. Biol. 18:4118-413-0 (1998)); EGR-1 (early growth response gene-product-1; Yan et al., PNAS 95:8298-8303 (1998); and Liu et al., Cancer Gene Ther. 5:3-28 (1998)); the ets2 repressor factor repressor domain (ERD; Sgouras et al., EMBO J. 14:4781-4793 ((19095)); and the MAD smSIN3 interaction domain (SID; Ayer et al., Mol. Cell. Biol. 16:5772-5781 (1996)).

In one embodiment, the HSV VP16 activation domain is used as a transcriptional activator (see, e.g., Hagmann et al., J. Virol. 71:5952-5962 (1997)). Other preferred transcription factors that could supply activation domains include the VP64 activation domain (Seipel et al., EMBO J. 11:49614968 (1996)); nuclear hormone receptors (see, e.g., Torchia et al., Curr. Opin. Cell. Biol. 10:373-383 (1998)); the p65 subunit of nuclear factor kappa B (Bitko & Batik, J. Virol. 72:5610-5618 (1998) and Doyle & Hunt, Neuroreport 8:2937-2942 (1997)); and EGR-1 (early growth response gene product-1; Yan et al., PNAS 95:8298-8303 (1998); and Liu et al., Cancer Gene Ther. 5:3-28 (1998)).

Kinases, phosphatases, and other proteins that modify polypeptides involved in gene regulation are also useful as regulatory domains for DNA binding proteins. Such modifiers are often involved in switching on or off transcription mediated by, for example, hormones. Kinases involved in transcription regulation are reviewed in Davis, Mol. Reprod.

Dev. 42:459-67 (1995), Jackson et al., Adv. Second Messenger Phosphoprotein Res. 28:279-86 (1993), and Boulikas, Crit. Rev. Eukayot. Gene Expr. 5:1-77 (1995), while phosphatases are reviewed in, for example, Schonthal & Semin, Cancer Biol. 6:239-48 (1995). Nuclear tyrosine kinases are described in Wang, Trends Biochem. Sci. 19:373-6 (1994).

As described, useful domains can also be obtained from the gene products of oncogenes (e.g., myc, jun, fos, myb, max, mad, rel, ets, bcl, myb, mos family members) and their associated factors and modifiers. Oncogenes are described in, for example, Cooper, Oncogenes, 2nd ed., The Jones and Bartlett Series in Biology, Boston, Mass., Jones and Bartlett Publishers, 1995. The ets transcription factors are reviewed in Waslylk et al., Eur. J. Biochem. 211:7-18 (1993) and Crepieux et al., Crit. Rev. Oncog. 5:615-38 (1994). Myc oncogenes are reviewed in, for example, Ryan et al., Biochem. J. 314:713-21 (1996). The jun and fos transcription factors are described in, for example, The Fos and Jun Families of Transcription Factors, Angel & Herrlich, eds. (1994). The max oncogene is reviewed in Hurlin et al., Cold Spring Harb. Symp. Quant. Biol. 59:109-16. The myb gene family is reviewed in Kanei-Ishii et al., Curr. Top. Microbiol. Immunol. 211:89-98 (1996). The mos family is reviewed in Yew et al., Curr. Opin. Genet. Dev. 3:19-25 (1993).

Effector domains can include regulatory domains obtained from DNA repair enzymes and their associated actors and modifiers. DNA repair systems are reviewed in, for example, Vos, Curr. Opin. Cell Biol. 4:385-95 (1992); Sancar, Ann. Rev. Genet. 29:69-105 (1995); Lehmann, Genet. Eng. 17:1-19 (1995); and Wood, Ann. Rev. Biochem. 65:135-67 (1996). DNA rearrangement enzymes and their associated factors and modifiers can also be used as regulatory domains (see, e.g., Gangloff et al., Experientia 50:261-9 (1994); Sadowski, FASEB J. 7:760-7 (1993)).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., Bioessays, 16:13-22 (1994), and methyltransferases are described in Cheng, Curr. Opin. Struct. Biol. 5:4-10 (1995). Chromatin associated proteins and their modifiers (e.g., kinases, acetylases and deacetylases), such as histone deacetylase (Wolffe, Science 272:371-2 (1996)) are also useful as domains for addition to the DNA binding protein of choice. In one embodiment, the regulatory domain is a DNA methyl transferase that acts as a transcriptional repressor (see, e.g., Van den Wyngaert et al., FEBS Lett. 426:283-289 (1998); Flynn et al., J. Mol. Biol. 279:101-116 (1998); Okano et al., Nucleic Acids Res. 26:2536-2540 (1998); and Zardo & Caiafa, J. Biol. Chem. 273:16517-16520 (1998)).

In another embodiment, Type IIs endonucleases such as Fok1 are used as functional domains to effect DNA cleavage (see, e.g., WO95/09233; and PCT/US94/01201). Such cleavage can be useful to promote targeted mutagenesis and/or targeted recombination. See, for example, WO 03/80809, WO 03/87341, WO 2004/37977 and WO 2005/14791. If said mutagenesis or targeted recombination occurs within a gene so as to inactivate that gene, the result can be repression of expression of the gene.

Factors that control chromatin and DNA structure, movement and localization and their associated factors and modifiers; factors derived from microbes (e.g., prokaryotes, eukaryotes and virus) and factors that associate with or modify them can also be used to obtain chimaeric proteins.

In one embodiment, recombinases and integrases are used as regulatory domains. In one embodiment, histone acetyltransferase is used as a transcriptional activator (see, e.g., Jin & Scotto, Mol. Cell. Biol. 18:4377-4384 (1998); Wolffe, Science 272:371-372 (1996); Taunton et al., Science 272:408-411 (1996); and Hassig et al., PNAS 95:3519-3524 (1998)). In another embodiment, histone deacetylase is used as a transcriptional repressor (see, e.g., Jin & Scotto, Mol. Cell. Biol. 18:4377-4384-(1998); Syntichaki & Thireos, J. Biol. Chem. 273:24414-24419 (1998); Sakaguchi et al., Genes Dev. 12:2831-2841 (1998); and Martinez et al., J. Biol. Chem. 273:23781-23785 (1998)).

In certain embodiments, the effector molecule or functional domain is a restriction endonuclease. Advantageously, it is the DNA cleavage domain of a Type IIs restriction endonuclease, and most advantageously it is FokI. For a review of the zinc finger-nuclease fusions, see Durai et al., Nucleic Acids Research 2005 33(18):5978-5990; also Chadrasegaran and Smith, Biol Chem. 1999 July-August; 380 (7-8):841-8. Type IIs restriction endonucleases are known in the art, and reviewed by Szybalski et al., Gene. 1991 April; 100:13-26. Erratum in: Gene 1991 Dec. 20; 109(1):169.

C. Mitochondrial Targeting Signals and Nuclear Export Signals

Mitochondrial targeting signals (MTS) are known in the art and direct the transport of passenger polypeptides across the mitochondrial membranes and facilitate their anchoring in the mitochondrial membranes. Typically, MTS comprise charged, hydrophobic and hydroxylated amino acid residues. Examples of MTS include the N-terminal region of human cytochrome c oxidase subunit VIII, the N-terminal region of the P1 isoform of subunit c of human ATP synthase, or the N-terminal region of the aldehyde dehydrogenase targeting sequence. The mechanism of mitochondrial transport, and MTS, are reviewed in Pfanner and Geissler, Nature Reviews Mol Cell Biol 2:339-349. Specific uses of MTS to deliver polypeptides to mitochondria are described in US 2004/0072774 and Tanaka et al., 2002 J Biomed Sci 9:534-541.

Nuclear export signals (NES) are also known in the art. Typical NES are rich in hydrophobic amino acids including leucine and isoleucine. In one export mechanism, leucine-rich NES interact with CRM1/exportin1 to mediate export from the nucleus. NES are known from Protein Kinase Inhibitor (LALKLAGLDIN) (SEQ ID NO: 12), HIV-1 Rev (LQLPPLERLTLD) (SEQ ID NO: 13) and MAP kinase kinase (LGLKLEELELE) (SEQ ID NO: 14), MVM NS2 (MTKKF-GTLTI) (SEQ ID NO: 15), NMD3 (LAEML-EDLHI) (SEQ ID NO: 16), An3 (LDQQF-AGLDL) (SEQ ID NO: 17), IκBα (MVKEL-QEIRL) (SEQ ID NO: 18), Cyclin B1 (LCQAF-SDVIL) (SEQ ID NO: 19) and TFIIIA (L-PVL-ENLTL) (SEQ ID NO: 20). For a review, as well as teaching on the design of novel NES, see Kutay and Guettinger, TRENDS in Cell Biology Vol. 15 No. 3 Mar. 2005.

MTS and NES can be fused with a DNA binding protein in accordance with procedures known in the art, and described in US 2004/0072774, Tanaka et al., 2002 J Biomed Sci 9:534-541, and Kutay and Guettinger, TRENDS in Cell Biology Vol. 15 No. 3 Mar. 2005.

D. Nucleic Acid Vectors Encoding DNA Binding Proteins

A nucleic acid encoding the DNA binding protein according to the invention can be incorporated into vectors for manipulation and expression. In this context, the DNA binding protein is understood to comprise the NES and MTS necessary in the method of the invention. Vectors are used both for cloning purposes, to generate the required constructs, and to express the constructs in eukarytotic cells for the delivery of nucleic acid binding proteins to mitochondria.

As used herein, vector (or plasmid) refers to discrete elements that are used to introduce heterologous nucleic acid into cells for either expression or replication thereof. Selection and use of such vehicles are well within the skill of the person of ordinary skill in the art. Many vectors are available, and selection of appropriate vector will depend on the intended use of the vector, i.e. whether it is to be used for DNA amplification or for nucleic acid expression, the size of the DNA to be inserted into the vector, and the host cell to be transformed with the vector. Each vector contains various components depending on its function (amplification of DNA or expression of DNA) and the host cell for which it is compatible. The vector components can include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2μ plasmid origin is suitable for yeast, and various viral origins (e.g. SV40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in *E. coli* and then the same vector is transfected into yeast, mammalian or plant cells even though it is not capable of replicating independently of the host cell chromosome. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

Since the replication of vectors is conveniently done in *E. coli*, an *E. coli* genetic marker and an *E. coli* origin of replication are advantageously included. These can be obtained from *E. coli* plasmids, such as pBR322, Bluescript© vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up DNA binding protein nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHER or glutamine synthase (GS) marker, selection pressure can be imposed by culturing the transformants under conditions in which the pressure is progressively increased, thereby leading to amplification (at its chromosomal integration site) of both the selection gene and the linked DNA that encodes the DNA binding protein. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from amplified DNA.

Expression and cloning vectors usually contain a promoter that is recognised by the host organism and is operably linked to nucleic acid encoding DNA binding protein. Such a promoter may be inducible or constitutive. The promoters are operably linked to DNA encoding the DNA binding protein by removing the promoter from the source DNA by restriction enzyme digestion and inserting the isolated promoter sequence into the vector. Both the native DNA binding protein promoter sequence and many heterologous promoters may be used to direct expression of DNA binding protein encoding DNA.

DNA binding protein gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with DNA binding protein sequence, provided such promoters are compatible with the host cell systems.

Transcription of a DNA encoding DNA binding protein by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the vector at a position 5' or 3' to DNA binding protein DNA, but is preferably located at a site 5' from the promoter.

Advantageously, a eukarytotic expression vector encoding a DNA binding protein according to the invention may comprise a locus control region (LCR). LCRs are capable of directing high-level integration site independent expression of transgenes integrated into host cell chromatin, which is of importance especially where the DNA binding protein gene is to be expressed in the context of a permanently-transfected eukarytotic cell line in which chromosomal integration of the vector has occurred, or in transgenic animals.

Eukaryotic vectors may also contain sequences necessary for the termination of transcription and for stabilising the mRNA. Such sequences are commonly available from the 5' and 3' untranslated regions of eukaryotic or viral DNAs or cDNAs.

An expression vector includes any vector capable of expressing nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding DNA binding protein may be inserted into a vector suitable for expression of cDNAs in mammalian cells, e.g. a CMV enhancer-based vector such as pEVRF (Matthias, et al., (1989) NAR 17, 6418).

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing DNA binding protein expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing the DNA binding protein. Eukaryotes comprising the vector of the invention produce the DNA binding protein according to the invention and cause it to be transferred to the mitochondria. Suitable prokaryotes include eubacteria, such as Gram-negative or Gram-positive organisms, such as *E. coli*, e.g. *E. coli* K-12 strains, DH5α and HB101, or Bacilli. Further hosts suitable for the DNA binding protein encoding vectors include eukaryotic microbes such as filamentous fungi or yeast, e.g. *Saccharomyces cerevisiae*. Higher eukaryotic cells include plant cells and animal cells such as insect and vertebrate cells, particularly mammalian cells including human cells, non-human mammalian cells or nucleated cells from other multicellular organisms. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a multicellular host organism.

DNA may be stably incorporated into cells or may be transiently expressed using methods known in the art. Stably transfected cells can be prepared by contacting cells with an expression vector having a selectable marker gene, and growing the transfected cells under conditions selective for cells expressing the marker gene. To prepare transient transfectants, cells may be transfected with a reporter gene to monitor transfection efficiency.

To produce such stably or transiently transfected cells, the cells are transfected with a sufficient amount of the DNA binding protein-encoding nucleic acid to allow expression of the DNA binding protein. The precise amounts of DNA encoding the DNA binding protein may be empirically determined and optimised for a particular cell and assay.

Host cells are transfected or, preferably, transformed with the above-mentioned expression or cloning vectors of this invention and cultured in conventional nutrient media modified as appropriate for inducing promoters, selecting transformants, or amplifying the genes encoding the desired sequences. Heterologous DNA can be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of heterologous DNA occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions whereby the DNA binding protein encoded by the DNA is expressed. The composition of suitable media is known to those in the art, so that they can be readily prepared. Suitable culturing media are also commercially available.

E. Eukarytotic Cells

Nucleic acid constructs in accordance with the present invention are introduced into eukarytotic cells, in order to express o the DNA-binding peptide encoded by the construct within the construct. The eukaryotic cell may be, for example, an animal cell, a fungal cell, or a plant cell. In one embodiment of the present invention, the eukarytotic cell is a mammalian cell, including a bone-marrow cell, a germ-line cell, a post-mitotic, cell (e.g., a cell of the central nervous system), a progenitor cell, and a stem cell. In certain embodiments, the cell is a human cell, including a cell from a human cell line (e.g., HeLa cells) or a primary cell.

The nucleic-acid construct of the present invention may be introduced into the eukarytotic cell by standard methods of transfection or transformation known in the art. Examples of methods by which the construct may be introduced into the cell include, without limitation, electroporation, DEAE Dextran transfection, calcium phosphate transfection, cationic liposome fusion, protoplast fusion, creation of an in vivo electrical field, DNA-coated microprojectile bombardment, injection with a recombinant replication-defective virus, homologous recombination, ex vivo gene therapy, a viral vector, and naked DNA transfer, or any combination thereof. Recombinant viral vectors suitable for gene therapy include, but are not limited to, vectors derived from the genomes of viruses such as retroviruses, lentiviruses, HSV, adenovirus, adeno-associated virus, Semiliki Forest virus, cytomegalovirus, and vaccinia virus and its derivatives such as MVA.

Nucleic acid constructs may be introduced into the eukarytotic cell in vitro, using conventional procedures, to achieve expression in the cells of the peptide of the present invention. Eukarytotic cells expressing the peptide then may be introduced into a mammal, to provide the mammal with cells such that the functional peptide is expressed within the mitochondria in vivo. In such an ex vivo gene therapy approach, the eukarytotic cells are preferably removed from the mammal, subjected to techniques to incorporate the nucleic acid construct, and then reintroduced into the mammal. However, the eukarytotic cells also may be derived from an organism other than the mammal, either of the same, or a different, species.

F. Uses

The invention provides DNA binding proteins which are delivered to the mitochondria in eukaryotic cells. The DNA binding proteins, once inside the mitochondria, may mediate a number of activities.

Thus, DNA binding proteins according to the invention may be employed in a wide variety of applications, including diagnostics and as research tools. DNA binding polypeptides according to the invention can preferably differentiate between different target mtDNA molecules.

In a further embodiment, their binding affinities for the mtDNA target sequences are optionally modulated by DNA binding ligand(s) as described in WO200073434. DNA binding polypeptides according to the invention are useful in switching or modulating mitochondrial gene expression, as well as correction of mitochondrial genetic defects by cleavage of mtDNA.

Targeted mtDNA binding polypeptides, such as zinc fingers, according to the invention may moreover be employed in the regulation of mitochondrial gene transcription, for example by specific cleavage of mitochondrial nucleic acid sequences using a fusion polypeptide comprising a zinc finger DNA binding domain and a DNA cleavage domain, or by fusion of an transcriptional regulatory domain to a zinc finger, to activate or repress transcription from a gene which possesses the zinc finger binding sequence.

Correction of Mitochondrial Disorders

The present invention provides means for the correction of mitochondrial disorders through, inter alia, modification of the mitochondrial genome or modulation of mitochondrial gene expression.

A "mitochondrial disorder" is a condition, disease, or disorder characterized by a defect in activity or function of mitochondria, particularly a defect in mitochondrial activity or function that results from, or is associated with, a mutation in mtDNA. Examples of mitochondrial disorders include, without limitation, aging; AD (Alzheimer's Disease); ADPD (Alzheimer's Disease and Parkinsons's Disease); aminoglycoside-induced deafness; cardiomyopathy; CPEO (chronic progressive external ophthalmoplegia); encephalomyopathy; FBSN (familial bilateral striatal necrosis); FICP (Fatal Infantile Cardiomyopathy Plus, a MELAS-associated cardiomyopathy); LDYT (Leber's hereditary optic neuropathy and DysTonia); LHON (Leber hereditary optic neuropathy); LIMM (Lethal Infantile Mitochondrial Myopathy); MM (Mitochondrial Myopathy); MMC (Maternal Myopathy and Cardiomyopathy); MELAS (mitochondrial myopathy, encephalopathy, lactic acidosis, and stroke-like episodes); MERRF (myoclonic epilepsy with stroke-like episodes); MERRF (Myoclonic Epilepsy and Ragged Red Muscle Fibers); MILS (maternally-inherited Leigh syndrome); mitochondrial myopathy; NARP (Neurogenic muscle weakness, Ataxia, and Retinitis Pigmentosa; alternate phenotype at this locus is reported as Leigh Disease); PEO; SNE (subacute necrotizing encephalopathy); MHCM (Maternally inherited Hypertrophic CardioMyopathy); CPEO (Chronic Progressive External Ophthalmoplegia); KSS (Kearns Sayre Syndrome); DM (Diabetes Mellitus); DMDF (Diabetes Mellitus+DeaFness); CIPO (Chronic Intestinal Pseudoobstruction with myopathy and Ophthalmoplegia); DEAF (Maternally inherited DEAFness or aminoglycoside-induced DEAFness); PEM (Progressive encephalopathy) and SNHL (SensoriNeural Hearing Loss).

In one embodiment of the present invention, the mitochondrial disorder is associated with a mutation (e.g., a point mutation) in mtDNA. A "mutation", as used herein, is a permanent, transmissible change in genetic material. As further used herein, the term "wild-type" refers to the characteristic genotype (or phenotype) for a particular gene (or its gene product), as found most frequently in its natural source (e.g., in a natural population).

Regulation of Gene Expression In Vivo

In certain embodiments of the present invention, DNA binding polypeptides are capable of binding to a target sequence in mtDNA and are used to regulate expression from a mitochondrial gene in vivo.

The target mitochondrial gene may be a mutant mitochondrial gene, whose sequence differs from that of a wild-type gene. In such a case, the mitochondrial DNA may be destroyed, such as by cleavage, to correct a genetic defect as a result of heteroplasmy. The DNA binding polypeptide is typically expressed from a nucleic acid construct present in the host cell comprising the target mtDNA sequence. The nucleic acid construct is optionally stably integrated into the genome of the host cell.

A cell according to the invention comprises a target mtDNA sequence and a construct capable of directing expression of the DNA binding polypeptide in the cell.

Suitable constructs for expressing the DNA binding polypeptide are known in the art and are described in section D above. The coding sequence can be expressed constitutively or its expression can be regulated. Expression may be ubiquitous or tissue-specific. Suitable regulatory sequences are known in the art and are also described in section D above. Thus the DNA construct will comprise a nucleic acid sequence encoding a DNA binding polypeptide operably linked to a regulatory sequence capable of directing expression of the DNA binding polypeptide in a host cell.

Techniques for introducing nucleic acid constructs into cells are known in the art for both prokaryotic and eukaryotic cells. Many of these techniques are mentioned below in the section on the production of transgenic organisms.

The term "multicellular organism" here denotes all multicellular plants and animals except humans which comprise mitochondria, i.e. prokaryotes are excluded specifically. The term also includes an individual organism in all stages of development, including embryonic and foetal stages. A "transgenic" multicellular organisms is any multicellular organism containing cells that bear genetic information received, directly or indirectly, by deliberate genetic manipulation at the subcellular level, such as by microinjection or infection with recombinant virus. Preferably, the organism is transgenic by virtue of comprising at least a heterologous nucleotide sequence encoding a DNA binding polypeptide as herein defined.

"Transgenic" in the present context does not encompass classical crossbreeding or in vitro fertilization, but rather denotes organisms in which one or more cells receive a recombinant DNA molecule. Transgenic organisms obtained by subsequent classical crossbreeding or in vitro fertilization of one or more transgenic organisms are included within the scope of the term "transgenic".

The term "germline transgenic organism" refers to a transgenic organism in which the genetic information has been taken up and incorporated into a germline cell, therefore conferring the ability to transfer the information to offspring. If such offspring, in fact, possess some or all of that information, then they, too, are transgenic multicellular organisms within the scope of the present invention.

The information to be introduced into the organism can be foreign to the species of animal to which the recipient belongs (i.e., "heterologous"), or can be foreign only to the particular individual recipient, or can be genetic information already possessed by the recipient. In the last case, the introduced gene may be differently expressed than is the native gene.

"Operably linked" refers to polynucleotide sequences which are necessary to effect the expression of coding and non-coding sequences to which they are covalently joined. The nature of such control sequences differs depending upon the host organism; in prokaryotes, such control sequences generally include promoter, ribosomal binding site, and transcription termination sequence; in eukaryotes, such control sequences include, but are not limited to, enhancers, promoters, ribosome binding sites, splice junctions, transcription termination sequences, polyadenylation sequences, insulator elements and matrix attachment sites. The term "control sequences" is intended to include, at a minimum, components whose presence can influence expression, and can also include additional components whose presence is advantageous, for example, leader sequences and fusion partner sequences. In the context of the present invention, control sequences which are essential include an MTS and a NES; other sequences may be required. Fusion partners which comprise effector molecules are generally included in the term "DNA binding polypeptide".

If the nucleic acid constructs are to be integrated into the host genome, it is important to include sequences that will permit expression of polypeptides in a particular genomic context. One possible approach is to use homologous recombination to replace all or part of the endogenous gene whose expression it is desired to regulate with equivalent sequences, wherein the regulatory region comprises a binding site for the DNA binding protein of the invention. This ensures that the gene is subject to the same transcriptional regulatory mechanisms as the endogenous gene, with the exception of regulation by the DNA binding protein of the invention. Alternatively, homologous recombination may be used in a similar manner but with the regulatory sequences also replaced so that the gene is subject to a different form of regulation.

However, if the construct encoding either the DNA binding polypeptide or target DNA is placed randomly in the genome, it is possible that the chromatin in that region will be transcriptionally silent and in a condensed state. If this occurs, then the polypeptide may not be expressed—these are termed position-dependent effects. To overcome this problem, it may be desirable to include locus control regions (LCRs) that maintain the intervening chromatin in a transcriptionally competent open conformation. LCRs (also known as scaffold attachment regions (SARs) or matrix attachment regions (MARs)) are well known in the art—an example being the chicken lysozyme A element (Stief et al., 1989, Nature 341: 343), which can be positioned around an expressible gene of interest to effect an increase in overall expression of the gene and diminish position dependent effects upon incorporation into the organism's genome (Stief et al., 1989, supra). Another example is the CD2 gene LCR described by Lang et al., 1991, Nucl. Acid. Res. 19: 5851-5856.

Thus, a polynucleotide construct for use in the present invention, to introduce a nucleotide sequence encoding a DNA binding polypeptide into the genome of a multicellular organism, typically comprises a nucleotide sequence encoding the DNA binding polypeptide operably linked to a regulatory sequence capable of directing expression of the coding sequence. In addition the polynucleotide construct may comprise flanking sequences homologous to the host cell genome to aid in integration. An alternative approach is to use viral vectors that are capable of integrating into the host genome, such as retroviruses.

Optionally, a nucleotide construct for use in the present invention further comprises flanking LCRs.

Construction of Transgenic Organisms Expressing DNA Binding Polypeptides.

A transgenic organism of the invention is preferably a multicellular eukarytotic organism, such as an animal, a rodent or a fungus. Animals include animals of the phyla cnidaria, ctenophora, platyhelminthes, nematoda, annelida, mollusca, chelicerata, uniramia, crustacea and chordata. Uniramians include the subphylum hexpoda that includes insects such as the winged insects. Chordates includes vertebrate groups such as mammals, birds, reptiles and amphibians. Particular examples of mammals include non-human primates, cats, dogs, ungulates such as cows, goats, pigs, sheep and horses and rodents such as mice, rats, gerbils and hamsters.

Plants include the seed-bearing plants angiosperms and conifers. Angiosperms include dicotyledons and monocotyledons. Examples of dicotyledonous plants include tobacco, (*Nicotiana plumbaginifolia* and *Nicotiana tabacum*), arabidopsis (*Arabidopsis thaliana*), Brassica napus, Brassica nigra, Datura innoxia, Vicia narbonensis, Vicia faba, pea (*Pisum sativum*), cauliflower, carnation and lentil (*Lens culinaris*). Examples of monocotyledonous plants include cereals such as wheat, barley, oats and maize.

Production of Transgenic Animals

Techniques for producing transgenic animals are well known in the art. A useful general textbook on this subject is Houdebine, Transgenic animals—Generation and Use (Harwood Academic, 1997)—an extensive review of the techniques used to generate transgenic animals from fish to mice and cows.

Advances in technologies for embryo micromanipulation now permit introduction of heterologous DNA into, for example, fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In one method, developing embryos are infected with a retrovirus containing the desired DNA, and transgenic animals produced from the infected embryo. In another embodiment, the appropriate DNAs are coinjected into the pronucleus or cytoplasm of embryos, preferably at the single cell stage, and the embryos allowed to develop into mature transgenic animals. Those techniques as well-known. See reviews of standard laboratory procedures for microinjection of heterologous DNAs into mammalian fertilized ova, including Hogan et al., Manipulating the Mouse Embryo, (Cold Spring Harbor Press 1986); Krimpenfort et al., Bio/Technology 9:844 (1991); Palmiter et al., Cell, 41: 343 (1985); Kraemer et al., Genetic manipulation of the Mammalian Embryo, (Cold Spring Harbor Laboratory Press 1985); Hammer et al., Nature, 315: 680 (1985); Wagner et al., U.S. Pat. No. 5,175,385; Krimpenfort et al., U.S. Pat. No. 5,175,384, the respective contents of which are incorporated herein by reference Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology as described in Schnieke, A. E. et al., 1997, Science, 278: 2130 and Cibelli, J. B. et al., 1998, Science, 280: 1256. Using this method, fibroblasts from donor animals are stably transfected with a plasmid incorporating nucleic acid sequences of interest. Stable transfectants are then fused to enucleated oocytes, cultured and transferred into female recipients. For example, transgenic animals may be created which express a DNA-binding protein according to the invention which modulates gene expression in mitochondria.

Analysis of animals for the presence of transgenic sequences would typically be performed by either PCR or Southern blot analysis following standard methods.

By way of a specific example for the construction of transgenic mammals, such as cows, nucleotide constructs comprising a sequence encoding a DNA binding polypeptide are microinjected using, for example, the technique described in U.S. Pat. No. 4,873,191, into oocytes which are obtained from ovaries freshly removed from the mammal. The oocytes are aspirated from the follicles and allowed to settle before fertilization with thawed frozen sperm capacitated with heparin and prefractionated by Percoll gradient to isolate the motile fraction.

The fertilized oocytes are centrifuged, for example, for eight minutes at 15,000 g to visualize the pronuclei for injection and then cultured from the zygote to morula or blastocyst stage in oviduct tissue-conditioned medium. This medium is prepared by using luminal tissues scraped from oviducts and diluted in culture medium. The zygotes are placed in the culture medium within two hours following microinjection.

Oestrous is then synchronized in the intended recipient mammals, such as cattle, by, e.g., administering coprostanol. Oestrous is produced within two days and the embryos are transferred to the recipients 5-7 days after oestrous. Successful transfer can be evaluated in the offspring by Southern blot.

Alternatively, the desired constructs can be introduced into embryonic stem cells (ES cells) and the cells cultured to ensure modification by the transgene. The modified cells are then injected into the blastula embryonic stage and the blastulas replaced into pseudopregnant hosts. The resulting offspring are chimaeric with respect to the ES and host cells, and nonchimeric strains which exclusively comprise the ES progeny can be obtained using conventional cross-breeding. This technique is described, for example, in WO91/10741.

Production of Transgenic Plants

Techniques for producing transgenic plants are well known in the art. Typically, either whole plants, cells or protoplasts may be transformed with a suitable nucleic acid construct encoding a DNA binding polypeptide or target DNA (see above for examples of nucleic acid constructs). There are many methods for introducing transforming DNA constructs into cells, but not all are suitable for delivering DNA to plant cells. Suitable methods include *Agrobacterium* infection (see, among others, Turpen et al., 1993, J. Virol. Methods, 42: 227-239) or direct delivery of DNA such as, for example, by PEG-mediated transformation, by electroporation or by acceleration of DNA coated particles. Acceleration methods are generally preferred and include, for example, microprojectile bombardment. A typical protocol for producing transgenic plants (in particular monocotyledons), taken from U.S. Pat. No. 5,874,265, is described below.

An example of a method for delivering transforming DNA segments to plant cells is microprojectile bombardment. In this method, non-biological particles may be coated with nucleic acids and delivered into cells by a propelling force. Exemplary particles include those comprised of tungsten, gold, platinum, and the like.

A particular advantage of microprojectile bombardment, in addition to it being an effective means of reproducibly stably transforming both dicotyledons and monocotyledons, is that neither the isolation of protoplasts nor the susceptibility to *Agrobacterium* infection is required. An illustrative embodiment of a method for delivering DNA into plant cells by acceleration is a Biolistics Particle Delivery System, which can be used to propel particles coated with DNA through a screen, such as a stainless steel or Nytex screen, onto a filter surface covered with plant cells cultured in suspension. The screen disperses the tungsten-DNA particles so that they are not delivered to the recipient cells in large aggregates. It is believed that without a screen intervening between the projectile apparatus and the cells to be bombarded, the projectiles aggregate and may be too large for attaining a high frequency of transformation. This may be due to damage inflicted on the recipient cells by projectiles that are too large.

For the bombardment, cells in suspension are preferably concentrated on filters. Filters containing the cells to be bombarded are positioned at an appropriate distance below the macroprojectile stopping plate. If desired, one or more screens are also positioned between the gun and the cells to be bombarded. Through the use of techniques set forth herein one may obtain up to 1000 or more clusters of cells transiently expressing a marker gene ("foci") on the bombarded filter. The number of cells in a focus which express the exogenous gene product 48 hours post-bombardment often range from 1 to 10 and average 2 to 3.

After effecting delivery of exogenous DNA to recipient cells by any of the methods discussed above, a preferred step is to identify the transformed cells for further culturing and plant regeneration. This step may include assaying cultures directly for a screenable trait or by exposing the bombarded cultures to a selective agent or agents.

An example of a screenable marker trait is the red pigment produced under the control of the R-locus in maize. This pigment may be detected by culturing cells on a solid support containing nutrient media capable of supporting growth at this stage, incubating the cells at, e.g., 18° C. and greater than 180 $\mu E$ $m^{-2}$ $s^{-1}$, and selecting cells from colonies (visible aggregates of cells) that are pigmented. These cells may be cultured further, either in suspension or on solid media.

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos selective system, bombarded cells on filters are resuspended in nonselective liquid medium, cultured (e.g. for one to two weeks) and transferred to filters overlaying solid medium containing from 1-3 mg/l bialaphos. While ranges of 1-3 mg/l will typically be preferred, it is proposed that ranges of 0.1-50 mg/l will find utility in the practice of the invention. The type of filter for use in bombardment is not believed to be particularly crucial, and can comprise any solid, porous, inert support.

Cells that survive the exposure to the selective agent may be cultured in medium that supports regeneration of plants. Tissue is maintained on a basic medium with hormones for about 2-4 weeks, then transferred to medium with no hormones. After 2-4 weeks, shoot development will signal the time to transfer to another medium.

Regeneration typically requires a progression of media whose composition has been modified to provide the appropriate nutrients and hormonal signals during sequential developmental stages from the transformed callus to the more mature plant. Developing plantlets are transferred to soil, and hardened, e.g., in an environmentally controlled chamber at about 85% relative humidity, 600 ppm $CO_2$, and 250 µE $m^{-2}$ $s^{-1}$ of light. Plants are preferably matured either in a growth chamber or greenhouse. Regeneration will typically take about 3-12 weeks. During regeneration, cells are grown on solid media in tissue culture vessels. An illustrative embodiment of such a vessel is a petri dish. Regenerating plants are preferably grown at about 19° C. to 28° C. After the regenerating plants have reached the stage of shoot and root development, they may be transferred to a greenhouse for further growth and testing.

Genomic DNA may be isolated from callus cell lines and plants to determine the presence of the exogenous gene through the use of techniques well known to those skilled in the art such as PCR and/or Southern blotting.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205-225) and Christou (Agro-Food-Industry Hi-Tech March/April 1994 17-27).

Thus, in one aspect, the present invention relates to a vector system which carries a construct encoding a DNA binding polypeptide or target DNA according to the present invention and which is capable of introducing the construct into the genome of an organism, such as a plant.

The vector system may comprise one vector, but it can comprise at least two vectors. In the case of two vectors, the vector system is normally referred to as a binary vector system. Binary vector systems are described in further detail in Gynheung An et al. (1980), Binary Vectors, *Plant Molecular Biology Manual* A3, 1-19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* (An et al. (1986), *Plant Physiol.* 81, 301-305 and Butcher D. N. et al. (1980), *Tissue Culture Methods for Plant Pathologists*, eds.: D. S. Ingrams and J. P. Helgeson, 203-208).

Several different Ti and Ri plasmids have been constructed which are suitable for the construction of the plant or plant cell constructs described above.

The present invention will now be described by way of the following examples, which are illustrative only and non-limiting.

EXPERIMENTAL PROCEDURES

Engineering and Design of Zinc Finger Proteins for Binding mtBNA Targets
Engineering of mtDNA Specific ZFPs A number of potential target sites suitable for binding zinc fingers have been identified in mtDNA. These include sites in the D-loop region of wt mtDNA as well as sequences containing point mutations involved in the genetic disorders e.g. NARP T8993G. The potential binders have been assembled from the archives of pre-selected two-finger modules created by Sangamo BioSciences Inc. and based on Zif268 randomised libraries described by Isalan et al. (Isalan, M., Klug, A. & Choo, Y. Nat Biotechnol 19, 656-60 (2001)). DNA binding domains were engineered as 3-finger or 4-finger proteins of a 2×2 design and tested for their ability to bind selectively their target sequences. Additionally a non-binding 3-finger protein ZFP-cont and a 6-finger protein with a non-mitochondrial specificity (Papworth, M. et al. Proc Natl Acad Sci USA 100, 1621-6 (2003)) were used as controls.
Construction of Expression Vectors for MTS-ZFPs In order to construct MTS-zinc-finger fusion proteins (MTS-ZFP), the DNA encoding engineered zinc fingers was modified by PCR to introduce either the c-myc (EQKLISEEDL) (SEQ ID NO: 21) or HA (YPYDVPDYA) (SEQ ID NO: 22) epitope tag to the C-terminus of ZFP and flanked with unique XhoI (5') and EcoRI (3') restriction sites. These were joined with PCR-amplified DNA fragments flanked with unique XbaI (5') and XhoI (3') restriction sites, which encoded one of the following N-terminal MTS sequences: (i) a 33 amino acids (aa) pre-sequence from subunit VIII of human cytochrome c oxidase (C8), (ii) a 51 aa pre-sequence from human ATP-synthase F1βsubunit (F) (iii) a 109 aa pre-sequence from *Chlamydomonas reinhardtii* ATP-synthase subunit 6 (R), (iv) a 54 aa pre-sequence of protein MP42 from *T. brucei* (T1), (v) a 59aa pre-sequence of protein MP63 from *T. brucei* (T2) and (vi) a 64aa pre-sequence (this contain MTS and additional N-terminal sequences) of protein 7b from *Leishmania tarentolae* (T3). All the MTS-ZFP constructs were inserted as XbaI (5')-EcoRI (3') fragments into pcDNA3.1(-) (Invitrogen) and their sequences were verified.

Additionally for clone 30 the plasmid F-ZFP30-3'UTR was constructed by inserting into BamHI site of F-ZNE30 the PCR-amplified fragment corresponding to 3'UTR from human mRNA for F1 β subunit of ATP synthase flanked by BamHI sites.
Construction of MTS-ZFPs with Additional C-Terminal Domains In order to construct C8-ZFP-GFP series of plasmids, DNA fragments encoding C8 MTS-zinc fingers and epitope tag fusions were PCR-amplified from C8-ZFP templates with unique BglII (5') and EcoRI (3') sites added at the flanks and cloned in frame with C-terminal GFP protein into BglI and EcoRI sites of pEGFP-N2 vector (Clontech).

The F-ZFP-NES series of plasmids was constructed by PCR-amplification of DNA fragments encoding F MTS zinc finger protein and epitope tag from F-ZFP templates using 5' F-specific primer containing XbaI restriction site and a 3' epitope tag-specific primer containing additionally NES sequence from NS2 protein of MVM (VDEMTKKFGTLTIHDTEK) (SEQ ID NO: 23) and BamHI site added at the extreme 3'. The resulting F-ZFP-NES XbaI-BamHI fragments were cloned into XbaI and BamHI sites of pcDNA3.1 (-) (Invitrogen) and their sequences were verified.

Subsequently chosen F-ZFP-NES clones were also expressed in pIRESpuro3 vector (Clontech) (F-ZFP-NES-puro), which allows for puromycin selection of transfected clones. The F-GFP-ZFP-NES were generated by PCR-amplification of DNA fragment encoding GFP from Potellina sp using pmaxGFP (Amaxa, GmbH) as a template and XhoI-flanked specific primers and inserting resulting product into XhoI site of F-ZFP-NES in pcDNA3.1 (-) backbone. This series of constructs was further used to engineer the F-GFP-ZFP-meth-NES by inserting EcoRI-flanked PCR-fragment encoding a 17 aa-long flexible linker ([SGGGG]3SS) (SEQ ID NO: 24) and the hDNMT3a catalytic domain (residues 592-909) into EcoRI site upstream from NES in F-GFP-ZFP-NES.

To facilitate expression of chimaeric methylases for longer periods and enrich for the methylase positive cells in the transfected population, the F-ZFP-meth-NES expression cassette was constructed in pIRESpuro3, by inserting the PCR amplified region coding for a linker (see above) and a catalytic domain of hDNMT3a flanked by EcoRI sites into the EcoRI site of F-ZEP-NES-puro (FIG. 3A). Analogous construct lacking ZEP-domain, F-meth-NES, was engineered as a control (FIG. 3A).

Gel Retardation Assay

The 3-finger peptides ZFPNARP and ZFPcont and their derivatives were synthesized in vitro and subjected to gel retardation assay using previously described method (Moore, M., Klug, A. & Choo, Y. Proc Natl Acad Sci USA 98, 1437-41 (2001)). The ZFPNARP was tested against its full length target site containing NARP mutation (T8993G) embedded in a 37 bp probe as well as against closely related sites with 1 bp substitutions in the binding site, which included NARP-C mutation (T8993C) and the wt sequence. Binding of zinc finger proteins to the appropriate DNA sequences was also tested in the presence of additional domains such as N-terminal MTS F and C-terminal methylase domain and NES.

Gel retardation assay was also performed on mitochondrial extract from cells transiently expressing mitochondrially targeted F-ZFPNARP. In this case, 24 h post transfection the cells were harvested and intact mitochondria were isolated as described below (see: Cell fractionation). Afterwards, mitochondrial proteins were solubilised by sonication and the mitochondrial extract (about 2-2.5 μg of proteins) was used in the in vitro gel retardation assay on the specific DNA target as described above.

Transfection of Mammalian Cell Lines

Transfections of mammalian cells were all performed using Cell Line Nucleofector (Amaxa biosystems), buffer kit V (Amaxa biosystems) and plasmid DNA purified by Qiafilter MidiPrep Kit (Qiagen). For COS-7 cells program A-24 was used as recommended by the manufacturer while for the cell lines 143B (TK-) and 143B NARP cybrids program 1-13 was empirically determined as optimal. For immunodetection studies zinc finger constructs were expressed in transient system for 24-36 h. While for methylation studies proteins containing catalytic domain of hDNMT3a were expressed for 60 h using pIRESpuro3 vector (Clontech) with 0.5 μg/ml of puromycin added to the culture medium at 12 h post transfection.

Immunodetection of Transiently Expressed Zinc Finger Proteins

Transiently expressed zinc finger proteins were analysed by either immunofluoresce or immuno-blotting. Adherent cells intended for immunofluorescence were grown on coverslips and if required, stained with Mitotracker CMX Red (Molecular Probes) added to the culture medium for 30 min in order to visualize mitochondria. Cells were then washed in PBS and fixed with 4% formaldehyde/PBS directly on cover slips. Following permeabilisation with 1% Triton X-100 and wash in PBS, the zinc-finger proteins were visualized using antibodies against epitope tags—mouse monoclonal antibody 12CA5 against HA tag (Roche) or mouse 9E10 monoclonal antibody against c-myc (Santa Cruz) used at the dilutions of 1:100. This was followed by incubation with a secondary antibody antimouse IgG conjugated to FITC (Vector) used at the dilution of 1:100. For colocalisation studies of ZFP constructs with TFAM and mtSSB the Mitotracker staining step was omitted. Fixed cells were incubated with the TFAM or mtSSB antiserum followed by secondary antibodies conjugated with Texas Red. The immunofluorescence was then viewed using a Bio-Rad confocal microscope. For immunoblot analysis equal amounts of proteins corresponding to total cell lysates or protein fractions (see below) were subjected to SDS-PAGE, transferred to nitrocellulose membranes and blotted with specific antibodies. The blots were further incubated with HRP-conjugated secondary antibodies and visualized using ECL (Amersham).

Labelling of mtDNA

Metabolic labelling of mtDNA in 143B (TK-) wt or T8993G cybrid cells using BrdU was performed according to Garrido et al. (Garrido, N. et al. Mol Biol Cell 14, 1583-96 (2003)) with the following modifications. BrdU was added 12 h after the transfection to a final concentration of 15 μM and cells were incubated for 18-24 h. Following fixation, permeabilisation (see above) and the dehydratation/rehydratation step, DNA was denatured with 2 M HCl for 10 min and washed extensively with PBS and ddH2O. Incorporated BrdU was detected using mAb anti-BrdU (Roche) and secondary anti-mouse antibodies conjugated with Texas Red.

Cell Fractionation

Mitochondria form the 143B wt or T8993G cybrids cells were isolated as described by Minczuk et al (Minczuk, M. et al. Nucleic Acids Res 30, 5074-86 (2002)). The mitochondrial fractions were then incubated in 1× IB buffer (40 mM Tris-HCl, pH 7.4, 25 mM NaCl and 5 mM $MgCl_2$) supplemented with Proteinase K at the concentrations indicated in FIG. 3B. The subcellular fractions normalized for protein contents were analyzed with anti-HA mAb in order to detect ZFP protein constructs. Blotting using antibodies against marker proteins (anti-TFAM serum and anti-GAPDH mAb (Abcam)) was also performed in order to verify the fractions.

Detection of Cytosine Methylation

Total cellular DNA samples intended for cytosine methylation studies were isolated using DNeasy Tissue Kit (Qiagen) and subjected to bisulfite conversion using EZ DNA Methylation Kit (Zymo Research) according to manufacturer's instructions.

Resulting DNA was used as a template for PCR amplification of mtDNA fragments using primers specific for the bisulfite converted mtDNA H-strand. Resulting PCR products were cloned using TOPO-TA Cloning Kit for Sequencing (Invitrogen) and their sequences were analysed.

Example 1

Strategies for Delivering ZFPs to Mitochondria

Zinc fingers are predominantly DNA-binding proteins evolutionary adapted to operate in the nucleus. Even in the absence of nuclear localisation signals (NLS) they often localise in the nucleus (Papworth, M., Kolasinska, P. &

Minczuk, M. Gene in press (2005)). To use designer ZFP to manipulate mtDNA, they have to be both effectively targeted to mitochondria but also at the same time to be absent from the nucleus to avoid binding to nuclear DNA which could be toxic (specific examples discussed in Papworth et al. Proc Natl Acad Sci USA 100, 1621-6 (2003)). The majority of mitochondrial proteins are encoded by nuclear genes and imported from the cytoplasm with an aid of a cleavable N-terminal mitochondrial targeting sequence (MTS). The MTSs vary greatly in length and composition and appear to be individually tailored to different proteins (Pfanner, N. & Geissler, A. Nat Rev Mol Cell Biol 2, 339-49 (2001)). Fusing an MTS to N-termini can deliver exogenous proteins of various kinds to mitochiondria.

To develop and optimise ZFP delivery to mitochondria we tested a library of four-finger ZFPs, engineered by fusing pairs of two-finger units (Moore, M., Klug, A. & Choo, Y. Proc Natl Acad Sci USA 98, 1437-41 (2001)), for their ability to enter mitochondria with an aid of MTSs from natural mitochondrial proteins (Table 1). The zinc finger peptides used were closely related and differed between each other predominantly in amino acids contained within DNA-contacting helices (Table 1) (for full sequences see FIG. 5). The intracellular localisation studies of zinc finger fusions with different MTSs and in the presence or absence of additional C-terminal GFP, revealed a range of possible intracellular destinations for the ZFPs (Table 1) including exclusively nuclear, mitochondrial and nuclear in various proportion and exclusively mitochondrial. The same pattern of variable localisation was seen for a family of 3-finger proteins (data not shown). Addition of a C-terminal GFP to MTS-ZFP fusion impaired the mitochondrial import and a 6-finger ZFP conjugated to MTS was not imported at all (data not shown). This suggests a possible size restriction in mitochondrial import of ZFPs. The variability of localisation pattern between very closely related ZFPs and size restriction on import was a surprising initial setback to our aim of directing ZFPs and their derivatives to mitochondria. Therefore our first challenge was to develop a universal system for routing ZFPs to mitochondria.

Figure 7:
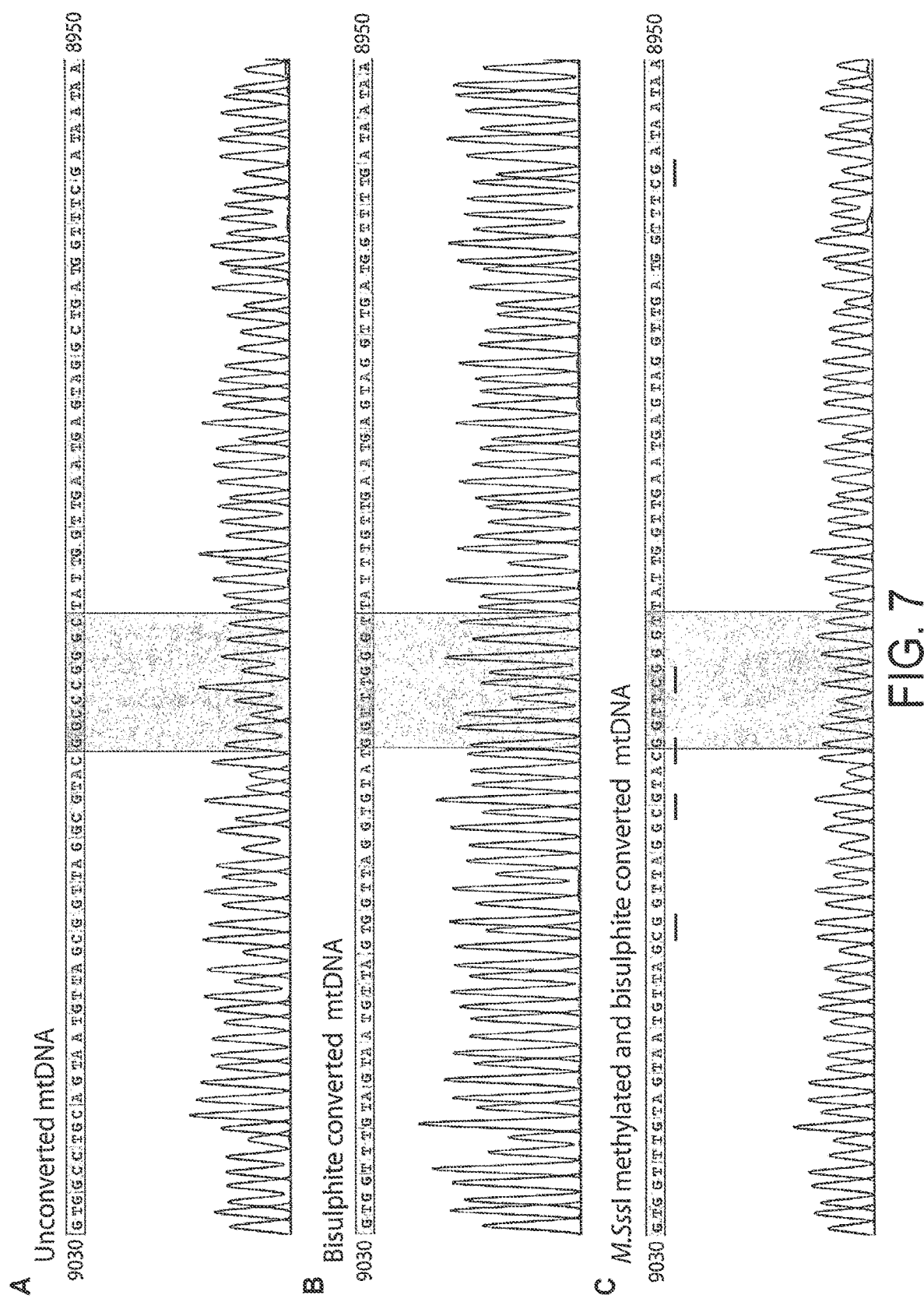

To investigate this we chose ZFP clone 30 (ZFP30) as a case study because it was the most difficult to import into mitochondria (see Table 1). We tested several MTSs in fusion with ZFP30 including the MTSs from endogenous mitochondrial proteins containing zinc finger motifs as well as the 3'UTR from human mRNA for the F1βsubunit of ATP synthase, which is known to aid mitochondrial import (Izquierdo, J. M. & Cuezva, J. M. Biochem J 346 Pt 3, 849-55 (2000)) (FIG. 1A). All these fusion proteins localised in the nuclei. Only occasionally additional mitochondrial localisation has been observed when the MTS from the F1βsubunit of the human mitochondrial ATP synthase (denoted F) was used (FIG. 1A, 7 arrowed).

Predominantly nuclear localisation and the absence of all the MTS-ZFP30 fusions from the cytoplasm (FIG. 1A), suggest their very efficient nuclear targeting, which is likely to be mediated by a group of basic amino acids within the DNA recognition helices of finger 2 and finger 4 (see Table 1 and FIG. 5). To counteract the nuclear import of ZFPs we hypothesized that a nuclear export signal (NES) might facilitate mitochondrial import by either preventing sequestration of the nascent polypeptide in the nucleus or re-routing it out again, thus giving it time to be taken up by mitochondria. To test this, we fused the ZFP30 to MTS from the F1β subunit of the human mitochondrial ATP synthase (F) and NES from nonstructural protein 2 of minute virus of mice (Eichwald, V., Daeffler, L., Klein, M., Rommelaere, J. & Salome, N. J Virol 76, 10307-19 (2002)) to generate the F-ZFP30-NES protein.

Immunofluoresce studies of F-ZFP30-NES fusion showed that it was efficiently targeted to mitochondria and was absent from the nucleus (FIG. 1B). In a control experiment a fusion protein comprising of ZFP30 and NES but lacking a MTS was still found in the nucleus, which is indicative of NES alone cannot function as a mitochondrial import signal (data not shown). Even increasing the size of the F-ZFPNES protein by fusing additional domains still led to the efficient mitochondrial uptake (FIG. 1B). Therefore using NES in conjunction with the N-terminal F MTS facilitated the efficient mitochondrial uptake of a range of ZFP fusion proteins. This approach worked with other ZFPs and their derivatives (Table 2), and was also effective for 3- and 6-finger ZFPs (data not shown). This ability to deliver to mitochondria proteins composed of large exogenous domains fused to a ZFP opened up the possibility of constructing chimaeric enzymes targeted to specific mtDNA sequences.

TABLE 1

Diverse localisation patterns of mitochondrially targeted ZFPs

| Clone ZFP sequence F1 F2 linker F3 F4-1123456-1123456-1123456-1123456 | Localisation | | SEQ ID NO: |
|---|---|---|---|
| | C8-ZFP-GFP C8-ZFP | F-ZFP | |
| 5 RSDVLSA RNDHRIN -RSDTLSR HNHHRKT | — | M | 96 |
| 9 RSDHLST HSNTRKN GGG RSDSLST AGANRTT | — | M/N | 97 |
| 10 RSDVLSV TNQHRTK -RSDHLSE NNSSRTR | N N | M/N | 98 |
| 11 RSDHLSQ TSSNRKT -RSDHLSN RSDDRKK | N N | M/N | 99 |
| 12 RSDHLSE RKDARIT GGG RSDHLSN RSDDRKK | N N/M | M | 100 |
| 15 RSDHLSN RNDDRKK -RSDHLSN QSATRIT | — | M/N | 101 |
| 18 RSDHLSQ TSSNRKT -RSDNLST RSDNRTK | — | M/N | 102 |

TABLE 1-continued

Diverse localisation patterns of mitochondrially targeted ZFPs

| Clone | ZFP sequence F1 F2 linker F3 F4-1123456-1123456-1123456-1123456 | | | | | C8-ZFP-GFP C8-ZFP | F-ZFP | SEQ ID NO: |
|---|---|---|---|---|---|---|---|---|
| 19 | RSDHLSE | DSSHRTR | GGG | RSDSLSV | QNQHRIN | — | M/N | 103 |
| 21 | RSDHLSE | RNDNRKR | — | RSDHLSQ | TSANRTT | N N | M/N | 104 |
| 22 | RSDSLSQ | NSSNRKN | GGG | RSDSLSQ | TSSNRKT | — | M/N | 105 |
| 26 | RSDHLSN | TRDTRKK | GGG | RSDALSV | DSSHRTR | — | M/N | 106 |
| 29 | RSDTLSE | RNDHRTT | GGG | RSDHLSN | RNDDRKK | N N/M | M/N | 107 |
| 30 | RSDHLSE | RNDNRKR | — | RSDHLSN | RNDDRKK | N N | N/M | 108 |
| 31 | RSDHLSE | RNDHRTT | — | RSDHLSE | RRDSRTN | — | N/M | 109 |
| 34 | RSDHLST | HSNTRKN | GGG | RSDHLSE | RNDHRTT | — | M/N | 110 |
| 35 | RSDVLSV | QNNHRIT | — | RSDHLST | ASSARKT | — | N/M | 111 |
| 37 | RSDALSV | HSDTRTK | — | RSDVLSV | QNNHRIT | — | M | 112 |
| 20 | RSDHLTK | NSDHLSR | — | RSDSLSV | QNQHRIN | N M/N | M | 113 |
| 27 | RSDHLTK | NSDHLSR | — | RSDHLSN | TRDTRKK | — | M/N | 114 |
| 32 | TNDDLNT | TSSHLSR | GGG | RSDHLSE | RNDNRKR | — | N/M | 115 |
| 33 | TNDDLNT | TSSHLSR | — | RSDHLSE | RNDHRTT | — | N | 116 |

A family of zinc finger peptides (ZFP) containing 4-fingers (F1 F2 F3 and F4) constructed on the backbone of Zif268, have been selected to bind sequences in mtDNA. These were either a continuous 12 bp binding sites (bound by the clones without a linker) or non-continuous sites containing 1 bp gap in the middle of 12 bp binding site (bound by the clones containing a GGG linker between F2 and F3). Amino acid sequences of DNA-contacting helices of consecutive fingers (amino acid positions -1 to 6 with respect to the start of α-helix) are shown for each clone with amino acids contacting DNA directly, in boldface (ZFP sequence). The N-terminal mitochondrial targeting sequence of the F1β subunit of human ATPase (denoted F) or subunit VIII of human cytochrome c oxidase (C8) were fused to ZFP and their intracellular localisation was analysed in the presence or absence of additional C-terminal GFP (C8-ZFP-GFP, where indicated), by immunofluorescence. Clones exhibited various patterns of intracellular localisation including exclusively nuclear (N), exclusively mitochondrial (M) and mixed mitochondrial and nuclear in the same cell with either predominantly mitochondrial (M/N) or predominantly nuclear (N/M).

Background cytoplasmic localisation was very rarely observed and therefore omitted in these studies. The ZFPs that originated from the same library and contain identical amino acid sequences outside DNA-contacting helixes are grouped together in the upper and lower parts of the table. Clone 30 used for further studies is shadowed. Similar pattern of variable intracellular localisation of ZFPs was seen in either in COS-7 or 143B.

Table 2. Localisation of mitochondrially targeted ZFPs fused to nuclear export signal and exogenous domains

TABLE 2

Localisation of mitochondrially targeted ZFPs (SEQ ID NOS 99-100, 102, 104 and 108, respectively, in order of appearance) fused to nuclear export signal and exogenous domains

| | ZFP sequence | | | | | Localisation | | |
|---|---|---|---|---|---|---|---|---|
| Clone | F1 -1123456 | F2 -1123456 | linker | F3 -1123456 | F4 -1123456 | F-GFP-ZFP-NES | F-ZFP-meth-NES | F-GFP-ZFP-meth-NES |
| 11 | RSDHLSQ | TSSNRKT | — | RSDHLSN | RSDDRKK | M | M | M |
| 12 | RSDHLSE | RKDARIT | GGG | RSDHLSN | RSDDRKK | — | M | — |
| 18 | RSDHLSQ | TSSNRKT | — | RSDNLST | RSDNRTK | M | M/N | M |
| 21 | RSDHLSE | RNDNRKR | — | RSDHLSQ | TSANRIT | M | M | M |
| 30 | RSDHLSE | RNDNRKR | — | RSDHLSN | RNDDRKK | M | M | M |

A number of ZFP proteins containing the MTS F (ZFP clone numbers and sequences indicated in Table 1) were fused with the C-terminal NES and tested for their ability to enter the mitochondria when attached to additional domains, which included: GFP (F-GFP-ZFP-NES), a catalytic domain of the hDNMT3a methylase (F-ZFP-meth-NES) or both GFP and a catalytic domain of hDNMT3a (F-GFP-ZFP-meth-NES). Intracellular localisation of individual clones has been assessed using immunofluorescence and described as mitochondrial (M) when protein was located exclusively in mitochondria or mitochondrially-nuclear (M/N) when it was found in both compartments with a preference for mitochondria. The same results were obtained either in COS-7 or 143B.

Example 2

Figure 2:
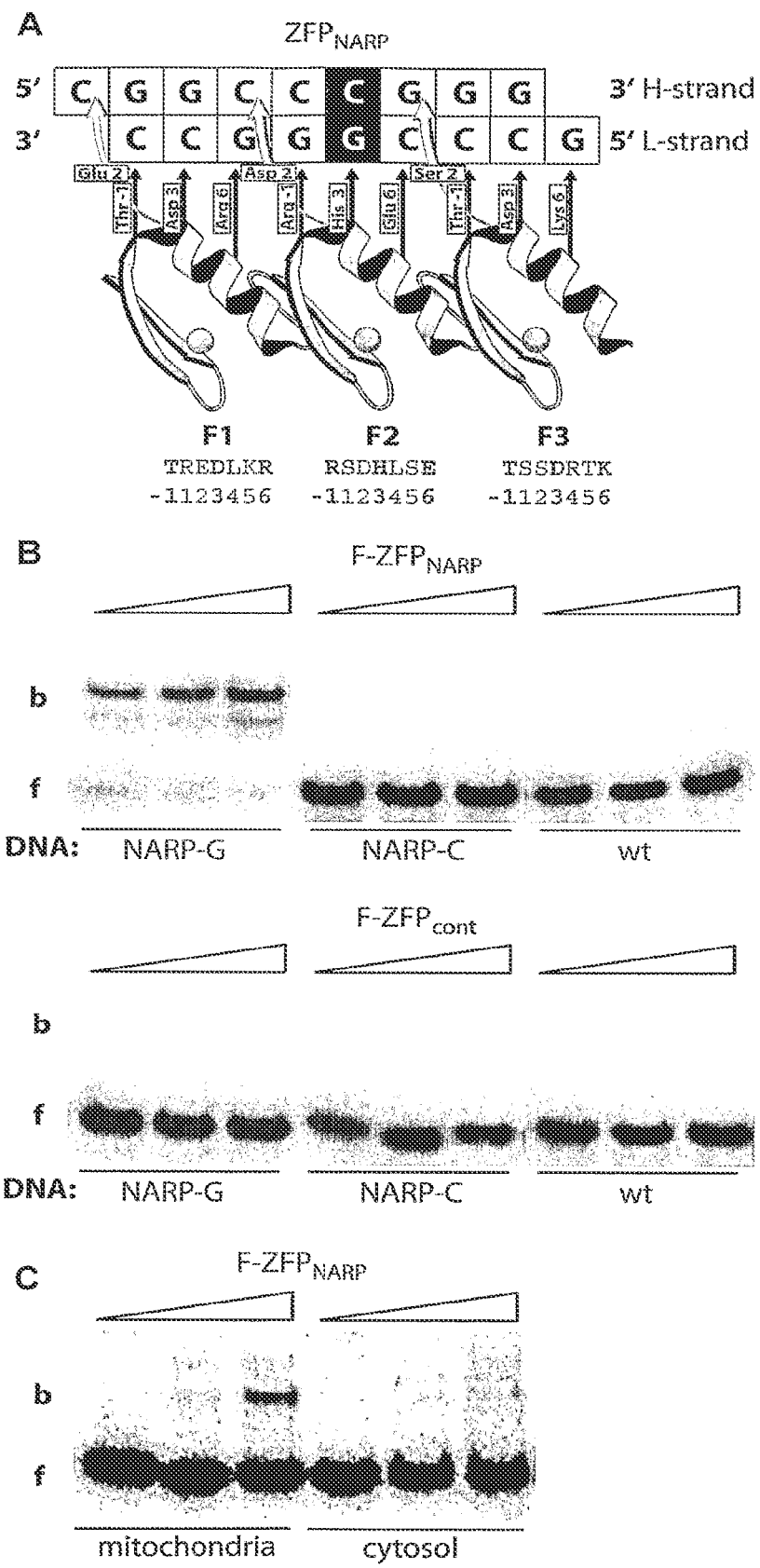

Construction of a Mitochondria-Targeted ZFP that Binds a Particular mtDNA Sequence The next step was to generate ZFPs that bound selectively to particular mtDNA sequences. To this end we created a mitochondrially targeted 3-finger protein F-ZFPNARP designed to bind a 9 bp sequence GCCCGGGCC in mtDNA (FIG. 2A); the bold G is at position 8993 in mtDNA and indicates a mutation responsible for the mitochondrial diseases—Neurogenic muscle weakness, Ataxia and Retinitis Pigmentosa (NARP) and maternally-inherited Leigh syndrome (MILS). The wild type (wt) sequence has a T at this position. In vitro FZFPNARP specifically bound an oligonucleotide containing GCCCGGGCC, as assessed by a gel retardation assay (FIG. 2B). In contrast, oligonucleotides containing either GCCCTGGCC (wt) or GCCCCGGCC were not bound by F-ZFPNARP (FIG. 2B). Additionally, in vitro binding studies of ZFPs showed that the addition of NES did not affect DNA binding (data not shown). A control, F-ZFPcont, of the same size as FZFPNARP did not bind to any of the three DNA sequences tested (FIG. 2B) hence could be further used as a control for any non sequence-specific effects of targeting a ZFP to mitochondria. Therefore, F-ZFPNARP binds highly specifically to a sequence containing the T8993G mutation, but not to wt mtDNA that differs by a single bp.

It was unclear whether an exogenous ZFP would incorporate zinc and fold correctly within the mitochondria. This was addressed by using the mitochondrial extract from the cells expressing F-ZFPNARP for binding studies in vitro (FIG. 2C). These experiments showed that mitochondria from these cells contained a DNA binding activity that bound GCCCGGGCC in the same way as F-ZFPNARP expressed in vitro. This was not due to non-specific DNA binding, as the mitochondrial extracts from the cells expressing F-ZFPcont did not retard these DNA oligomers (data not shown). Therefore ZFPs can be delivered to mitochondria within cells where they retain in active form capable of selective binding of target DNA sequences.

Example 3

Targeting a Chimaeric ZFP-Methylase to a Particular mtDNA Sequence

The next step was to investigate whether F-ZFPNARP could direct a DNA modifying activity selectively to the mutant GCCCGGGCC mtDNA sequence. As a DNA modifying activity we chose the catalytic domain of the human DNMT3a DNA methyltransferase. This enzyme predominately methylates cytosines in CpG sites to 5-methylcytosine (m5C), using S-adenosylmethionine (SAM) as a substrate. Chimaeric proteins comprising Zif268-derived ZFPs and the catalytic DNA methyltransferase domains have previously been shown to catalyse sequence specific DNA methylation in vitro (Xu, G. L. & Bestor, T. H. Nat Genet 17, 376-8 (1997); McNamara, A. R., Hurd, P. J., Smith, A. E. & Ford, K. G. Nucleic Acids Res 30, 3818-30 (2002)) and in vivo (Carvin, C. D., Parr, R. D. & Kladde, M. P. Nucleic Acids Res 31, 6493-501 (2003)). Endogenous cytosine methylation in human mtDNA is very limited (Shmookler Reis, R. J. & Goldstein, S. Biol Chem 258, 9078-85 (1983); Maekawa, M. et al. Clin Chem 50, 1480-1 (2004)) but SAM is present within mitochondria (Agrimi, G. et al. Biochem J 379, 183-90 (2004)). The main advantage of using a methylase is that its activity can be easily assessed by the extent of sequence specific 5C methylation (Frommer, M. et al. Proc Natl Acad Sci USA 89, 1827-31 (1992)).

Figure 6:
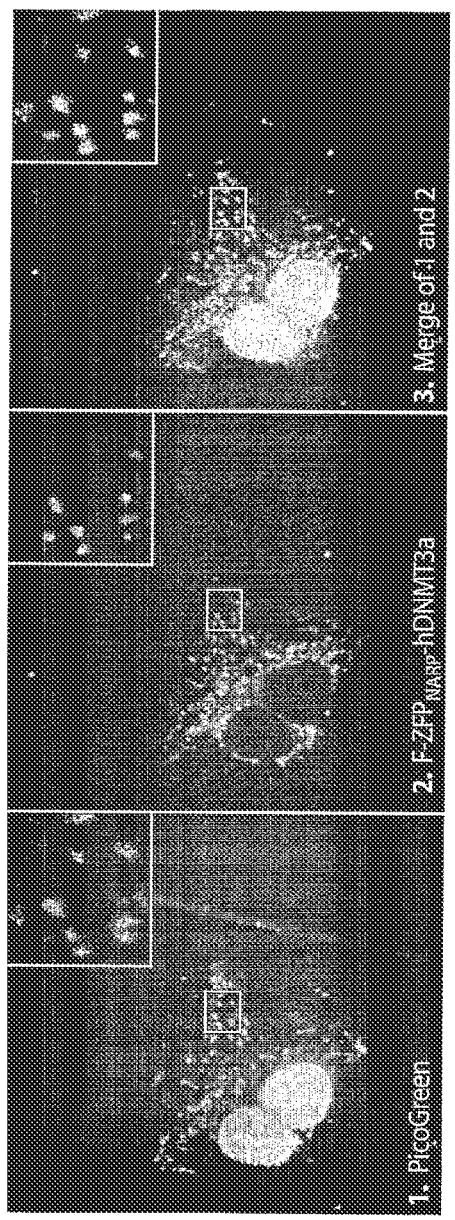

The F-ZFPNARP construct was fused to the methylase domain of the human DNMT3a (meth) using a flexible linker- and C-terminal NES to give F-ZFPNARP-meth-NES (FIG. 3A). When F-ZFPNARP-meth-NES was expressed in human cells we found that the MTS F is cleaved off from the mature protein, which is consistent with uptake through the conventional mitochondrial import pathway. The mature form of FZFPNARP-meth-NES was protected from proteolysis, to the same extent as the mitochondrial matrix protein mtTFAM (Kang, D. & Harnasaki, N Ann N Y Acad Sci 1042, 101-8 (2005)), when the isolated mitochondria were incubated with Proteinase K, while GAPDH—the protein associated with the mitochondrial outer membrane (Hartmann, C. M., Gehring, H. & Christen, P. Eur J Biochem 218, 905-10 (1993); Taylor, S. W. et al. Nat Biotechnol 21, 281-6 (2003))—was degraded (FIG. 3B). Additional immunofluorescence experiments showed that F-ZFPNARP-meth-NES colocalised with MitoTracer Red within mitochondria in a punctate pattern (FIG. 3C, 1-3), which is typical of resident proteins found in the mitochondrial nucleoid (Garrido, N. et al. Mol Biol Cell 14, 1583-96 (2003)). Its localisation in the nucleoid was confirmed by comparing its distribution with that of the mitochondrial transcription factor, mtTFAM (FIG. 3C, 4-6) and also the mitochondrial single-strand DNA binding protein mtSSB (not shown), which are known to be part of the nucleoid (Garrido, N. et al. Mol Biol Cell 14, 1583-96 (2003)). The final confirmation came from showing that F-ZFPNARP-meth-NES colocalised with mtDNA itself labelled with BrdU (FIG. 3C; 7-9) or PicoGreen (see FIG. 6). Therefore, the F-ZFPNARP-meth-NES is taken up by mitochondria within cells and localises to the mtDNA in the matrix.

Example 4

Sequence-Specific In Vivo Methylation of mtDNA by a Chimaeric ZFP-Methylase

Figure 4:
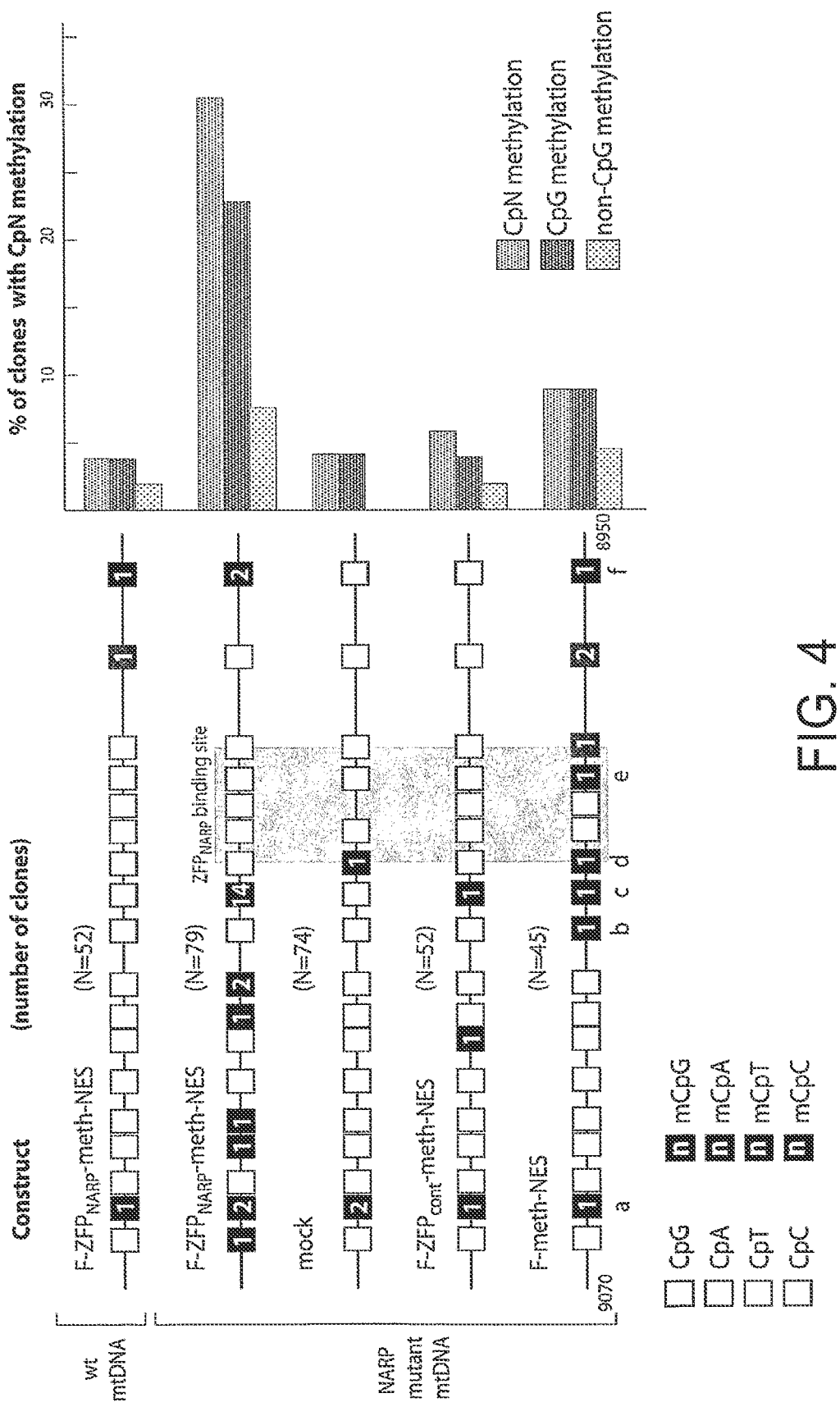
Figure 8:
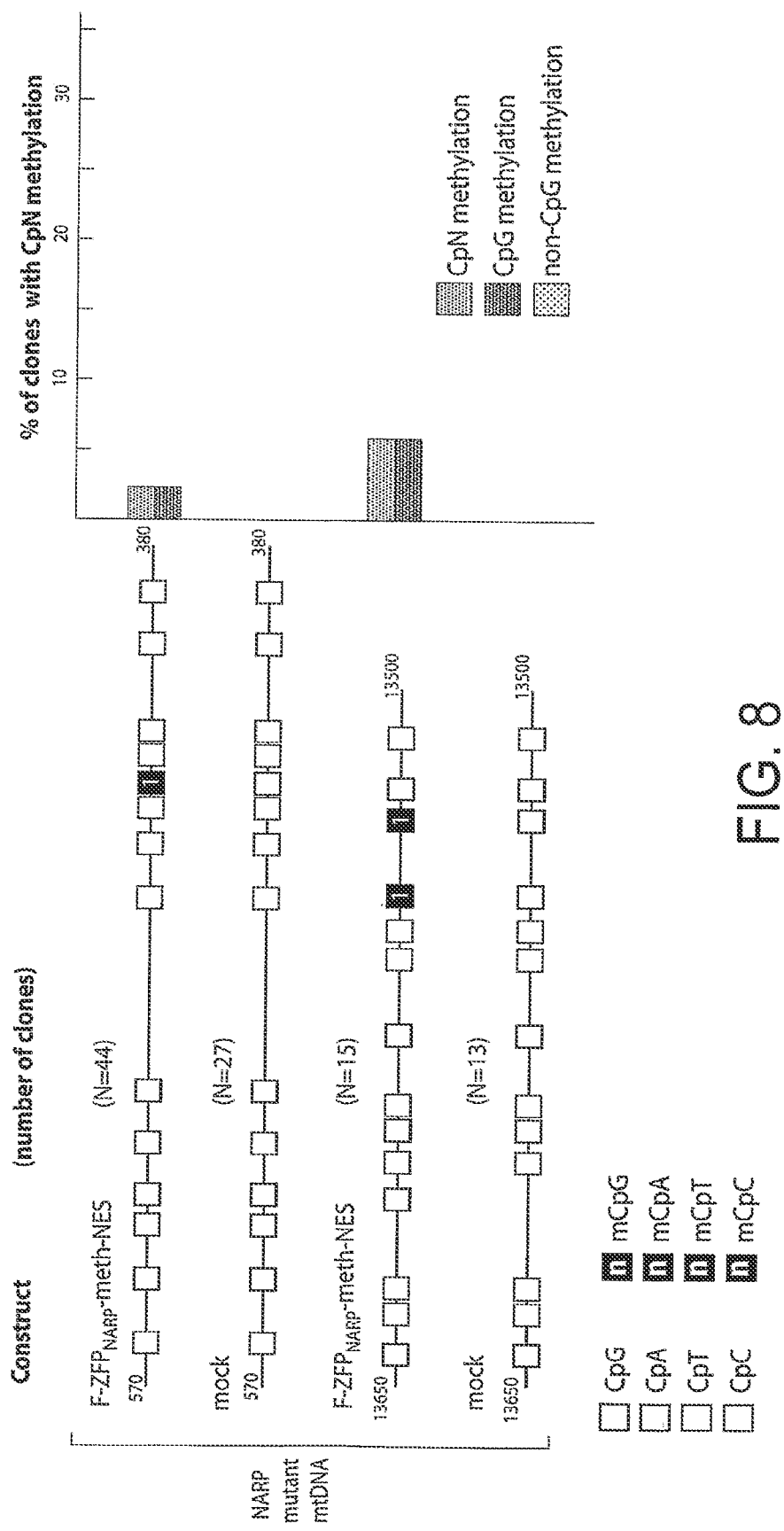

The final goal was to determine whether F-ZFPNARP-meth-NES selectively increased the 5C methylation of cytosines in CpG sites adjacent to the targeted GCCCGGGCC sequence. The F-ZFPNARP-meth-NES construct was expressed in NARP cells, which contain a G at position 8993 in their mtDNA has and also in wt cells which have T at this position. To assess the sequence specificity of mtDNA methylation by F-ZFPNARP-meth-NES we used the bisulphite method (Frommer, M. et al. Proc Natl Acad Sci USA 89, 1827-31 (1992)). This technique consists of treating DNA with bisulphite to convert all cytosines to uracils while leaving m5C unchanged. Total DNA from either wt or NARP cells transfected with F-ZFPNARP-meth-NES or control construct (FIG. 4) was extracted and a 120 bp fragment of bisulphite converted mtDNA H-strand containing the GCCCGGGCC sequence of interest was then amplified by PCR and cloned. A statistically significant number of clones from two independent experiments were randomly chosen for each construct, sequenced and compared to the control sequence to indicate which cytosines had been methylated (see FIGS. 7 and 8). Methylation of CpG dinucleotides surrounding the GCCCGGGCC sequence was observed in 23% of clones derived from the NARP cells expressing F-ZFPNARP-meth-NES (FIG. 4, right). In contrast, in wt cells expressing F-ZFPNARP-meth-NES the extent of CpG methylation in the analogous region was ~6-fold lower and was indistinguishable from background levels of CpG methylation. Similarly, when the F-ZFPcont-meth-NES was expressed in the NARP cells there was a ~6-fold lower level of CpG methylation in the analysed region. A mitochondrially targeted methylase domain without a ZFP, F-meth-NES (see FIG. 3A), was expressed in the NARP cells and also caused far lower CpG methylation level (~2.6-fold) then F-ZFPNARP-meth-NES. Furthermore, the F-meth-NES control showed methylated CpG sites spread throughout the entire analysed region (FIG. 4, left). The lower methylation levels observed for F-ZFPcon-tmeth-NES or F-ZFPNARP-meth-NES expressed in the wt cells as compared to F-meth-NES might be due to the attenuation of the methyltransferase DNA affinity by fusion to the ZFPs as reported previously (Xu, G. L. & Bestor, T. H. Nat Genet 17, 376-8 (1997)). These controls indicate that the increased CpG methylation around GCCCGGGCC sequence upon expression of F-ZFPNARP-meth-NES, was not a simple consequence of the presence of a methylase in mitochondria. Furthermore, the increased CpG methylation is a result of the sequence specific binding of F-ZFPNARP-meth-NES to the GCCCGGGCC sequence as there was no increase in CpG methylation in other regions of mtDNA well away from this site (regions 380-570 and 13500-13650).

There was a high preference of F-ZFPNARP-meth-NES mediated methylation (~18% of clones) for the CpG site 3 bp downstream from the GCCCGGGCC (marked CpG-c in FIG. 4, left). In contrast, there was no methylation of the CpG located 11 bp downstream from the GCCCGGGCC (CpG-b in FIG. 4, left). The highly methylated CpG-c site is in the most favourable sequence context for the hDNMT3a methylase (ACGC), whereas the unmethylated CpG-b is flanked by the least preferred nucleotides (CCGC) (Handa, V. & Jeltsch, A. J Mol Biol 348, 1103-12 (2005)). In addition, methylation catalysed by hDNMT3a is asymmetric and shows a strong strand preference (Lin, I. G., Han, L., Taghva, A., O'Brien, L. E. & Hsieh, C. L. Mol Cell Biol 22, 704-23 (2002)). Therefore, it is possible that the methylation of CpG-b occurs predominately on the L-strand and therefore was not detected by bisulphite sequencing here, which is difficult to apply to the L-strand due to its high pyrimidine content. There was no methylation of the two CpG dinucleotides in the GCCCGGGCC sequence (marked as d and e in FIG. 4) where F-ZFPNARP-meth-NES binds. However, methylation of these CpG sites was detected in mock and F-meth-NES transfected cells. This is consistent with protection from methylation of these CpG sites by F-ZFP-NARP-meth-NES binding. The above findings suggest that F-ZFPNARP-meth-NES binds to the GCCCGGGCC sequence and that a flexible linker enables the methylase to preferentially access the CpG-c (FIG. 4). In vitro the Zif268-M.SssI fusion preferably methylated cytosines in CpG sites located 16 to 22 bp upstream from its binding site (Xu, G. L. & Bestor, T. H. Nat Genet 17, 376-8 (1997)) while in yeast Zif268-M.SssI methylated CpGs located 5 to 52 bp on the both sides of the binding site with a strong site preference (Carvin, C. D., Parr, R. D. & Kladde, M. P. Nucleic Acids Res 31, 6493-501 (2003)). Therefore, our results are consistent with the previous in vivo studies of methylates conjugated to a ZFPs. Interaction with endogenous protein(s), the flexibility of the linker separating the methylase domain and ZFP as well as the relation of the helical face of particular CpG to the targeted methylase bound to DNA could contribute to the preferential in vivo methylation of some sites.

In the NARP cells expressing F-ZFPNARP-meth-NES cytosine methylation was often accompanied by base substitutions in the vicinity of the GCCCGGGCC sequence (data not shown). These mutations were not detected in non-methylated clones of either NARP or wt cells. It is possible that either the binding of F-ZFPNARPmeth-NES to its target site and/or the methylation of mtDNA, affects the fidelity of mtDNA replication in this region. This issue is being currently investigated.

Our studies also indicated enhanced methylation in CpA, CpT and CpC dinucleotides, in approximately 4%, 2.5% and 1% of clones respectively, in the vicinity of the GCCCGGGCC in cells expressing F-ZFPNARP-meth-NES (FIG. 4). In contrast, far lower levels of non-CpG methylation were observed in this region in wt cells expressing F-ZFPNARP-meth-NES, or in NARP cells expressing either F-ZFP contmeth-NES or F-meth-NES (FIG. 4). This result is consistent with reports that the DNMT3a methylase can also methylate cytosines in non-CpG dinucleotides in vivo and in vitro, albeit much less effectively (Gowher, H. & Jeltsch, A. J Mol Biol 309, 1201-8 (2001); Aoki, A. et al. Nucleic Acids Res 29, 3506-12 (2001); Mund, C. et al. Biochem J 378, 763-8 (2004); Ramsahoye, B. H. et al. Proc Natl Acad Sci USA 97, 5237-42 (2000). Additionally, the overall relative proportions of methylation found in the dinucleotides CpG, CpA, CpT, CpC agree well with the known propensities of the DNMT3a methylase for these sites. Elevated non-CpG methylation of the region surrounding the targeted GCCCGGGCC sequence could therefore be a result of a high concentration of the enzyme directed there by the ZFP. In summary, we have shown sequence specific methylation of sites in mtDNA by the targeted methylase.

DISCUSSION

We have shown that it is possible to target an enzymatically active chimaeric ZFP to mitochondria. A conventional MTS was not sufficient to ensure reliable mitochondrial localisation and we had to incorporate a NES into the C-terminus of the fusion protein in conjunction with the MTS. This re-routing strategy proved effective at ensuring that the ZFPs were directed exclusively to the mitochondria. As well as being essential for the use of mitochondria-targeted ZFPs this strategy of incorporating a C-terminus NES may be of general use in targeting proteins to mitochondria and to other organelles where nuclear localisation is problematic. Within the mitochondria, the ZFP folded correctly and bound the appropriate DNA sequence with the same sequence discrimination as in the in vitro studies. Importantly, this ZFP when expressed in the mitochondria could discriminate between mutant and wt mtDNA differing by a single point mutation out of nine base pairs recognised, similarly to previously reported nuclear ZFPs (Choo, Y., Sanchez-Garcia, I. & Klug, A. Nature 372, 642-5 (1994)). The ZFP targeted a DNA-modifying enzyme activity to a particular location on the mtDNA. The activity chosen here, as a proof of principle, was a methylase domain, because the sequence specific methylation can be easily assessed to confirm whether the activity is truly sequence dependent. This confirmed that conjugation of the methylase to the ZFP led to the sequence specific modification of mtDNA. As it is possible to design a wide range of ZFPs with various sequence specificities, the approach reported here could be useful for selective targeting of a large range of DNA sequences within the mitochondria. This would enable ZFPs to be attached to particular effector domains and then directed to bind to predetermined DNA sequences in mitochondria. For example, a ZFP conjugated to a nuclease domain could be used to selectively degrade mutated leaving the wt mtDNA intact. This could be used as a potential therapy for heteroplasmic mitochondrial diseases One possible therapeutic strategy for these diseases could be based on the selective inhibition of replication of mutated mtDNA. By lowering a copy number of the mutated mtDNA the cell could become re-populated by wt mtDNA thus restoring mitochondrial function and eliminating the disease phenotype. Another application would be to investigate regulatory regions for mtDNA replication and transcription. In summary, we have developed a methodology for targeting various activities to particular sequences of mtDNA by conjugation to sequence specific ZFPs.

All publications mentioned in the above specification are herein incorporated by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are readily apparent to those skilled in molecular biology or related fields are intended to be within the scope of the following claims.

What is claimed is:

1. A fusion protein that binds to a point mutation in mutant mitochondrial DNA (mtDNA), the fusion protein comprising:
   (a) a zinc finger protein (ZFP) DNA-binding polypeptide comprising 3 zinc fingers, wherein the ZFP binds specifically to a target sequence in the mutant mtDNA, wherein the target sequence comprises the point mutation;
   (b) a functional domain which modifies the mutant mtDNA;
   (c) a mitochondrial targeting sequence (MTS); and
   (d) a nuclear export sequence (NES), wherein the fusion protein is localized in a mitochondria of a cell.

2. A fusion protein according to claim 1, wherein the functional domain is obtained from a protein selected from the group consisting of a methylase and a restriction endonuclease.

3. A fusion protein according to claim 2, wherein the functional domain is the DNA cleavage domain of the endonuclease.

4. A fusion protein according to claim 2, wherein the endonuclease is a Type IIs restriction endonuclease.

5. A pharmaceutical composition comprising a fusion protein according to claim 1.

6. A fusion protein according to claim 1, wherein the functional domain is a transcriptional activation or transcriptional repression domain.

7. A fusion protein according to claim 6, wherein the functional domain is obtained from a DNA-modifying enzyme.

8. A fusion protein according to claim 1, wherein the MTS is the signal peptide of a mitochondrial protein.

9. A fusion protein according to claim 1, wherein the MTS is obtained from a protein selected from the group consisting of: human cytochrome c oxidase subunit VIII, the P1 isoform of subunit c of human ATP synthase, the F1β subunit of human ATP synthase, the aldehyde dehydrogenase targeting sequence and the BCS1 protein.

10. A fusion protein according to claim 1, wherein the NES is obtained from a protein selected from the group consisting of: Non-structural protein 2 of MNV, Protein Kinase Inhibitor, HIV-I Rev, MAP kinase kinase, MVM N52, An3, IKBa, Cyclin B I and TFIIIA.

11. A fusion protein according to claim 1, wherein the NES is selected from the group consisting of: SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20.

12. A fusion protein according to claim 1, wherein the mutant mtDNA is associated with a disease.

13. A fusion protein according to claim 12, wherein the disease is selected from the group consisting of LHON (Leber Hereditary Optic Neuropathy), MM (Mitochondrial Myopathy), AD (Alzeimer's Disease), LIMM (Lethal Infantile Mitochondrial Myopathy), ADPD (Alzeimer's Disease and Parkinson's Disease), MMC (Maternal Myopathy and Cardiomyopathy), NARP (Neurogenic muscle weakness, Ataxia, and Retinitis Pigmentosa; alternate phenotype at this locus reported as Leigh Disease), FICP (Fatal Infantile Cardiomyopathy Plus, a MELAS-associated cardiomyopathy), MELAS (Mitochondrial Encephalomyopathy, Lactic Acidosis, and Stroke-like episodes), LDYT (Leber's hereditary optic neuropathy and DysTonia), MERRF (Myoclonic Epilepsy and Ragged Red Muscle Fibers), MHCM (Maternally inherited Hypertrophic CardioMyopathy), CPEO (Chronic Progressive External Ophthalmoplegia), KSS (Kearns Sayre Syndrome), DM (Diabetes Mellitus), DMDF (Diabetes Mellitus+DeaFness), CIPO (Chronic Intestinal Pseudoobstruction with myopathy and Ophthalmoplegia), DEAF (Maternally inherited DEAFness or aminoglycoside-induced DEAFness), PEM (Progressive encephalopathy), SNHL (SensoriNeural Hearing Loss), aging, encephalomyopathy, FBSN (familial bilateral striatal necrosis), PEO, and SNE (subacute necrotizing encephalopathy).

\* \* \* \* \*

SEQUENCE LISTING

```
<160> NUMBER OF SEQ ID NOS: 116

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      leader peptide

<400> SEQUENCE: 1

Met Ala Glu Glu Lys Pro
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 2

Gly Glu Lys Pro
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 3

Gly Glu Arg Pro
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 4

Gly Gln Lys Pro
1
```

```
<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 5

Gly Gln Arg Pro
1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 6

Gly Gly Glu Lys Pro
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 7

Gly Gly Gln Lys Pro
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 8

Gly Gly Ser Gly Glu Lys Pro
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 9

Gly Gly Ser Gly Gln Lys Pro
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide
```

-continued

```
<400> SEQUENCE: 10

Gly Gly Ser Gly Gly Ser Gly Glu Lys Pro
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 11

Gly Gly Ser Gly Gly Ser Gly Gln Lys Pro
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      nuclear export signal (NES) peptide

<400> SEQUENCE: 12

Leu Ala Leu Lys Leu Ala Gly Leu Asp Ile Asn
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      nuclear export signal (NES) peptide

<400> SEQUENCE: 13

Leu Gln Leu Pro Pro Leu Glu Arg Leu Thr Leu Asp
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      nuclear export signal (NES) peptide

<400> SEQUENCE: 14

Leu Gly Leu Lys Leu Glu Glu Leu Glu Leu Glu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      nuclear export signal (NES) peptide

<400> SEQUENCE: 15

Met Thr Lys Lys Phe Gly Thr Leu Thr Ile
1               5                   10

<210> SEQ ID NO 16
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      nuclear export signal (NES) peptide

<400> SEQUENCE: 16

Leu Ala Glu Met Leu Glu Asp Leu His Ile
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      nuclear export signal (NES) peptide

<400> SEQUENCE: 17

Leu Asp Gln Gln Phe Ala Gly Leu Asp Leu
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      nuclear export signal (NES) peptide

<400> SEQUENCE: 18

Met Val Lys Glu Leu Gln Glu Ile Arg Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      nuclear export signal (NES) peptide

<400> SEQUENCE: 19

Leu Cys Gln Ala Phe Ser Asp Val Ile Leu
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      nuclear export signal (NES) peptide

<400> SEQUENCE: 20

Leu Pro Val Leu Glu Asn Leu Thr Leu
1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      c-myc epitope tag

<400> SEQUENCE: 21

Glu Gln Lys Leu Ile Ser Glu Glu Asp Leu
```

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      HA eptitope tag

<400> SEQUENCE: 22

Tyr Pro Tyr Asp Val Pro Asp Tyr Ala
1               5

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      NES peptide from NS2 protein of MVM

<400> SEQUENCE: 23

Val Asp Glu Met Thr Lys Lys Phe Gly Thr Leu Thr Ile His Asp Thr
1               5                   10                  15

Glu Lys

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 24

Ser Gly Gly Gly Gly Ser Gly Gly Gly Ser Gly Gly Gly Gly Ser
1               5                   10                  15

Ser

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 25

Arg Ser Asp Val Leu Ser Ala
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 26

Arg Asn Asp His Arg Ile Asn
1               5

<210> SEQ ID NO 27
<211> LENGTH: 7

```
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 27

Arg Ser Asp Thr Leu Ser Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 28

His Asn His His Arg Lys Thr
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 29

Arg Ser Asp His Leu Ser Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 30

His Ser Asn Thr Arg Lys Asn
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 31

Arg Ser Asp Ser Leu Ser Thr
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 32

Ala Gly Ala Asn Arg Thr Thr
```

```
1               5
```

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 33

```
Arg Ser Asp Val Leu Ser Val
1               5
```

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 34

```
Thr Asn Gln His Arg Thr Lys
1               5
```

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 35

```
Arg Ser Asp His Leu Ser Glu
1               5
```

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 36

```
Asn Asn Ser Ser Arg Thr Arg
1               5
```

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 37

```
Arg Ser Asp His Leu Ser Gln
1               5
```

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic zinc finger peptide

<400> SEQUENCE: 38

Thr Ser Ser Asn Arg Lys Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 39

Arg Ser Asp His Leu Ser Asn
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 40

Arg Ser Asp Asp Arg Lys Lys
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 41

Arg Lys Asp Ala Arg Ile Thr
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 42

Arg Asn Asp Asp Arg Lys Lys
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 43

Gln Ser Ala Thr Arg Ile Thr
1               5

<210> SEQ ID NO 44

```
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 44

Arg Ser Asp Asn Leu Ser Thr
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 45

Arg Ser Asp Asn Arg Thr Lys
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 46

Asp Ser Ser His Arg Thr Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 47

Arg Ser Asp Ser Leu Ser Val
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 48

Gln Asn Gln His Arg Ile Asn
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 49
```

Arg Asn Asp Asn Arg Lys Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 50

Thr Ser Ala Asn Arg Thr Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 51

Arg Ser Asp Ser Leu Ser Gln
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 52

Asn Ser Ser Asn Arg Lys Asn
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 53

Thr Arg Asp Thr Arg Lys Lys
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 54

Arg Ser Asp Ala Leu Ser Val
1               5

<210> SEQ ID NO 55
<211> LENGTH: 7
<212> TYPE: PRT
<213> ORGANISM: Artificial Sequence
<220> FEATURE:

```
<223> OTHER INFORMATION: Description of Artificial Sequence: Synthetic
      zinc finger peptide

<400> SEQUENCE: 55

Arg Ser Asp Thr Leu Ser Glu
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 56

Arg Asn Asp His Arg Thr Thr
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 57

Arg Arg Asp Ser Arg Thr Asn
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 58

Gln Asn Asn His Arg Ile Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 59

Ala Ser Ser Ala Arg Lys Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 60

His Ser Asp Thr Arg Thr Lys
1               5
```

```
<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 61

Arg Ser Asp His Leu Thr Lys
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 62

Asn Ser Asp His Leu Ser Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 63

Thr Asn Asp Asp Leu Asn Thr
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 64

Thr Ser Ser His Leu Ser Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      Zinc finger alpha-helix peptide

<400> SEQUENCE: 65

Thr Arg Glu Asp Leu Lys Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      Zinc finger alpha-helix peptide

<400> SEQUENCE: 66
```

```
Thr Ser Ser Asp Arg Thr Lys
1               5

<210> SEQ ID NO 67
<211> LENGTH: 116
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 67

Met Ala Glu Arg Pro Phe Ile Arg Ile Cys Met Arg Asn Phe Ser Arg
1               5                   10                  15

Ser Asp Val Leu Ser Ala His Ile Arg Thr His Ala Gly Glu Lys Pro
            20                  25                  30

Phe Ala Cys Asp Ile Cys Gly Lys Lys Phe Ala Arg Asn Asp His Arg
        35                  40                  45

Ile Asn His Thr Lys Ile Asp Thr Gly Ser Gln Lys Pro Phe Gln Cys
50                  55                  60

Arg Ile Cys Met Arg Asn Phe Ser Arg Ser Asp Thr Leu Ser Arg His
65                  70                  75                  80

Ile Arg Thr His Thr Gly Glu Lys Pro Phe Ala Cys Asp Ile Cys Gly
                85                  90                  95

Arg Lys Phe Ala His Asn His Arg Lys Thr His Thr Lys Ile His
            100                 105                 110

Leu Arg Gln Lys
        115

<210> SEQ ID NO 68
<211> LENGTH: 120
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 68

Met Ala Glu Arg Pro Phe Gln Cys Arg Ile Cys Met Arg Asn Phe Ser
1               5                   10                  15

Arg Ser Asp His Leu Ser Thr His Ile Arg Thr His Thr Gly Glu Lys
            20                  25                  30

Pro Phe Ala Cys Asp Ile Cys Gly Arg Lys Phe Ala His Ser Asn Thr
        35                  40                  45

Arg Lys Asn His Thr Lys Ile His Thr Gly Gly Gly Ser Gln Lys
50                  55                  60

Pro Phe Gln Cys Arg Ile Ser Met Arg Asn Phe Ser Arg Ser Asp Ser
65                  70                  75                  80

Leu Ser Thr His Ile Arg Thr His Thr Gly Glu Lys Pro Phe Ala Cys
                85                  90                  95

Asp Ile Cys Gly Arg Lys Phe Ala Ala Gly Ala Asn Arg Thr Thr His
            100                 105                 110

Thr Lys Ile His Leu Arg Gln Lys
        115                 120

<210> SEQ ID NO 69
<211> LENGTH: 117
<212> TYPE: PRT
<213> ORGANISM: Artificial Sequence
```

-continued

```
<220> FEATURE:
<223> OTHER INFORMATION: Description of Artificial Sequence: Synthetic
      zinc finger polypeptide

<400> SEQUENCE: 69

Met Ala Glu Arg Pro Phe Gln Cys Arg Ile Cys Met Arg Asn Phe Ser
1               5                   10                  15

Arg Ser Asp Val Leu Ser Val His Ile Arg Thr His Thr Gly Glu Lys
            20                  25                  30

Pro Phe Ala Cys Asp Ile Cys Gly Lys Lys Phe Ala Thr Asn Gln His
        35                  40                  45

Arg Thr Lys His Thr Lys Ile His Thr Gly Ser Gln Lys Pro Phe Gln
    50                  55                  60

Cys Arg Ile Cys Met Arg Asn Phe Ser Arg Ser Asp His Leu Ser Glu
65                  70                  75                  80

His Ile Arg Thr His Thr Gly Glu Lys Pro Phe Ala Cys Asp Ile Cys
                85                  90                  95

Gly Arg Lys Phe Ala Asn Asn Ser Ser Arg Thr Arg His Thr Lys Ile
            100                 105                 110

His Leu Arg Gln Lys
            115

<210> SEQ ID NO 70
<211> LENGTH: 117
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 70

Met Ala Glu Arg Pro Phe Gln Cys Arg Ile Cys Met Arg Asn Phe Ser
1               5                   10                  15

Arg Ser Asp His Leu Ser Gln His Ile Arg Thr His Thr Gly Glu Lys
            20                  25                  30

Pro Phe Ala Cys Asp Ile Cys Gly Arg Lys Phe Ala Thr Ser Ser Asn
        35                  40                  45

Arg Lys Thr His Thr Lys Ile His Thr Gly Ser Gln Lys Pro Phe Gln
    50                  55                  60

Cys Arg Ile Cys Met Arg Asn Phe Ser Arg Ser Asp His Leu Ser Asn
65                  70                  75                  80

His Ile Arg Thr His Thr Gly Glu Lys Pro Phe Ala Cys Asp Ile Cys
                85                  90                  95

Gly Arg Lys Phe Ala Arg Ser Asp Asp Arg Lys Lys His Thr Lys Ile
            100                 105                 110

His Leu Arg Gln Lys
            115

<210> SEQ ID NO 71
<211> LENGTH: 120
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 71

Met Ala Glu Arg Pro Phe Gln Cys Arg Ile Cys Met Arg Asn Phe Ser
1               5                   10                  15
```

Arg Ser Asp His Leu Ser Glu His Ile Arg Thr His Thr Gly Glu Lys
            20                  25                  30

Pro Phe Ala Cys Asp Ile Cys Gly Arg Lys Phe Ala Arg Lys Asp Ala
            35                  40                  45

Arg Ile Thr His Thr Lys Ile His Thr Gly Gly Gly Ser Gln Lys
    50                  55                  60

Pro Phe Gln Cys Arg Ile Cys Met Arg Asn Phe Ser Arg Ser Asp His
65              70                  75                  80

Leu Ser Asn His Ile Arg Thr His Thr Gly Glu Lys Pro Phe Ala Cys
                85                  90                  95

Asp Ile Cys Gly Arg Lys Phe Ala Arg Ser Asp Asp Arg Lys Lys His
            100                 105                 110

Thr Lys Ile His Leu Arg Gln Lys
        115                 120

<210> SEQ ID NO 72
<211> LENGTH: 115
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 72

Met Ala Glu Arg Pro Phe Gln Cys Arg Ile Cys Met Arg Asn Phe Ser
1               5                   10                  15

Arg Ser Asp His Leu Ser Asn His Ile Arg Thr His Thr Gly Glu Lys
            20                  25                  30

Pro Phe Ala Cys Asn Ile Cys Gly Arg Lys Phe Ala Arg Asn Asp Asp
            35                  40                  45

Arg Lys Lys His Thr Lys Ile His Thr Gly Ser Gln Lys Pro Phe Gln
    50                  55                  60

Cys Arg Ile Cys Met Arg Asn Phe Ser Arg Ser Asp His Leu Ser Asn
65              70                  75                  80

His Ile Arg Thr His Thr Gly Glu Lys Pro Phe Ala Cys Asp Ile Cys
                85                  90                  95

Gly Lys Lys Phe Ala Gln Ser Ala Thr Arg Ile Thr His Thr Lys Ile
            100                 105                 110

His Leu Arg
        115

<210> SEQ ID NO 73
<211> LENGTH: 117
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 73

Met Ala Glu Arg Pro Phe Gln Cys Arg Ile Cys Met Arg Asn Phe Ser
1               5                   10                  15

Arg Ser Asp His Leu Ser Gln His Ile Arg Thr His Thr Gly Glu Lys
            20                  25                  30

Pro Phe Ala Cys Asp Ile Cys Gly Arg Lys Phe Ala Thr Ser Ser Asn
            35                  40                  45

Arg Lys Thr His Thr Lys Ile His Thr Gly Ser Gln Lys Pro Phe Gln
    50                  55                  60

```
Cys Arg Ile Cys Met Arg Asn Phe Ser Arg Ser Asp Asn Leu Ser Thr
 65                  70                  75                  80

His Ile Arg Thr His Thr Gly Glu Lys Pro Phe Ala Cys Asp Ile Cys
                 85                  90                  95

Gly Arg Lys Phe Ala Arg Ser Asp Asn Arg Thr Lys His Thr Lys Ile
            100                 105                 110

His Leu Arg Gln Lys
        115
```

<210> SEQ ID NO 74
<211> LENGTH: 120
<212> TYPE: PRT
<213> ORGANISM: Artificial Sequence
<220> FEATURE:
<223> OTHER INFORMATION: Description of Artificial Sequence: Synthetic zinc finger polypeptide

<400> SEQUENCE: 74

```
Met Ala Glu Arg Pro Phe Gln Cys Arg Ile Cys Met Arg Asn Phe Ser
  1               5                  10                  15

Arg Ser Asp His Leu Ser Glu His Ile Arg Thr His Thr Gly Glu Lys
                 20                  25                  30

Pro Phe Ala Cys Asp Ile Cys Gly Arg Lys Phe Ala Asp Ser Ser His
             35                  40                  45

Arg Thr Arg His Thr Lys Ile His Thr Gly Gly Gly Ser Gln Lys
         50                  55                  60

Pro Phe Gln Cys Arg Ile Cys Met Arg Asn Phe Ser Arg Ser Asp Ser
 65                  70                  75                  80

Leu Ser Val His Ile Arg Thr His Thr Gly Glu Lys Pro Phe Ala Cys
                 85                  90                  95

Asp Ile Cys Gly Arg Lys Phe Ala Gln Asn Gln His Arg Ile Asn His
            100                 105                 110

Thr Lys Ile His Leu Arg Gln Lys
        115                 120
```

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic zinc finger polypeptide

<400> SEQUENCE: 75

```
Met Ala Glu Arg Pro Phe Gln Cys Arg Ile Cys Met Arg Asn Phe Ser
  1               5                  10                  15

Arg Ser Asp His Leu Ser Glu His Ile Arg Thr His Thr Gly Glu Lys
                 20                  25                  30

Pro Phe Ala Cys Asp Ile Cys Gly Lys Lys Phe Ala Arg Asn Asp Asn
             35                  40                  45

Arg Lys Arg His Thr Lys Ile His Thr Gly Ser Gln Lys Pro Phe Gln
         50                  55                  60

Cys Arg Ile Cys Met Arg Asn Phe Ser Arg Ser Asp His Leu Ser Gln
 65                  70                  75                  80

His Ile Arg Thr His Thr Gly Glu Lys Pro Phe Ala Cys Asp Ile Cys
                 85                  90                  95

Gly Arg Lys Phe Ala Thr Ser Ala Asn Arg Thr Thr His Thr Lys Ile
            100                 105                 110
```

```
His Leu Arg Gln Lys
        115

<210> SEQ ID NO 76
<211> LENGTH: 120
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 76

Met Ala Glu Arg Pro Phe Gln Cys Arg Ile Cys Met Arg Asn Phe Ser
1               5                   10                  15

Arg Ser Asp Ser Leu Ser Gln His Ile Arg Thr His Thr Gly Glu Lys
            20                  25                  30

Pro Phe Ala Cys Asp Ile Cys Gly Arg Lys Phe Ala Asn Ser Ser Asn
        35                  40                  45

Arg Lys Asn His Thr Lys Ile His Thr Gly Gly Gly Ser Gln Lys
    50                  55                  60

Pro Phe Gln Cys Arg Ile Cys Met Arg Asn Phe Ser Arg Ser Asp Ser
65                  70                  75                  80

Leu Ser Gln His Ile Arg Thr His Thr Gly Glu Lys Pro Phe Ala Cys
                85                  90                  95

Asp Ile Cys Gly Lys Lys Phe Ala Thr Ser Ser Asn Arg Lys Thr His
            100                 105                 110

Thr Lys Ile His Leu Arg Gln Lys
        115                 120

<210> SEQ ID NO 77
<211> LENGTH: 120
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 77

Met Ala Glu Arg Pro Phe Gln Cys Arg Ile Cys Met Arg Asn Phe Ser
1               5                   10                  15

Arg Ser Asp His Leu Ser Asn His Ile Arg Thr His Thr Gly Glu Lys
            20                  25                  30

Pro Phe Ala Cys Asp Ile Cys Gly Arg Lys Phe Ala Thr Arg Asp Thr
        35                  40                  45

Arg Lys Lys His Thr Lys Ile His Thr Gly Gly Gly Gly Ser Gln Lys
    50                  55                  60

Pro Phe Gln Cys Arg Ile Cys Met Arg Asn Phe Ser Arg Ser Asp Ala
65                  70                  75                  80

Leu Ser Val His Ile Arg Thr His Thr Gly Glu Lys Pro Phe Ala Cys
                85                  90                  95

Asp Ile Cys Gly Arg Lys Phe Ala Asp Ser Ser His Arg Thr Arg His
            100                 105                 110

Thr Lys Ile His Leu Arg Gln Lys
        115                 120

<210> SEQ ID NO 78
<211> LENGTH: 120
<212> TYPE: PRT
<213> ORGANISM: Artificial Sequence
<220> FEATURE:
```

<223> OTHER INFORMATION: Description of Artificial Sequence: Synthetic
     zinc finger polypeptide

<400> SEQUENCE: 78

Met Ala Glu Arg Pro Phe Gln Cys Arg Ile Cys Met Arg Asn Phe Ser
1               5                   10                  15

Arg Ser Asp Thr Leu Ser Glu His Ile Arg Thr His Thr Gly Glu Lys
            20                  25                  30

Pro Phe Ala Cys Asp Ile Cys Gly Arg Lys Phe Ala Arg Asn Asp His
        35                  40                  45

Arg Thr Thr His Thr Lys Ile His Thr Gly Gly Gly Ser Gln Lys
    50                  55                  60

Pro Phe Gln Cys Arg Ile Cys Met Arg Asn Phe Ser Arg Ser Asp His
65                  70                  75                  80

Leu Ser Asn His Ile Arg Thr His Thr Gly Glu Lys Pro Phe Ala Cys
                85                  90                  95

Asn Ile Cys Gly Arg Lys Phe Ala Arg Asn Asp Asp Arg Lys Lys His
            100                 105                 110

Thr Lys Ile His Leu Arg Gln Lys
        115                 120

<210> SEQ ID NO 79
<211> LENGTH: 117
<212> TYPE: PRT
<213> ORGANISM: Artificial Sequence
<220> FEATURE:
<223> OTHER INFORMATION: Description of Artificial Sequence: Synthetic
     zinc finger polypeptide

<400> SEQUENCE: 79

Met Ala Glu Arg Pro Phe Gln Cys Arg Ile Cys Met Arg Asn Phe Ser
1               5                   10                  15

Arg Ser Asp His Leu Ser Glu His Ile Arg Thr His Thr Gly Glu Lys
            20                  25                  30

Pro Phe Ala Cys Asp Ile Cys Gly Lys Lys Phe Ala Arg Asn Asp Asn
        35                  40                  45

Arg Lys Arg His Thr Lys Ile His Thr Gly Ser Gln Lys Pro Phe Gln
    50                  55                  60

Cys Arg Ile Cys Met Arg Asn Phe Ser Arg Ser Asp His Leu Ser Asn
65                  70                  75                  80

His Ile Arg Thr His Thr Gly Glu Lys Pro Phe Ala Cys Asn Ile Cys
                85                  90                  95

Gly Arg Lys Phe Ala Arg Asn Asp Asp Arg Lys Lys His Thr Lys Ile
            100                 105                 110

His Leu Arg Gln Lys
        115

<210> SEQ ID NO 80
<211> LENGTH: 117
<212> TYPE: PRT
<213> ORGANISM: Artificial Sequence
<220> FEATURE:
<223> OTHER INFORMATION: Description of Artificial Sequence: Synthetic
     zinc finger polypeptide

<400> SEQUENCE: 80

Met Ala Glu Arg Pro Phe Gln Cys Arg Ile Cys Met Arg Asn Phe Ser
1               5                   10                  15

Arg Ser Asp His Leu Ser Glu His Ile Arg Thr His Thr Gly Glu Lys

```
                    20                  25                  30

Pro Phe Ala Cys Asp Ile Cys Gly Arg Lys Phe Ala Arg Asn Asp His
            35                  40                  45

Arg Thr Thr His Thr Lys Ile His Thr Gly Ser Gln Lys Pro Phe Gln
        50                  55                  60

Cys Arg Ile Cys Met Arg Asn Phe Ser Arg Ser Asp His Leu Ser Glu
65                  70                  75                  80

His Ile Arg Thr His Thr Gly Glu Lys Pro Phe Ala Cys Asp Ile Cys
                85                  90                  95

Gly Arg Lys Phe Thr Arg Arg Asp Ser Arg Thr Asn His Thr Lys Ile
            100                 105                 110

His Leu Arg Gln Lys
        115

<210> SEQ ID NO 81
<211> LENGTH: 120
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 81

Met Ala Glu Arg Pro Phe Gln Cys Arg Ile Cys Met Arg Asn Phe Ser
1               5                   10                  15

Arg Ser Asp His Leu Ser Thr His Ile Arg Thr His Thr Gly Glu Lys
            20                  25                  30

Pro Phe Ala Cys Asp Ile Cys Gly Arg Lys Phe Ala His Ser Asn Thr
        35                  40                  45

Arg Lys Asn His Thr Lys Ile His Thr Gly Gly Gly Ser Gln Lys
    50                  55                  60

Pro Phe Gln Cys Arg Ile Cys Met Arg Asn Phe Ser Arg Ser Asp His
65                  70                  75                  80

Leu Ser Glu His Ile Arg Thr His Thr Gly Glu Lys Pro Phe Ala Cys
                85                  90                  95

Asp Ile Cys Gly Arg Lys Phe Ala Arg Asn Asp His Arg Thr Thr His
            100                 105                 110

Thr Lys Ile His Leu Arg Gln Lys
        115                 120

<210> SEQ ID NO 82
<211> LENGTH: 117
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 82

Met Ala Glu Arg Pro Phe Gln Cys Arg Ile Cys Met Arg Asn Phe Ser
1               5                   10                  15

Arg Ser Asp Val Leu Ser Val His Ile Arg Thr His Thr Gly Glu Lys
            20                  25                  30

Pro Phe Ala Cys Asp Ile Cys Gly Arg Lys Phe Ala Gln Asn Asn His
        35                  40                  45

Arg Ile Thr His Thr Lys Ile His Thr Gly Ser Gln Lys Pro Phe Gln
    50                  55                  60

Cys Arg Ile Cys Met Arg Asn Phe Ser Arg Ser Asp His Leu Ser Thr
```

```
                65                  70                  75                  80
His Ile Arg Thr His Thr Gly Glu Lys Pro Phe Ala Cys Asp Ile Cys
                    85                  90                  95
Gly Arg Lys Phe Ala Ala Ser Ser Ala Arg Lys Thr His Thr Lys Ile
                100                 105                 110
His Leu Arg Gln Lys
            115

<210> SEQ ID NO 83
<211> LENGTH: 117
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 83

Met Ala Glu Arg Pro Phe Gln Cys Arg Ile Cys Met Arg Asn Phe Ser
1               5                   10                  15
Arg Ser Asp Ala Leu Ser Val His Ile Arg Thr His Thr Gly Glu Lys
                20                  25                  30
Pro Phe Ala Cys Asp Ile Cys Gly Arg Lys Phe Ala His Ser Asp Thr
            35                  40                  45
Arg Thr Lys His Thr Lys Ile His Thr Gly Ser Gln Lys Pro Phe Gln
        50                  55                  60
Cys Arg Ile Cys Met Arg Asn Phe Ser Arg Ser Asp Val Leu Ser Val
65                  70                  75                  80
His Ile Arg Thr His Thr Gly Glu Lys Pro Phe Ala Cys Asp Ile Cys
                    85                  90                  95
Gly Arg Lys Phe Ala Gln Asn Asn His Arg Ile Thr His Thr Lys Ile
                100                 105                 110
His Leu Arg Gln Lys
            115

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 84

Met Ala Glu Arg Pro Tyr Ala Cys Pro Val Glu Ser Cys Asp Arg Arg
1               5                   10                  15
Phe Ser Arg Ser Asp His Leu Thr Lys His Ile Arg Ile His Thr Gly
                20                  25                  30
Gln Lys Pro Phe Gln Cys Arg Ile Cys Met Leu Asn Phe Ser Asn Ser
            35                  40                  45
Asp His Leu Ser Arg His Ile Arg Thr His Thr Gly Ser Gln Lys Pro
        50                  55                  60
Phe Gln Cys Arg Ile Cys Met Arg Asn Phe Ser Arg Ser Asp Ser Leu
65                  70                  75                  80
Ser Val His Ile Arg Thr His Thr Gly Glu Lys Pro Phe Ala Cys Asp
                    85                  90                  95
Ile Cys Gly Arg Lys Phe Ala Gln Asn Gln His Arg Ile Asn His Thr
                100                 105                 110
Lys Ile His Leu Arg
```

```
<210> SEQ ID NO 85
<211> LENGTH: 117
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 85

Met Ala Glu Arg Pro Tyr Ala Cys Pro Val Glu Ser Cys Asp Arg Arg
1               5                   10                  15

Phe Ser Arg Ser Asp His Leu Thr Lys His Ile Arg Ile His Thr Gly
                20                  25                  30

Gln Lys Pro Phe Gln Cys Arg Ile Cys Met Leu Asn Phe Ser Asn Ser
            35                  40                  45

Asp His Leu Ser Arg His Ile Arg Thr His Thr Gly Ser Gln Lys Pro
        50                  55                  60

Phe Gln Cys Arg Ile Cys Met Arg Asn Phe Ser Arg Ser Asp His Leu
65                  70                  75                  80

Ser Asn His Ile Arg Thr His Thr Gly Glu Lys Pro Phe Ala Cys Asp
                85                  90                  95

Ile Cys Gly Arg Lys Phe Ala Thr Arg Asp Thr Arg Lys Lys His Thr
            100                 105                 110

Lys Ile His Leu Arg
        115

<210> SEQ ID NO 86
<211> LENGTH: 120
<212> TYPE: PRT
<213> ORGANISM: Artificial Sequence
<220> FEATURE:
<223> OTHER INFORMATION: Description of Artificial Sequence: Synthetic
      zinc finger polypeptide

<400> SEQUENCE: 86

Met Ala Glu Arg Pro Tyr Ala Cys Pro Val Glu Ser Cys Asp Arg Arg
1               5                   10                  15

Phe Ser Thr Asn Asp Asp Leu Asn Thr His Ile Arg Ile His Thr Gly
                20                  25                  30

Gln Lys Pro Phe Gln Cys Arg Ile Cys Met Arg Asn Phe Ser Thr Ser
            35                  40                  45

Ser His Leu Ser Arg His Ile Arg Thr His Thr Gly Gly Gly Gly Ser
        50                  55                  60

Gln Lys Pro Phe Gln Cys Arg Ile Cys Met Arg Asn Phe Ser Arg Ser
65                  70                  75                  80

Asp His Leu Ser Glu His Ile Arg Thr His Thr Gly Glu Lys Pro Phe
                85                  90                  95

Ala Cys Asp Ile Cys Gly Lys Lys Phe Ala Arg Asn Asp Asn Arg Lys
            100                 105                 110

Arg His Thr Lys Ile His Leu Arg
        115                 120

<210> SEQ ID NO 87
<211> LENGTH: 117
<212> TYPE: PRT
<213> ORGANISM: Artificial Sequence
<220> FEATURE:
<223> OTHER INFORMATION: Description of Artificial Sequence: Synthetic
``` zinc finger polypeptide

<400> SEQUENCE: 87

Met Ala Glu Arg Pro Tyr Ala Cys Pro Val Glu Ser Cys Asp Arg Arg
1               5                   10                  15

Phe Ser Thr Asn Asp Asp Leu Asn Thr His Ile Arg Ile His Thr Gly
            20                  25                  30

Gln Lys Pro Phe Gln Cys Arg Ile Cys Met Arg Asn Phe Ser Thr Ser
        35                  40                  45

Ser His Leu Ser Arg His Ile Arg Thr His Thr Gly Ser Gln Lys Pro
    50                  55                  60

Phe Gln Cys Arg Ile Cys Met Arg Asn Phe Ser Arg Ser Asp His Leu
65                  70                  75                  80

Ser Glu His Ile Arg Thr His Thr Gly Glu Lys Pro Phe Ala Cys Asp
                85                  90                  95

Ile Cys Gly Arg Lys Phe Ala Arg Asn Asp His Arg Thr Thr His Thr
            100                 105                 110

Lys Ile His Leu Arg
        115

<210> SEQ ID NO 88
<211> LENGTH: 80
<212> TYPE: DNA
<213> ORGANISM: Artificial Sequence
<220> FEATURE:
<223> OTHER INFORMATION: Description of Artificial Sequence: Synthetic
      mtDNA H-strand polynucleotide

<400> SEQUENCE: 88
gtggcctgca gtaatgttag cggttaggcg tacggcccgg gctattggtt gaatgagtag      60
gctgatggtt tcgataataa                                                  80

<210> SEQ ID NO 89
<211> LENGTH: 80
<212> TYPE: DNA
<213> ORGANISM: Artificial Sequence
<220> FEATURE:
<223> OTHER INFORMATION: Description of Artificial Sequence: Synthetic
      mtDNA H-strand polynucleotide

<400> SEQUENCE: 89
gtggtttgta gtaatgttag tggttaggtg tatggtttgg gttatttgtt gaatgagtag      60
gttgatggtt ttgataataa                                                  80

<210> SEQ ID NO 90
<211> LENGTH: 80
<212> TYPE: DNA
<213> ORGANISM: Artificial Sequence
<220> FEATURE:
<223> OTHER INFORMATION: Description of Artificial Sequence: Synthetic
      mtDNA H-strand polynucleotide

<400> SEQUENCE: 90
gtggtttgta gtaatgttag cggttaggcg tacggttcgg gttattggtt gaatgagtag      60
gttgatggtt tcgataataa                                                  80

<210> SEQ ID NO 91
<211> LENGTH: 80
<212> TYPE: DNA
<213> ORGANISM: Artificial Sequence
<220> FEATURE:

```
<223> OTHER INFORMATION: Description of Artificial Sequence: Synthetic
      mtDNA H-strand polynucleotide

<400> SEQUENCE: 91
gtggtttgta gtaatgttag tggttaggcg tatggtttgg gttattggtt gaatgagtag    60
gttgatggtt ttgataataa                                                80

<210> SEQ ID NO 92
<211> LENGTH: 80
<212> TYPE: DNA
<213> ORGANISM: Artificial Sequence
<220> FEATURE:
<223> OTHER INFORMATION: Description of Artificial Sequence: Synthetic
      mtDNA H-strand polynucleotide

<400> SEQUENCE: 92
gtggtttgta gtaatgttag tggttaggtg tatggtttgg gttattggtt gaatgagtag    60
gttgatggtt tcgataataa                                                80

<210> SEQ ID NO 93
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(6)
<223> OTHER INFORMATION: Any amino acid and this region may encompass 2
      to 4 residues
<220> FEATURE:
<221> NAME/KEY: MOD_RES
<222> LOCATION: (8)..(10)
<223> OTHER INFORMATION: Any amino acid and this region may encompass 2
      to 3 residues
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(23)
<223> OTHER INFORMATION: Any amino acid
<220> FEATURE:
<223> OTHER INFORMATION: see specification as filed for detailed
      description of substitutions and preferred embodiments

<400> SEQUENCE: 93

Xaa Cys Xaa Xaa Xaa Xaa Cys Xaa Xaa Xaa Phe Xaa Xaa Xaa Xaa Xaa
1               5                   10                  15

Leu Xaa Xaa His Xaa Xaa Xaa His
            20

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 94

Thr Gly Glu Lys
1

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Thr Gly Glu Lys Pro
1               5

<210> SEQ ID NO 96
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ser Asp Val Leu Ser Ala Arg Asn Asp His Arg Ile Asn Arg Ser
1               5                   10                  15

Asp Thr Leu Ser Arg His Asn His His Arg Lys Thr
            20                  25

<210> SEQ ID NO 97
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Arg Ser Asp His Leu Ser Thr His Ser Asn Thr Arg Lys Asn Gly Gly
1               5                   10                  15

Gly Arg Ser Asp Ser Leu Ser Thr Ala Gly Ala Asn Arg Thr Thr
            20                  25                  30

<210> SEQ ID NO 98
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ser Asp Val Leu Ser Val Thr Asn Gln His Arg Thr Lys Arg Ser
1               5                   10                  15

Asp His Leu Ser Glu Asn Asn Ser Ser Arg Thr Arg
            20                  25

<210> SEQ ID NO 99
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 99

Arg Ser Asp His Leu Ser Gln Thr Ser Ser Asn Arg Lys Thr Arg Ser
1               5                   10                  15

Asp His Leu Ser Asn Arg Ser Asp Asp Arg Lys Lys
            20                  25

<210> SEQ ID NO 100
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Arg Ser Asp His Leu Ser Glu Arg Lys Asp Ala Arg Ile Thr Gly Gly
1               5                   10                  15

Gly Arg Ser Asp His Leu Ser Asn Arg Ser Asp Asp Arg Lys Lys
            20                  25                  30

<210> SEQ ID NO 101
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Ser Asp His Leu Ser Asn Arg Asn Asp Arg Lys Lys Arg Ser
1               5                   10                  15

Asp His Leu Ser Asn Gln Ser Ala Thr Arg Ile Thr
            20                  25

<210> SEQ ID NO 102
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Ser Asp His Leu Ser Gln Thr Ser Ser Asn Arg Lys Thr Arg Ser
1               5                   10                  15

Asp Asn Leu Ser Thr Arg Ser Asp Asn Arg Thr Lys
            20                  25

<210> SEQ ID NO 103
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Arg Ser Asp His Leu Ser Glu Asp Ser Ser His Arg Thr Arg Gly Gly
1               5                   10                  15

Gly Arg Ser Asp Ser Leu Ser Val Gln Asn Gln His Arg Ile Asn
            20                  25                  30

<210> SEQ ID NO 104
<211> LENGTH: 28
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ser Asp His Leu Ser Glu Arg Asn Asp Asn Arg Lys Arg Arg Ser
1               5                   10                  15
Asp His Leu Ser Gln Thr Ser Ala Asn Arg Thr Thr
            20                  25

<210> SEQ ID NO 105
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Arg Ser Asp Ser Leu Ser Gln Asn Ser Ser Asn Arg Lys Asn Gly Gly
1               5                   10                  15
Gly Arg Ser Asp Ser Leu Ser Gln Thr Ser Ser Asn Arg Lys Thr
            20                  25                  30

<210> SEQ ID NO 106
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Arg Ser Asp His Leu Ser Asn Thr Arg Asp Thr Arg Lys Lys Gly Gly
1               5                   10                  15
Gly Arg Ser Asp Ala Leu Ser Val Asp Ser Ser His Arg Thr Arg
            20                  25                  30

<210> SEQ ID NO 107
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Arg Ser Asp Thr Leu Ser Glu Arg Asn Asp His Arg Thr Thr Gly Gly
1               5                   10                  15
Gly Arg Ser Asp His Leu Ser Asn Arg Asn Asp Asp Arg Lys Lys
            20                  25                  30

<210> SEQ ID NO 108
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ser Asp His Leu Ser Glu Arg Asn Asp Asn Arg Lys Arg Arg Ser
1               5                   10                  15
```

Asp His Leu Ser Asn Arg Asn Asp Asp Arg Lys Lys
            20                  25

<210> SEQ ID NO 109
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Ser Asp His Leu Ser Glu Arg Asn Asp His Arg Thr Thr Arg Ser
1               5                   10                  15

Asp His Leu Ser Glu Arg Arg Asp Ser Arg Thr Asn
            20                  25

<210> SEQ ID NO 110
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Arg Ser Asp His Leu Ser Thr His Ser Asn Thr Arg Lys Asn Gly Gly
1               5                   10                  15

Gly Arg Ser Asp His Leu Ser Glu Arg Asn Asp His Arg Thr Thr
            20                  25                  30

<210> SEQ ID NO 111
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ser Asp Val Leu Ser Val Gln Asn Asn His Arg Ile Thr Arg Ser
1               5                   10                  15

Asp His Leu Ser Thr Ala Ser Ser Ala Arg Lys Thr
            20                  25

<210> SEQ ID NO 112
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Ser Asp Ala Leu Ser Val His Ser Asp Thr Arg Thr Lys Arg Ser
1               5                   10                  15

Asp Val Leu Ser Val Gln Asn Asn His Arg Ile Thr
            20                  25

<210> SEQ ID NO 113
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 113

Arg Ser Asp His Leu Thr Lys Asn Ser Asp His Leu Ser Arg Arg Ser
1               5                   10                  15

Asp Ser Leu Ser Val Gln Asn Gln His Arg Ile Asn
            20                  25

<210> SEQ ID NO 114
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ser Asp His Leu Thr Lys Asn Ser Asp His Leu Ser Arg Arg Ser
1               5                   10                  15

Asp His Leu Ser Asn Thr Arg Asp Thr Arg Lys Lys
            20                  25

<210> SEQ ID NO 115
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Thr Asn Asp Asp Leu Asn Thr Thr Ser Ser His Leu Ser Arg Gly Gly
1               5                   10                  15

Gly Arg Ser Asp His Leu Ser Glu Arg Asn Asp Asn Arg Lys Arg
            20                  25                  30

<210> SEQ ID NO 116
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Asn Asp Asp Leu Asn Thr Thr Ser Ser His Leu Ser Arg Arg Ser
1               5                   10                  15

Asp His Leu Ser Glu Arg Asn Asp His Arg Thr Thr
            20                  25
```